United States Patent
Morgan et al.

(10) Patent No.: US 11,963,727 B2
(45) Date of Patent: Apr. 23, 2024

(54) METHOD FOR SYSTEM ARCHITECTURE FOR MODULAR ENERGY SYSTEM

(71) Applicant: Cilag GmbH International, Zug (CH)

(72) Inventors: Joshua P. Morgan, Loveland, OH (US); Andrew W. Carroll, Cincinnati, OH (US); Jeffrey L. Aldridge, Lebanon, OH (US); Joshua M. Henderson, Montgomery, OH (US); James M. Vachon, West Chester, OH (US); Eitan T. Wiener, Loveland, OH (US); Daniel C. Herman, Maineville, OH (US); Jonathan T. Samuel, Blue Ash, OH (US); Jeffrey A. Bullock, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 406 days.

(21) Appl. No.: 17/217,405

(22) Filed: Mar. 30, 2021

(65) Prior Publication Data
US 2022/0313370 A1    Oct. 6, 2022

(51) Int. Cl.
*A61B 34/30*   (2016.01)
*A61B 34/00*   (2016.01)
(Continued)

(52) U.S. Cl.
CPC ............. *A61B 34/25* (2016.02); *G16H 20/40* (2018.01); *G16H 30/40* (2018.01); *G16H 40/67* (2018.01);
(Continued)

(58) Field of Classification Search
USPC ............. D24/107–231; 378/21–98; 382/100, 382/128–224; 704/1–275; 706/1–60,
(Continued)

(56) References Cited

U.S. PATENT DOCUMENTS

| 4,171,700 A | 10/1979 | Farin |
| 4,378,801 A | 4/1983 | Oosten |

(Continued)

FOREIGN PATENT DOCUMENTS

| EP | 0408160 A1 | 1/1991 |
| EP | 0473987 A1 | 3/1992 |

(Continued)

OTHER PUBLICATIONS

Makino Tetsuya; Liquid Crystal Display Device and Orientation Processing Method; Jan. 2, 2008 (Year: 2008).*

(Continued)

*Primary Examiner* — Marcellus J Augustin

(57) ABSTRACT

Mitigating a user interface display function of a modular energy system includes receiving formatted video data at a video data converter circuit, providing differential video signaling data to the display from the video data converter circuit, providing a copy of the differential video signaling data to a processor, and determining that the differential video signaling data is changing over time. Mitigating erroneous outputs from an isolated interface includes receiving a state of a first switch of a first footswitch coupled to a first comparator and a reference voltage coupled to the first comparator, receiving the state of the first switch coupled to the first duplicate comparator and the reference voltage coupled to the first duplicate comparator, comparing the output of the first comparator with the output of the first duplicate comparator, and determining activation or deactivation of a surgical instrument coupled to the controller based on the comparison.

14 Claims, 57 Drawing Sheets

(51) Int. Cl.
  *A61B 34/32* (2016.01)
  *G16H 20/40* (2018.01)
  *G16H 30/40* (2018.01)
  *G16H 40/67* (2018.01)
  *A61B 17/00* (2006.01)
  *A61B 18/00* (2006.01)
  *A61B 34/37* (2016.01)
  *A61B 90/00* (2016.01)

(52) U.S. Cl.
  CPC ............ *A61B 2017/00115* (2013.01); *A61B 2017/00221* (2013.01); *A61B 2017/00973* (2013.01); *A61B 2018/00994* (2013.01); *A61B 34/37* (2016.02); *A61B 2090/373* (2016.02); *A61B 2218/008* (2013.01)

(58) Field of Classification Search
  USPC ................................ 706/900–903; 606/6–60
  See application file for complete search history.

(56) References Cited

U.S. PATENT DOCUMENTS

| | | |
|---|---|---|
| 4,640,279 A | 2/1987 | Beard |
| 4,849,752 A | 7/1989 | Bryant |
| D303,787 S | 10/1989 | Messenger et al. |
| 5,041,110 A | 8/1991 | Fleenor |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| 5,325,270 A | 6/1994 | Wenger et al. |
| 5,383,880 A | 1/1995 | Hooven |
| 5,395,033 A | 3/1995 | Byrne et al. |
| 5,425,375 A | 6/1995 | Chin et al. |
| 5,613,158 A | 3/1997 | Savage |
| D379,346 S | 5/1997 | Mieki |
| 5,667,517 A | 9/1997 | Hooven |
| 5,690,504 A | 11/1997 | Scanlan et al. |
| 5,693,042 A | 12/1997 | Boiarski et al. |
| 5,724,468 A | 3/1998 | Leone et al. |
| 5,788,688 A | 8/1998 | Bauer et al. |
| 5,817,119 A | 10/1998 | Klieman et al. |
| 5,849,020 A | 12/1998 | Long et al. |
| 5,865,361 A | 2/1999 | Milliman et al. |
| 5,872,481 A | 2/1999 | Sevic et al. |
| 5,901,150 A | 5/1999 | Jhuboo et al. |
| 5,910,139 A | 6/1999 | Cochran et al. |
| 5,941,846 A | 8/1999 | Duffy et al. |
| 6,019,745 A | 2/2000 | Gray |
| 6,049,467 A | 4/2000 | Tamarkin et al. |
| 6,055,062 A | 4/2000 | Dina et al. |
| 6,055,458 A | 4/2000 | Cochran et al. |
| D431,811 S | 10/2000 | Nishio et al. |
| 6,179,136 B1 | 1/2001 | Kluge et al. |
| 6,269,411 B1 | 7/2001 | Reasoner |
| 6,273,750 B1 | 8/2001 | Malkowski, Jr. |
| 6,288,606 B1 | 9/2001 | Ekman et al. |
| H2037 H | 7/2002 | Yates et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,843,657 B2 | 1/2005 | Driscoll et al. |
| 6,888,848 B2 | 5/2005 | Beshai et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,268,684 B2 | 9/2007 | Tethrake et al. |
| 7,331,699 B2 | 2/2008 | Gawalkiewicz et al. |
| 7,344,532 B2 | 3/2008 | Goble et al. |
| 7,353,068 B2 | 4/2008 | Tanaka et al. |
| D575,792 S | 8/2008 | Benson |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,695,485 B2 | 4/2010 | Whitman et al. |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| 8,057,492 B2 | 11/2011 | Ortiz et al. |
| D655,678 S | 3/2012 | Kobayashi et al. |
| D657,368 S | 4/2012 | Magee et al. |
| 8,187,263 B2 | 5/2012 | Behnke et al. |
| 8,218,279 B2 | 7/2012 | Liao et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,551,088 B2 | 10/2013 | Falkenstein et al. |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| 8,840,609 B2 | 9/2014 | Stuebe |
| D716,333 S | 10/2014 | Chotin et al. |
| 8,911,437 B2 | 12/2014 | Horlle et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,961,441 B2 | 2/2015 | Cioanta et al. |
| 8,968,296 B2 | 3/2015 | McPherson |
| 8,986,288 B2 | 3/2015 | Konishi |
| 9,017,326 B2 | 4/2015 | DiNardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,370,361 B2 | 6/2016 | Viola et al. |
| 9,391,670 B2 | 7/2016 | Brukalo et al. |
| 9,427,255 B2 | 8/2016 | Griffith et al. |
| 9,430,438 B2 | 8/2016 | Biskup |

(56) References Cited

U.S. PATENT DOCUMENTS

| | | |
|---|---|---|
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,589,720 B2 | 3/2017 | Akahane |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| D806,721 S | 1/2018 | Fischer |
| 9,867,670 B2 | 1/2018 | Brannan et al. |
| 9,892,483 B2 | 2/2018 | Lee et al. |
| 9,892,564 B1 | 2/2018 | Cvetko et al. |
| 9,907,196 B2 | 2/2018 | Susini et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,794 B2 * | 12/2019 | Gilreath ............... A61B 1/0684 |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,027 B2 | 6/2020 | Aldridge et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,898,279 B2 | 1/2021 | Yang |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,077,312 B2 | 8/2021 | Sturman et al. |
| 11,083,489 B2 | 8/2021 | Fujii et al. |
| 11,116,587 B2 | 9/2021 | Wolf et al. |
| 11,185,379 B2 | 11/2021 | Shuma et al. |
| D939,545 S | 12/2021 | Oberkircher et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,304,763 B2 | 4/2022 | Shelton, IV et al. |
| 11,314,846 B1 | 4/2022 | Colin et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,478,820 B2 | 10/2022 | Bales, Jr. et al. |
| 11,504,192 B2 | 11/2022 | Shelton, IV et al. |
| 11,510,750 B2 | 11/2022 | Dulin et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| 11,659,023 B2 | 5/2023 | Shelton, IV et al. |
| 11,712,309 B2 | 8/2023 | Barak et al. |
| 2001/0029315 A1 | 10/2001 | Sakurai et al. |
| 2001/0031975 A1 | 10/2001 | Whitman et al. |
| 2002/0022836 A1 | 2/2002 | Goble et al. |
| 2002/0052563 A1 | 5/2002 | Penn et al. |
| 2002/0148942 A1 | 10/2002 | Payne et al. |
| 2002/0151770 A1 | 10/2002 | Noll et al. |
| 2002/0183734 A1 | 12/2002 | Bommannan et al. |
| 2003/0007321 A1 | 1/2003 | Dayley |
| 2003/0040670 A1 | 2/2003 | Govari |
| 2003/0050654 A1 | 3/2003 | Whitman et al. |
| 2003/0078631 A1 | 4/2003 | Nelson et al. |
| 2003/0093103 A1 | 5/2003 | Malackowski et al. |
| 2003/0114851 A1 | 6/2003 | Truckai et al. |
| 2003/0130677 A1 | 7/2003 | Whitman et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0094597 A1 | 5/2004 | Whitman et al. |
| 2004/0111045 A1 | 6/2004 | Sullivan et al. |
| 2004/0111081 A1 | 6/2004 | Whitman et al. |
| 2004/0153724 A1 | 8/2004 | Nicholson et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0021026 A1 | 1/2005 | Baily |
| 2005/0070800 A1 | 3/2005 | Takahashi |
| 2005/0090730 A1 * | 4/2005 | Cortinovis ............... F16D 51/50 600/407 |
| 2005/0113815 A1 | 5/2005 | Ritchie et al. |
| 2005/0113823 A1 | 5/2005 | Reschke et al. |
| 2005/0127868 A1 | 6/2005 | Calhoon et al. |
| 2005/0127869 A1 | 6/2005 | Calhoon et al. |
| 2005/0131390 A1 | 6/2005 | Heinrich et al. |
| 2005/0159778 A1 | 7/2005 | Heinrich et al. |
| 2005/0165390 A1 | 7/2005 | Mauti et al. |
| 2005/0173490 A1 | 8/2005 | Shelton, IV |
| 2005/0229110 A1 | 10/2005 | Gegner et al. |
| 2005/0251233 A1 | 11/2005 | Kanzius |

(56) References Cited

U.S. PATENT DOCUMENTS

| | | |
|---|---|---|
| 2006/0020213 A1 | 1/2006 | Whitman et al. |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0212069 A1 | 9/2006 | Shelton, IV |
| 2006/0256516 A1 | 11/2006 | Cho |
| 2006/0278680 A1 | 12/2006 | Viola et al. |
| 2006/0278681 A1 | 12/2006 | Viola et al. |
| 2006/0289600 A1 | 12/2006 | Wales et al. |
| 2007/0061393 A1 | 3/2007 | Moore |
| 2007/0076363 A1 | 4/2007 | Liang et al. |
| 2007/0085602 A1 | 4/2007 | Park et al. |
| 2007/0136218 A1 | 6/2007 | Bauer et al. |
| 2007/0282321 A1 | 12/2007 | Shah et al. |
| 2008/0072896 A1 | 3/2008 | Setzer et al. |
| 2008/0090652 A1 | 4/2008 | Kuehling et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0054908 A1 | 2/2009 | Zand et al. |
| 2009/0101692 A1 | 4/2009 | Whitman et al. |
| 2009/0131929 A1 | 5/2009 | Shimizu |
| 2009/0216091 A1 | 8/2009 | Arndt |
| 2009/0228024 A1 | 9/2009 | Whitfield et al. |
| 2009/0234352 A1 | 9/2009 | Behnke et al. |
| 2009/0273353 A1 | 11/2009 | Kroh et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0015660 A1 | 1/2011 | Wiener et al. |
| 2011/0092972 A1 | 4/2011 | Allen |
| 2011/0093796 A1 | 4/2011 | Plummer et al. |
| 2011/0106567 A1 | 5/2011 | Asher |
| 2011/0125149 A1 | 5/2011 | El-Galley et al. |
| 2011/0130689 A1 | 6/2011 | Cohen et al. |
| 2011/0238063 A1 | 9/2011 | Gregg |
| 2011/0245630 A1 | 10/2011 | St. Pierre et al. |
| 2011/0273465 A1 | 11/2011 | Konishi et al. |
| 2011/0288451 A1 | 11/2011 | Sanai et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0319890 A1 | 12/2012 | McCormack et al. |
| 2013/0031201 A1 | 1/2013 | Kagan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0097903 A1 | 4/2014 | Aoki et al. |
| 2014/0108048 A1 | 4/2014 | Cohn |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0378958 A1 | 12/2014 | Leussler |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2015/0300923 A1 | 10/2015 | Halbert |
| 2015/0334879 A1 | 11/2015 | Fricker |
| 2015/0373115 A1 | 12/2015 | Breakstone et al. |
| 2016/0000495 A1 | 1/2016 | Elliott et al. |
| 2016/0045247 A1 | 2/2016 | Heim et al. |
| 2016/0045365 A1 | 2/2016 | Foster et al. |
| 2016/0058286 A1 | 3/2016 | Joshua et al. |
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0164466 A1 | 6/2016 | Briffa et al. |
| 2016/0199240 A1 | 7/2016 | Newkirk et al. |
| 2016/0225192 A1 | 8/2016 | Jones et al. |
| 2016/0249945 A1 | 9/2016 | Shelton, IV et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0007146 A1 | 1/2017 | Schulhauser et al. |
| 2017/0024978 A1 | 1/2017 | Gulrez et al. |
| 2017/0078455 A1 | 3/2017 | Fisher et al. |
| 2017/0080346 A1 | 3/2017 | Abbas |
| 2017/0090507 A1 | 3/2017 | Wiener et al. |
| 2017/0151011 A1 | 6/2017 | Brustad et al. |
| 2017/0189096 A1 | 7/2017 | Danziger et al. |
| 2017/0202595 A1 | 7/2017 | Shelton, IV |
| 2017/0209718 A1 | 7/2017 | Tanis et al. |
| 2017/0251305 A1 | 8/2017 | Fathollahi |
| 2017/0252091 A1 | 9/2017 | Honda |
| 2017/0296213 A1 | 10/2017 | Swensgard et al. |
| 2017/0319259 A1 | 11/2017 | Dunning |
| 2017/0360466 A1 | 12/2017 | Brown et al. |
| 2018/0014872 A1 | 1/2018 | Dickerson |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0166809 A1 | 6/2018 | Brogan et al. |
| 2018/0206909 A1 | 7/2018 | Brustad et al. |
| 2018/0221005 A1 | 8/2018 | Hamel et al. |
| 2018/0228528 A1 | 8/2018 | Fraasch et al. |
| 2018/0239856 A1 | 8/2018 | Takeuchi et al. |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De la Barrera |
| 2018/0367870 A1 | 12/2018 | Shih |
| 2019/0000478 A1 | 1/2019 | Messerly et al. |
| 2019/0069957 A1 | 3/2019 | Barral et al. |
| 2019/0110855 A1* | 4/2019 | Barral .................. A61B 90/37 |
| 2019/0117322 A1* | 4/2019 | Laubenthal ............ A61B 17/00 |
| 2019/0125455 A1 | 5/2019 | Shelton, IV et al. |
| 2019/0197712 A1* | 6/2019 | Talbert ............... A61B 1/00186 |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206563 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0247664 A1 | 8/2019 | Irazoqui et al. |
| 2019/0269457 A1 | 9/2019 | Schofield et al. |
| 2019/0278262 A1 | 9/2019 | Taylor et al. |
| 2019/0279524 A1 | 9/2019 | Stoyanov et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0030044 A1 | 1/2020 | Wang et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |

(56) References Cited

U.S. PATENT DOCUMENTS

| | | |
|---|---|---|
| 2020/0078083 A1 | 3/2020 | Sprinkle et al. |
| 2020/0078089 A1 | 3/2020 | Henderson et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0129223 A1 | 4/2020 | Angeles et al. |
| 2020/0159313 A1 | 5/2020 | Gibby et al. |
| 2020/0237422 A1 | 7/2020 | Canady |
| 2020/0265398 A1 | 8/2020 | Lembo |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0342228 A1 | 10/2020 | Prevrhal et al. |
| 2020/0405375 A1 | 12/2020 | Shelton, IV et al. |
| 2021/0045804 A1* | 2/2021 | Schofield ........... A61B 18/1206 |
| 2021/0121246 A1 | 4/2021 | Gudalo |
| 2021/0169578 A1 | 6/2021 | Calloway et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0264680 A1 | 8/2021 | Cvetko, et al. |
| 2021/0313938 A1 | 10/2021 | Tanaka et al. |
| 2021/0338343 A1 | 11/2021 | Swaffield et al. |
| 2021/0385889 A1 | 12/2021 | Patel |
| 2022/0032442 A1 | 2/2022 | Sheffield et al. |
| 2022/0104867 A1 | 4/2022 | Shelton, IV et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0151704 A1 | 5/2022 | Nikou |
| 2022/0155910 A1 | 5/2022 | Jeong |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2023/0038130 A1 | 2/2023 | Cvetko et al. |
| 2023/0039037 A1 | 2/2023 | Henderson et al. |
| 2023/0069787 A1 | 3/2023 | Henderson et al. |
| 2023/0072423 A1 | 3/2023 | Osborn et al. |
| 2023/0346446 A1 | 11/2023 | Henderson et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| JP | S635457 A | 1/1988 |
| JP | H8280706 A | 10/1996 |
| JP | H1069453 A | 3/1998 |
| JP | 2000089850 A | 3/2000 |
| JP | 2001029353 A | 2/2001 |
| JP | 2001128993 A | 5/2001 |
| JP | 2002336194 A | 11/2002 |
| JP | 2006303167 A | 11/2006 |
| JP | 2007174666 A | 7/2007 |
| JP | 2009291308 A | 12/2009 |
| JP | 2010063883 A | 3/2010 |
| JP | 2014210052 A | 11/2014 |
| KR | 20110081018 A | 7/2011 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | WO-2017058617 | 4/2017 |
| WO | WO-2018116247 A1 | 6/2018 |
| WO | WO-2019215354 A1 | 11/2019 |
| WO | WO-2021044136 A1 | 3/2021 |

OTHER PUBLICATIONS

Li L; Slip Ring Digital Video Signal Conductive Transmission Performance Detecting Method, Involves Comparing Video Images Of First And Second Digital Video Interface Displays For Judging Transmission Performance Of Video Signal Of Slip Ring; Nov. 24, 2017 (Year: 2017).*

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committe, published Aug. 2003.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

"BOWA ARC 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30_EN.pdf (Year: 2018).

"Electrosurgical Generator ECONT-0201.3" Mar. 18, 2018, posted at contact-endoscopy.com, [site visited Aug. 6, 2021], https://contact-endoscopy.com/electrosurgical-system (Year: 2018).

* cited by examiner

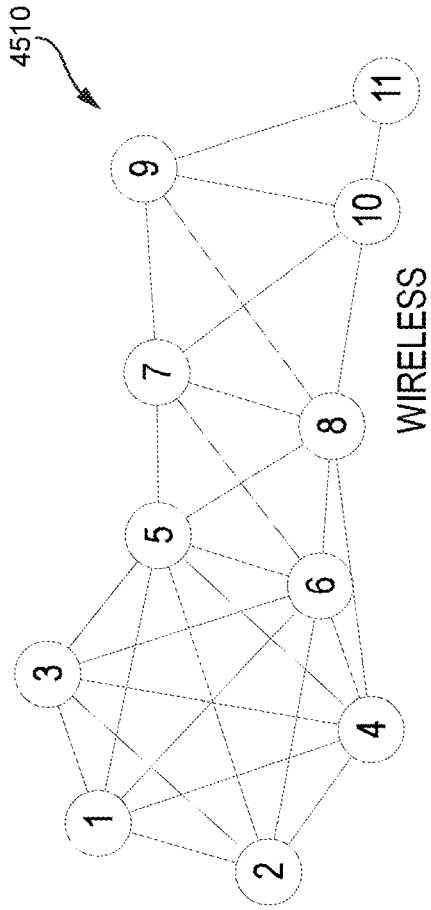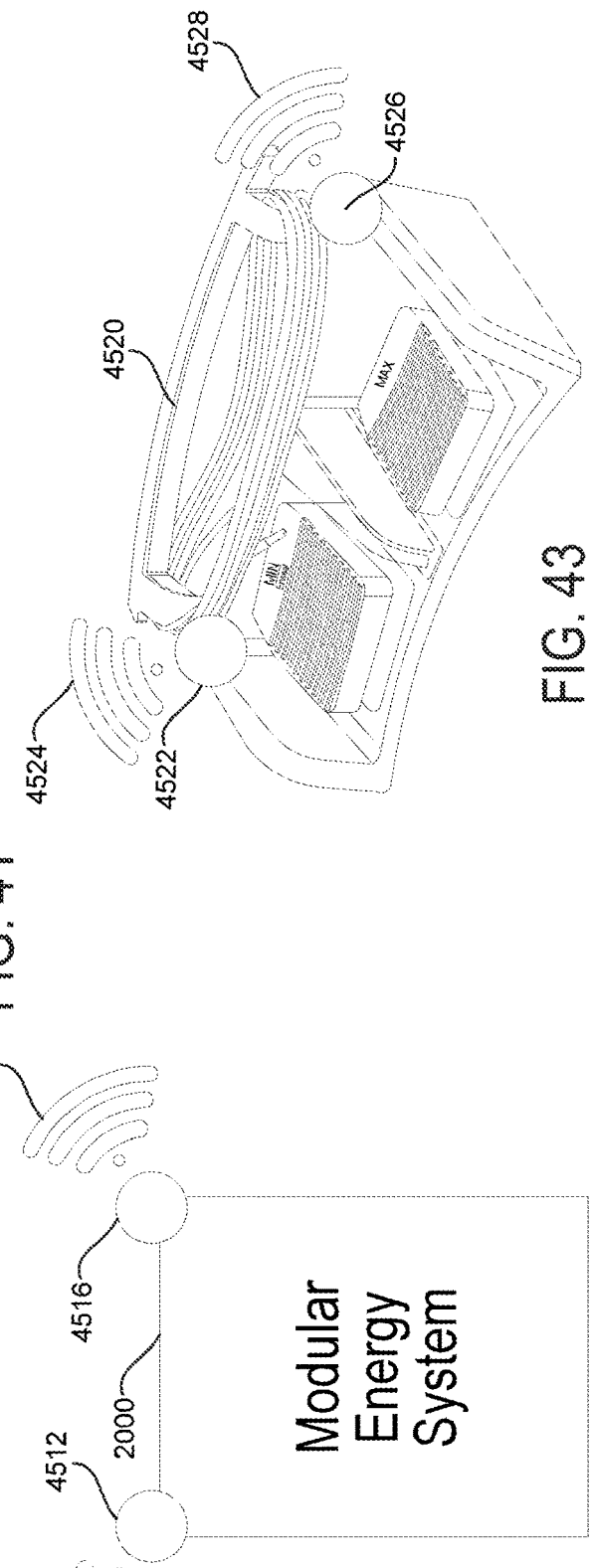
FIG. 41
FIG. 42
FIG. 43

METHOD FOR SYSTEM ARCHITECTURE FOR MODULAR ENERGY SYSTEM

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

A user interface for a modular energy system may be improved by including audio mitigation techniques. There is a risk that an energy generator component of a modular energy system may improperly generate a visual or audio tone to indicate alarms, alerts, and energy activation of electrosurgical/ultrasonic instruments as may be required by external standards. The risk of failure to generate a proper visual or audio tone are undesirable during the operation of the electrosurgical/ultrasonic instrument. Audio feedback to alert the user that an electrosurgical/ultrasonic instrument has been energized by an energy module is part of proper operation protocol of the electrosurgical/ultrasonic instrument. Thus, there is a need to mitigate or eliminate any potential risk of video or audio tone failures to reduce the risk of applying undesired energy by an electrosurgical/ultrasonic instrument during an operation.

SUMMARY

In one aspect, the present disclosure provides a method of mitigating a function of a user interface (UI) display of a modular energy system. The method comprises receiving, by a video data converter circuit, formatted video data at an input channel of the video data converter circuit, wherein the input channel is coupled to a processor and the formatted video data represents an expected image to be displayed on a display, the video data converter having two output channels, wherein a first output channel is coupled to the display and a second output channel is coupled back to the processor, wherein the processor is configured to couple to a surgical instrument; providing, by the video data converter circuit, differential video signaling data to the display from the first output channel of the video data converter circuit; providing, by the video data converter circuit, a copy of the differential video signaling data to the processor from the second output channel; and determining, by the processor, whether the differential video signaling data on the second output channel is changing over time.

In one aspect, the present disclosure provides a method of mitigating erroneous outputs from an isolated interface circuit for a modular energy system. The method comprising: receiving, at a first input of a first comparator, a state of a first switch of a first footswitch coupled to the first input of the first comparator and a reference voltage coupled to a second input of the first comparator; receiving, at a first input of a first duplicate comparator, the state of the first switch coupled to the first input of the first duplicate comparator and the reference voltage coupled to a second input of the first duplicate comparator; comparing, by a controller coupled to outputs of the first comparator and the first duplicate comparator, the output of the first comparator with the output of the first duplicate comparator; and determining, by the controller, activation or deactivation of a surgical instrument coupled to the controller based on the comparison.

In one aspect, the present disclosure provides an audio circuit. The audio circuit comprises a processor configured to generate a digital audio signal, wherein the audio signal comprises audio data bits inserted on the rising edge of a clock signal and additional data bits inserted on a falling edge of the clock signal, wherein the audio data bits on the rising edge represent a digital audio tone and the additional data bits inserted on the falling edge represent a unique tone identification of the audio data bits on the rising edge; a digital-to-analog converter configured to: receive the digital audio signal; convert the audio data bits inserted on the rising edge; and ignore the additional data bits on the falling edge; an audio mitigation control module configured to: receive the digital audio signal; read the additional data bits on the falling edge; and confirm that the audio data bits inserted on the rising edge represent a correct digital audio tone based on the unique tone identification.

In another aspect, the present disclosure provides a circuit for mitigating a function of a user interface (UI) display of a modular energy system. The circuit comprises a processor configured to couple to a surgical instrument; a display; and a video data converter circuit configured to receive formatted video data that represents an expected image to be displayed on the display and to provide differential video signaling data to the display and a copy of the differential video signaling data to the processor; wherein the processor is configured to determine whether the copy of the differential video signaling data is changing over time.

In yet another aspect, the present disclosure provides a method of mitigating a function of a user interface (UI) display of a modular energy system. The method comprises receiving, by a video data converter circuit, formatted video data at an input channel of the video data converter circuit, wherein the input channel is coupled to a processor and the formatted video data represents an expected image to be displayed on a display, the video data converter having two output channels, wherein a first output channel is coupled to the display and a second output channel is coupled back to the processor, wherein the processor is configured to couple to a surgical instrument; providing, by the video data converter circuit, differential video signaling data to the display from the first output channel of the video data converter circuit; providing, by the video data converter circuit, a copy of the differential video signaling data to the processor from the second output channel; and determining, by the processor, whether the differential video signaling data on the second output channel is changing over time.

In yet another aspect, the present disclosure provides an audio circuit. The audio circuit comprises a processor; an audio amplifier coupled to the processor by audio data lines; an audio mitigation control circuit coupled to the processor and the audio amplifier, a digital-to-analog converter (DAC) comprising a first analog output channel coupled to a first speaker; a first current shunt coupled in series with the first speaker; a first current sense amplifier having an input coupled to the first current shunt and an output coupled to an input of a first analog-to-digital converter (ADC); and wherein the output of the first ADC is coupled to the audio mitigation control module; wherein the audio mitigation control circuit is configured to: fetch, from a memory coupled to the audio mitigation control circuit, a unique identification number to identify an expected audio file, the audio file comprising audio data comprising an audio asset and a unique super-audible tone to identify the audio asset; receive the audio data from the output of the first ADC; filter the audio data to isolate a super-audible frequency range of the audio data; calculate a fast Fourier transform (FFT) on the audio data in the isolated super-audible frequency range; perform a peak detection function on the FFT results to detect a super-audible tone; compare the detected super-audible tone to the unique identification number to identify the expected audio file; and determine a specific audio file transmitted to the audio amplifier based on the comparison.

In yet another aspect, the present disclosure provides an audio circuit. The audio circuit comprises a processor; an audio amplifier coupled to the processor by audio data lines; an audio mitigation control circuit coupled to the processor and the audio amplifier, wherein the audio mitigation control circuit is configured to: fetch, from a memory coupled to the audio mitigation control circuit, a unique identification number to identify an expected audio file, the audio file comprising audio data comprising an audio asset and a unique super-audible tone to identify the audio asset; receive the audio data transmitted from the processor to the audio amplifier; filter the audio data to isolate a super-audible frequency range of the audio data; calculate a fast Fourier transform (FFT) on the audio data in the isolated super-audible frequency range; perform a peak detection function on the FFT results to detect a super-audible tone; compare the detected super-audible tone to the unique identification number to identify the expected audio file; and determine a specific audio file transmitted to the audio amplifier based on the comparison.

In one aspect, the present disclosure provides an isolated interface circuit for a modular energy system. The isolated interface circuit comprises a comparator comprising a first input configured to couple to a switch, a second input configured to couple to a reference voltage, and an output; a duplicate comparator comprising a first input configured to couple to the switch, a second input configured to couple to the reference voltage, and an output; an expander circuit comprising at least two inputs, wherein the output of the comparator is coupled to one of the at least two inputs of the expander circuit, and wherein the output of the duplicate comparator is coupled to other of the at least two inputs of the expander circuit, the expander circuit comprising an output; an isolator circuit comprising an input and an output, wherein the input is coupled to the output of the expander circuit; and a controller coupled to the output of the isolator circuit, wherein the controller is configured to: compare the output of the comparator with the output of the duplicate comparator; and determine activation or deactivation of a surgical instrument coupled to the controller based on the comparison.

In another aspect, the present disclosure provides an isolated interface circuit for a modular energy system. The isolated interface circuit comprises a first comparator comprising a first input configured to couple to a first switch, a second input configured to couple to a reference voltage, and an output; a second comparator comprising a first input configured to couple to a second switch, a second input configured to couple to the reference voltage, and an output; a first duplicate comparator comprising a first input configured to couple to the first switch, a second input configured to couple to the reference voltage, and an output; a second duplicate comparator comprising a first input configured to couple to the second switch, a second input configured to couple to the reference voltage, and an output; an expander circuit comprising at least four inputs, wherein each of the outputs of the first and second comparators is coupled to an input of the expander circuit, and wherein each of the outputs of the first and second duplicate comparators is coupled an input of the expander circuit, the expander circuit comprising an output; an isolator circuit comprising an input and an output, wherein the input is coupled to the output of the expander circuit; and a controller coupled to the output of the isolator circuit, wherein the controller is configure to: compare the output of the first comparator with the output of the first duplicate comparator; compare the output of the second comparator with the output of the second duplicate comparator; and determine activation or deactivation of a surgical instrument coupled to the controller based on the comparison.

In yet another aspect, the present disclosure provides a method of mitigating erroneous outputs from an isolated interface circuit for a modular energy system. The method comprises receiving, at a first input of a first comparator, a state of a first switch of a first footswitch coupled to the first input of the first comparator and a reference voltage coupled to a second input of the first comparator; receiving, at a first input of a first duplicate comparator, the state of the first switch coupled to the first input of the first duplicate comparator and the reference voltage coupled to a second input of the first duplicate comparator; comparing, by a controller coupled to outputs of the first comparator and the first duplicate comparator, the output of the first comparator with the output of the first duplicate comparator; and determining, by the controller, activation or deactivation of a surgical instrument coupled to the controller based on the comparison.

In one aspect, a modular energy system for use in a surgical environment, may include a plurality of modules, in which each of the plurality of modules is composed of one of an initial module, a terminal module, and a functional module. Each of the functional modules and the terminal module may include a module control circuit and a local data bus. Each local data bus may include a communication switch, a first switch data path configured to permit data communication between the communication switch and the module control circuit, a second switch data path in data communication with the communication switch, and a third switch data path in data communication with the communication switch. The initial module may include a physical layer transceiver (PHY) in data communication with an initial module control circuit. The modular energy system may also include a termination unit in data communication with the third data path of the terminal module. Further, the modular energy system may include an internal data bus composed of a serial array of the local data busses of the plurality of functional modules and the terminal module, in which a third switch data path of a functional module N is in data communication with a second switch data path of a functional module N+1, and a second switch data path of the terminal module is in data communication with a third switch data path of a preceding functional module. Additionally, the internal data bus may further include the physical layer transceiver (PHY) of the initial module in data communication with a second switch data path of a succeeding functional module.

In one aspect, a system for notifying a user of a processor boot-up fault in a computerized device, may include a timing circuit and a multicolor visualization device. In one aspect, the computerized device may include a processor and a memory unit configured to store a plurality of instructions for execution by the processor. The processor may be configured to initiate a boot-up process based on at least some of the instructions stored in the memory unit when power is applied to the computerized device. The timing circuit may be configured to initiate a timing procedure when power is applied to the computerized device. In one aspect, the timing circuit may be configured to transmit a fault signal to the multicolor visualization device when the timing circuit attains a predetermined value.

In one aspect, a modular energy system for use in a surgical environment may include a plurality of functional modules and an internal data bus comprising a serial array of the local data busses of the plurality of functional modules in mutual data communication. At least two of the plurality of functional modules may include a module control circuit, a local data bus having a communication switch in data communication with the control circuit, and a transceiver timer. A first functional module of the plurality of functional modules may be configured to transmit a data message over the internal data bus to a second functional module of the plurality of functional modules. The first functional module may be configured to obtain a transmission time from a transceiver timer of the first functional module, append the transmission time to the data message, and transmit the data message over the internal data bus to the second functional module. The second functional module may be configured to receive the data message over the internal data bus from the first functional module, obtain a receipt time from a transceiver timer of the second functional module, and obtain the transmission time from the data message.

A smart surgical system may include a plurality of surgical subsystems in mutual data communication over a surgical system bus, and a modular energy system. At least one of the plurality of surgical subsystems comprises a subsystem transceiver timer. The modular energy system may include a plurality of functional modules, in which at least one functional module may include a module control circuit, a local data bus comprising a communication switch in data communication with the control circuit, and a transceiver timer. An internal data bus of the modular energy system may be composed of a serial array of the local data busses of the plurality of functional modules in mutual data communication. The smart surgical system may also include a system data bus composed of the internal data bus of the modular energy system in data communication with the surgical system bus. A transmitting component of the smart surgical system may include one of the plurality of surgical subsystems or one of the plurality of functional modules, A receiving component of the smart surgical system may include one of the plurality of surgical subsystems or one of the plurality of functional modules and is not the transmitting component. The transmitting component may be configured to transmit a data message over the system data bus to the receiving component. The transmitting component may be configured to obtain a transmission time from a transceiver timer of the transmitting component, append the transmission time to the data message, and transmit the data message over the system bus to the receiving component. The receiving component may be configured to receive the data message over the system data bus from the transmitting component, obtain a receipt time from a transceiver timer of the receiving component, and obtain the transmission time from the data message.

FIGURES

The various aspects described herein, both as to organization and methods of operation, together with further objects and advantages thereof, may best be understood by reference to the following description, taken in conjunction with the accompanying drawings as follows.

FIG. 41 is a schematic representation of a wireless mesh network, in accordance with at least one aspect of the present disclosure.

FIG. 42 is a bock diagram of a modular energy system comprising multiple radios, in accordance with at least one aspect of the present disclosure.

FIG. 43 is a diagram of a footswitch comprising multiple radios, in accordance with at least aspect of the present disclosure.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Figure 1:
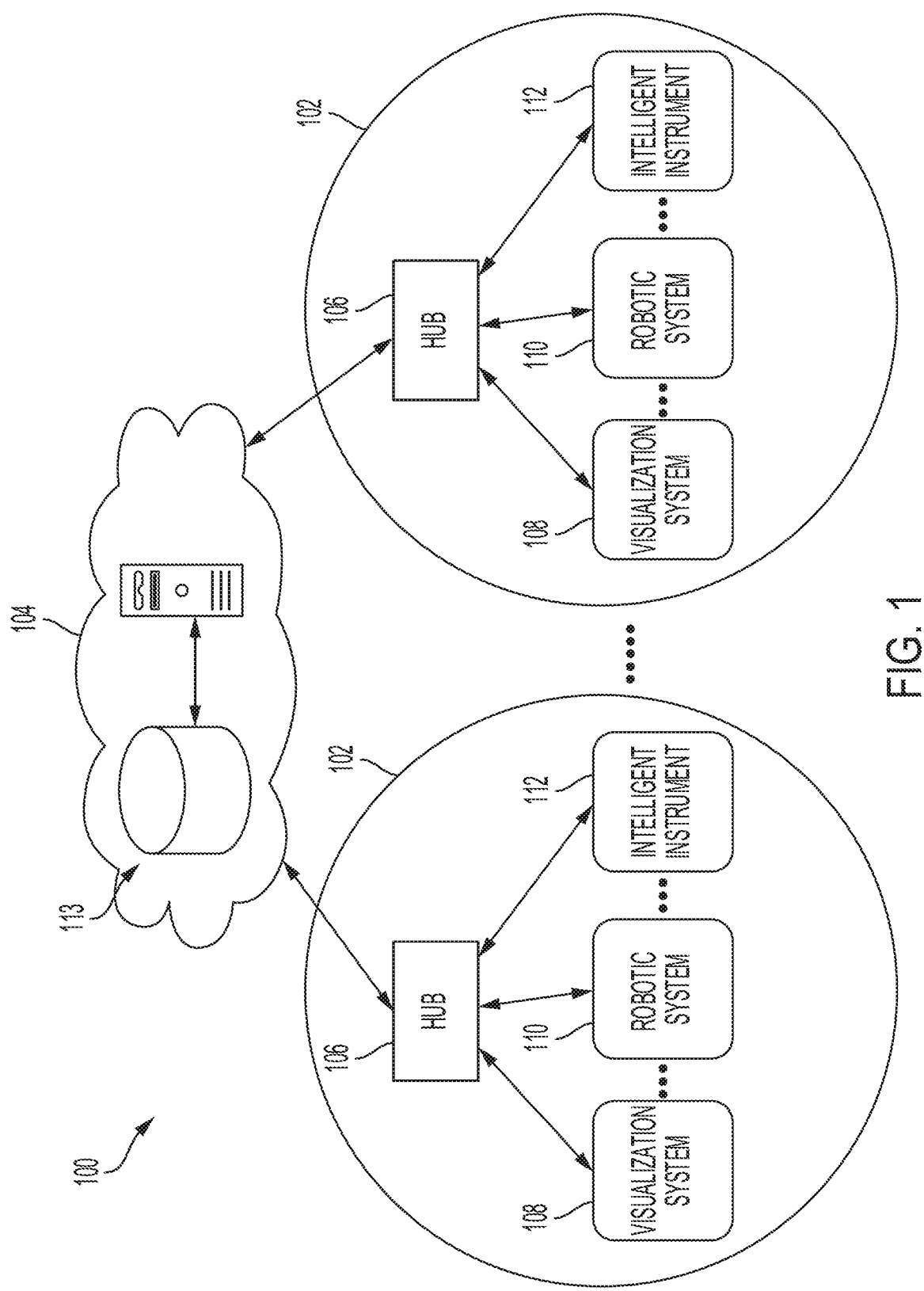
FIG. 1 is a block diagram of a computer-implemented interactive surgical system, in accordance with at least one aspect of the present disclosure.

Applicant of the present application owns the following U.S. Patent Applications filed on Mar. 30, 2021, the disclosure of each of which is herein incorporated by reference in its entirety:

U.S. patent application Ser. No. 17/217,394, titled METHOD FOR MECHANICAL PACKAGING FOR MODULAR ENERGY SYSTEM, now U.S. Patent Application Publication No. 2022/0322523;

U.S. patent application Ser. No. 17/217,402, titled BACKPLANE CONNECTOR ATTACHMENT MECHANISM FOR MODULAR ENERGY SYSTEM, now U.S. Patent Application Publication No. 2022/0317750;

U.S. patent application Ser. No. 17/217,436, titled BEZEL WITH LIGHT BLOCKING FEATURES FOR MODULAR ENERGY SYSTEM, now U.S. Patent Application Publication No. 2022/0313357;

U.S. patent application Ser. No. 17/217,446, titled HEADER FOR MODULAR ENERGY SYSTEM, now U.S. Patent Application Publication No. 2022/0313342;

U.S. patent application Ser. No. 17/217,403, titled SURGICAL PROCEDURALIZATION VIA MODULAR ENERGY SYSTEM, now U.S. Patent Application Publication No. 2022/0313341;

U.S. patent application Ser. No. 17/217,424, titled METHOD FOR ENERGY DELIVERY FOR MODULAR ENERGY SYSTEM, now U.S. Patent Application Publication No. 2022/0317751;

U.S. patent application Ser. No. 17/217,439, titled MODULAR ENERGY SYSTEM WITH DUAL AMPLIFIERS AND TECHNIQUES FOR UPDATING PARAMETERS THEREOF, now U.S. patent application Publication No. 2022/0321059;

U.S. patent application Ser. No. 17/217,471, titled MODULAR ENERGY SYSTEM WITH MULTI-ENERGY PORT SPLITTER FOR MULTIPLE ENERGY DEVICES, now U.S. Patent Application Publication No. 2022/0313373;

U.S. patent application Ser. No. 17/217,385, titled METHOD FOR INTELLIGENT INSTRUMENTS FOR MODULAR ENERGY SYSTEM, now U.S. Patent Application Publication No. 2022/0313369;

U.S. patent application Ser. No. 17/217,392, titled RADIO FREQUENCY IDENTIFICATION TOKEN FOR WIRELESS SURGICAL INSTRUMENTS, now U.S. Patent Application Publication No. 2022/0319693;

U.S. patent application Ser. No. 17/217,397, titled INTELLIGENT DATA PORTS FOR MODULAR ENERGY SYSTEMS, now U.S. Patent Application Publication No. 2022/0318179;

U.S. patent application Ser. No. 17/217,423, titled USER INTERFACE MITIGATION TECHNIQUES FOR MODULAR ENERGY SYSTEMS, now U.S. Patent Application Publication No. 2022/0313371;

U.S. patent application Ser. No. 17/7217,429, titled ENERGY DELIVERY MITIGATIONS FOR MODULAR ENERGY SYSTEMS, now U.S. Patent Application Publication No. 2022/0313338;

U.S. patent application Ser. No. 17/217,449, titled ARCHITECTURE FOR MODULAR ENERGY SYSTEM, now U.S. Patent Application Publication No. 2022/0313372; and U.S. patent application Ser. No. 17/217,461, titled MODULAR ENERGY SYSTEM WITH HARDWARE MITIGATED COMMUNICATION, now U.S. Patent Application Publication No. 2022/0319685.

Applicant of the present application owns the following U.S. patent applications filed Sep. 5, 2019, the disclosure of each of which is herein incorporated by reference in its entirety:

U.S. patent application Ser. No. 16/562,144, titled METHOD FOR CONTROLLING A MODULAR ENERGY SYSTEM USER INTERFACE, now U.S. Patent Application Publication No. 2020/0078106;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 20200078117;

U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design patent application Ser. No. 29/704,617, titled ALERT SCREEN FOR ENERGY MODULE.

Applicant of the present application owns the following U.S. Patent Provisional applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional application filed Sep. 7, 2018, the disclosure of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
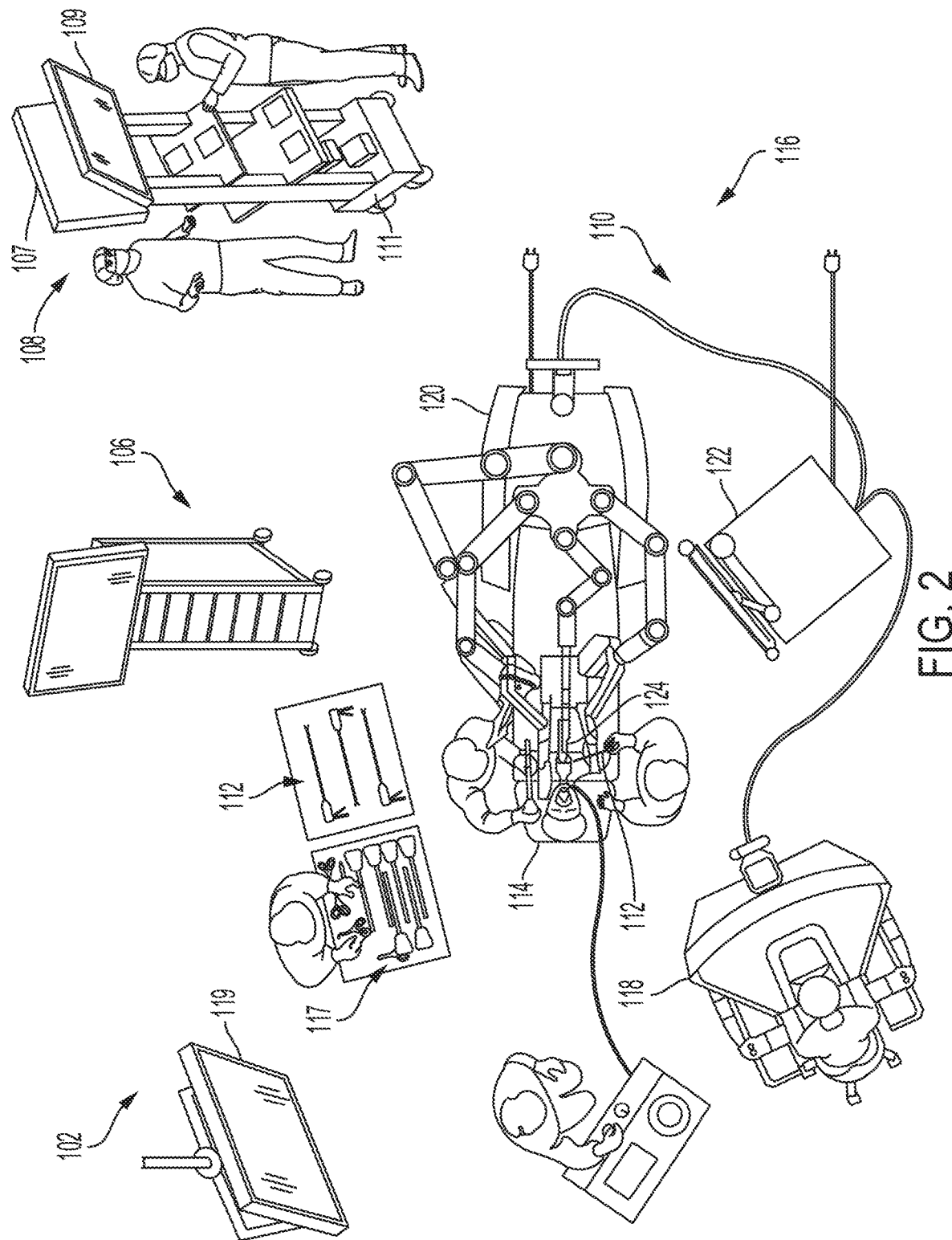
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
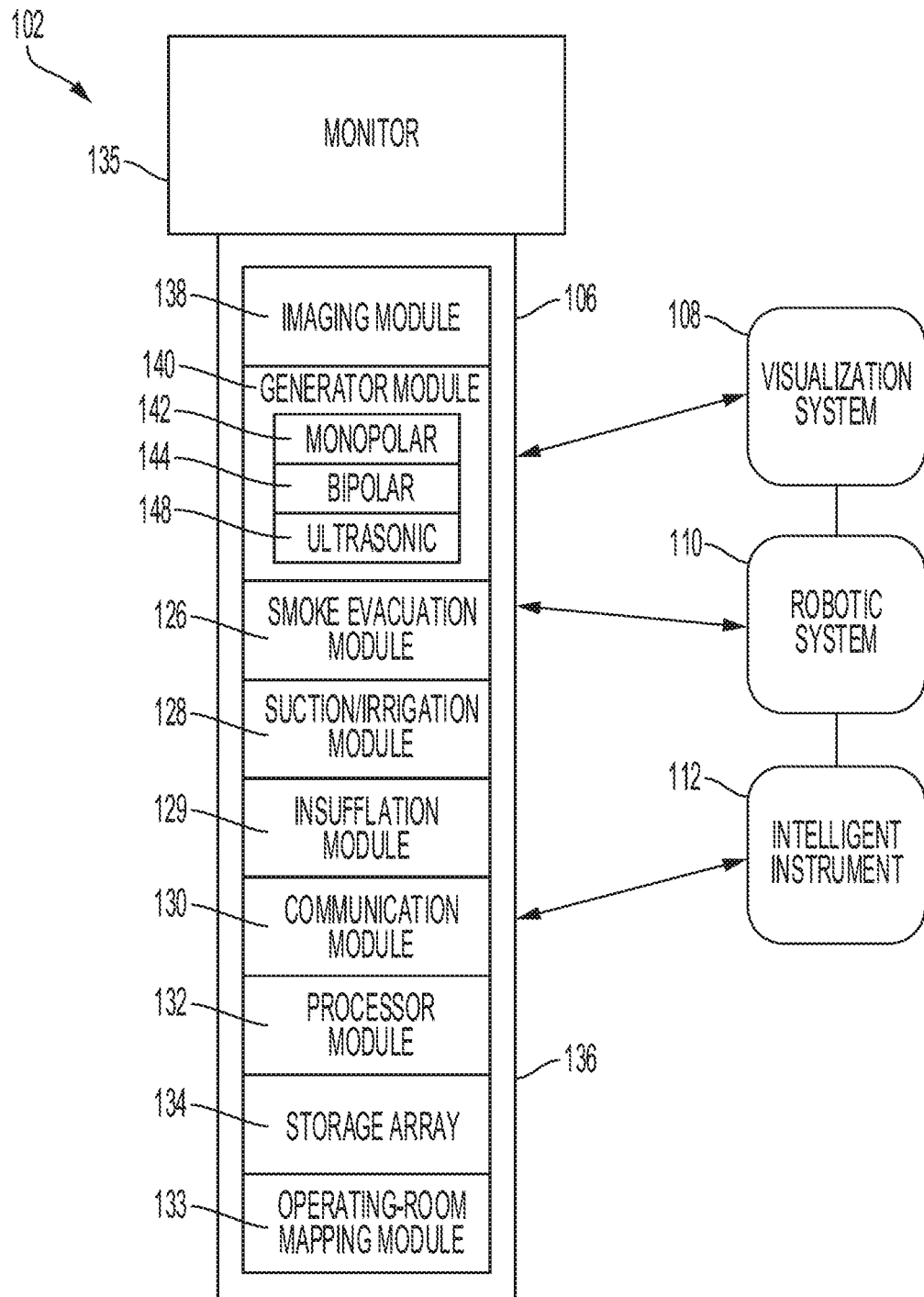
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analogto-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
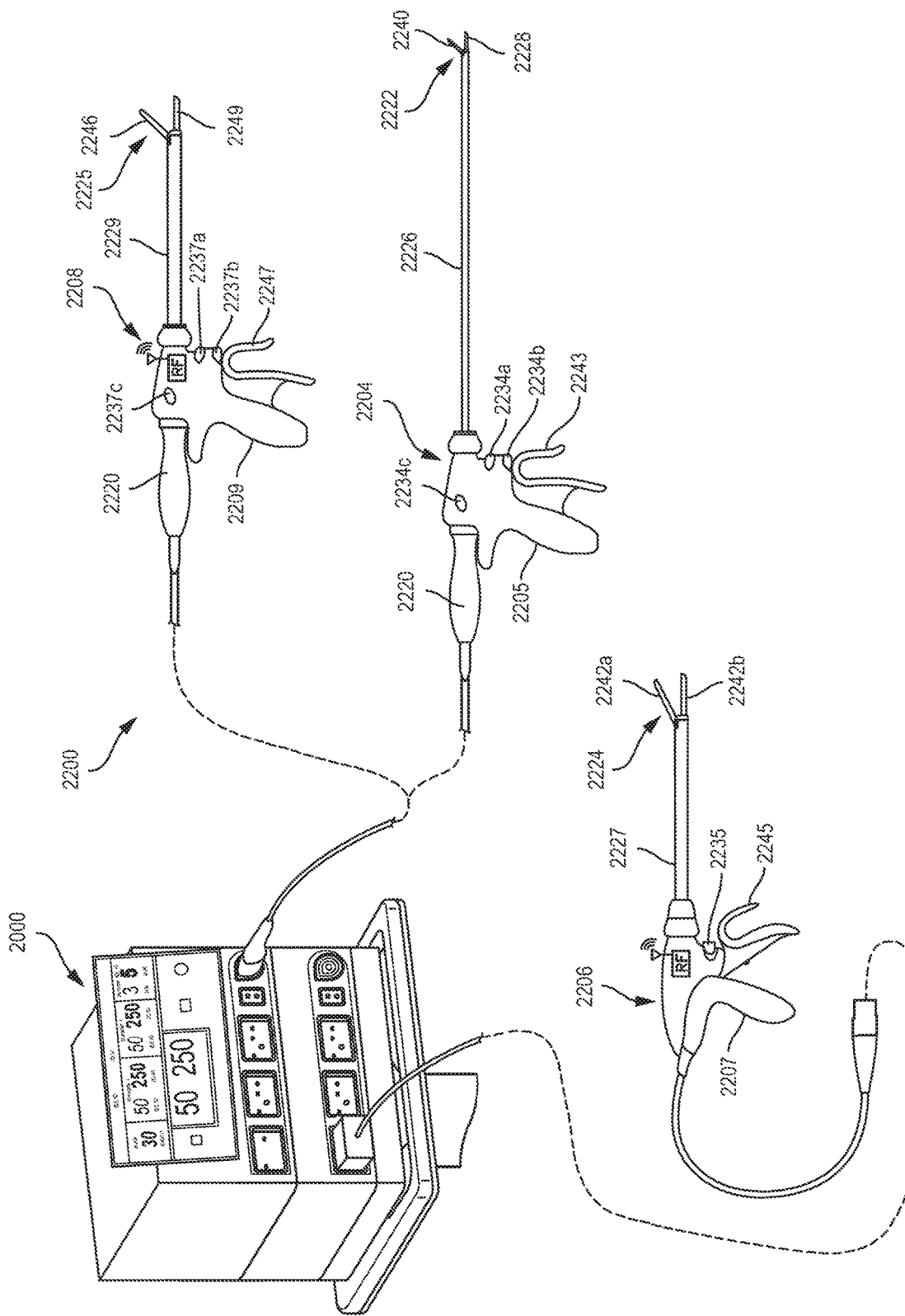
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in US patent publication US-2017-0086914-A1, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 5:
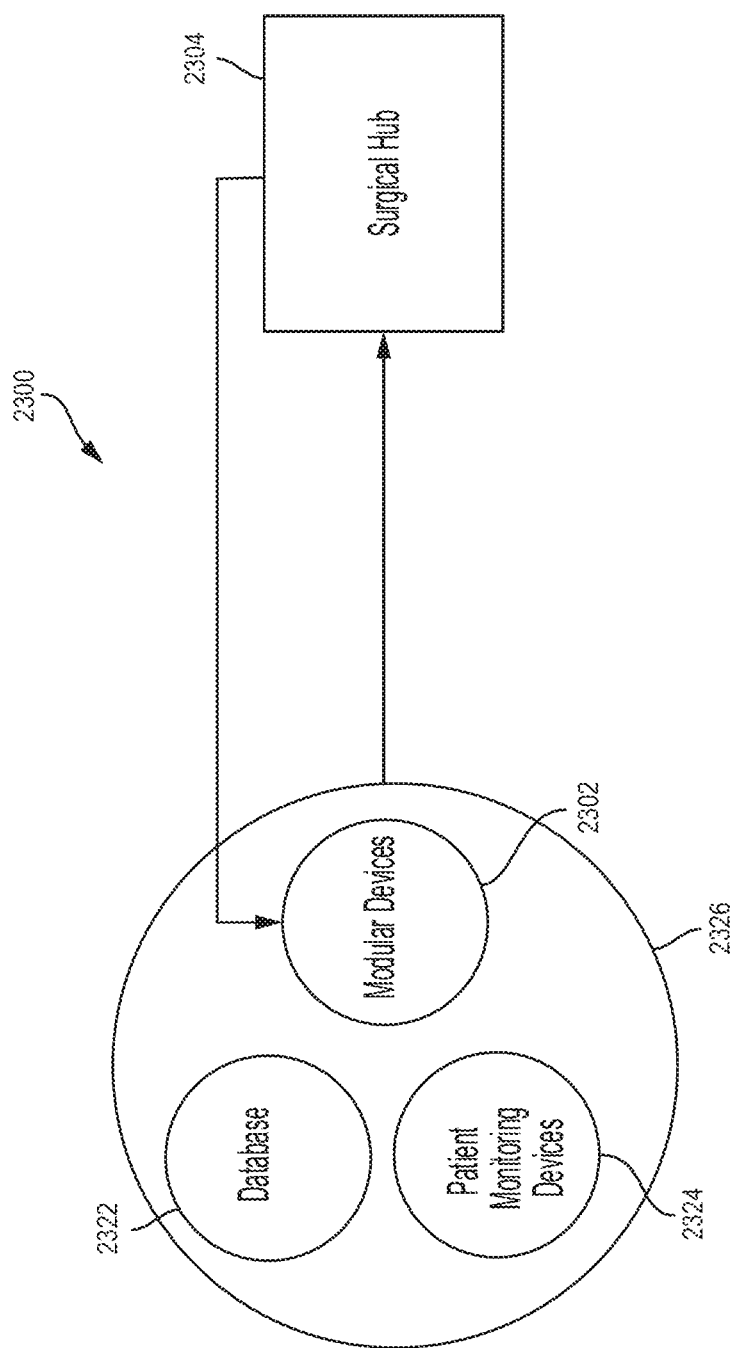
FIG. 5 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 5 illustrates a diagram of a situationally aware surgical system 2300, in accordance with at least one aspect of the present disclosure. In some exemplifications, the data sources 2326 include, for example, the modular devices 2302 (which can include sensors configured to detect parameters associated with the patient and/or the modular device itself), databases 2322 (e.g., an EMR database containing patient records), and patient monitoring devices 2324 (e.g., a blood pressure (BP) monitor and an electrocardiography (EKG) monitor). The surgical hub 2304 can be configured to derive the contextual information pertaining to the surgical procedure from the data based upon, for example, the particular combination(s) of received data or the particular order in which the data is received from the data sources 2326. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2304 to derive or infer information related to the surgical procedure from received data can be referred to as "situational awareness." In one exemplification, the surgical hub 2304 can incorporate a situational awareness system, which is the hardware and/or programming associated with the surgical hub 2304 that derives contextual information pertaining to the surgical procedure from the received data.

The situational awareness system of the surgical hub 2304 can be configured to derive the contextual information from the data received from the data sources 2326 in a variety of different ways. In one exemplification, the situational awareness system includes a pattern recognition system, or machine learning system (e.g., an artificial neural network), that has been trained on training data to correlate various inputs (e.g., data from databases 2322, patient monitoring devices 2324, and/or modular devices 2302) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2302. In one exemplification, the contextual information received by the situational awareness system of the surgical hub 2304 is associated with a particular control adjustment or set of control adjustments for one or more modular devices 2302. In another exemplification, the situational awareness system includes a further machine learning system, lookup table, or other such system, which generates or retrieves one or more control adjustments for one or more modular devices 2302 when provided the contextual information as input.

A surgical hub 2304 incorporating a situational awareness system provides a number of benefits for the surgical system 2300. One benefit includes improving the interpretation of sensed and collected data, which would in turn improve the processing accuracy and/or the usage of the data during the course of a surgical procedure. To return to a previous example, a situationally aware surgical hub 2304 could determine what type of tissue was being operated on; therefore, when an unexpectedly high force to close the surgical instrument's end effector is detected, the situationally aware surgical hub 2304 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2304 could infer whether a surgical procedure being performed is a thoracic or an abdominal procedure, allowing the surgical hub 2304 to determine whether the tissue clamped by an end effector of the surgical stapling and cutting instrument is lung (for a thoracic procedure) or stomach (for an abdominal procedure) tissue. The surgical hub 2304 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2304 could determine whether the surgical site is under pressure (by determining that the surgical procedure is utilizing insufflation) and determine the procedure type. As a procedure type is generally performed in a specific body cavity, the surgical hub 2304 could then control the motor rate of the smoke evacuator appropriately for the body cavity being operated in. Thus, a situationally aware surgical hub 2304 could provide a consistent amount of smoke evacuation for both thoracic and abdominal procedures.

As yet another example, the type of procedure being performed can affect the optimal energy level at which an ultrasonic surgical instrument or radio frequency (RF) electrosurgical instrument operates. Arthroscopic procedures, for example, require higher energy levels because the end effector of the ultrasonic surgical instrument or RF electrosurgical instrument is immersed in fluid. A situationally aware surgical hub 2304 could determine whether the surgical procedure is an arthroscopic procedure. The surgical hub 2304 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2304 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2304 can be configured to adjust the energy level for the ultrasonic surgical instrument or RF electrosurgical instrument throughout the course of a surgical procedure, rather than just on a procedure-by-procedure basis. A situationally aware surgical hub 2304 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2326 to improve the conclusions that the surgical hub 2304 draws from one data source 2326. A situationally aware surgical hub 2304 could augment data that it receives from the modular devices 2302 with contextual information that it has built up regarding the surgical procedure from other data sources 2326. For example, a situationally aware surgical hub 2304 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2304 can be further configured to compare a physiologic measurement (e.g., blood pressure sensed by a BP monitor communicably connected to the surgical hub 2304) with the visual or image data of hemostasis (e.g., from a medical imaging device 124 (FIG. 2) communicably coupled to the surgical hub 2304) to make a determination on the integrity of the staple line or tissue weld. In other words, the situational awareness system of the surgical hub 2304 can consider the physiological measurement data to provide additional context in analyzing the visualization data. The additional context can be useful when the visualization data may be inconclusive or incomplete on its own.

Another benefit includes proactively and automatically controlling the paired modular devices 2302 according to the particular step of the surgical procedure that is being performed to reduce the number of times that medical personnel are required to interact with or control the surgical system 2300 during the course of a surgical procedure. For example, a situationally aware surgical hub 2304 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2304 could determine whether the current or subsequent step of the surgical procedure requires a different view or degree of magnification on the display according to the feature(s) at the surgical site that the surgeon is expected to need to view. The surgical hub 2304 could then proactively change the displayed view (supplied by, e.g., a medical imaging device for the visualization system 108) accordingly so that the display automatically adjusts throughout the surgical procedure.

As yet another example, a situationally aware surgical hub 2304 could determine which step of the surgical procedure is being performed or will subsequently be performed and whether particular data or comparisons between data will be required for that step of the surgical procedure. The surgical hub 2304 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2304 could determine whether the operating theater is setup properly or optimally for the surgical procedure to be performed. The surgical hub 2304 can be configured to determine the type of surgical procedure being performed, retrieve the corresponding checklists, product location, or setup needs (e.g., from a memory), and then compare the current operating theater layout to the standard layout for the type of surgical procedure that the surgical hub 2304 determines is being performed. In one exemplification, the surgical hub 2304 can be configured to compare the list of items for the procedure (scanned by a scanner, for example) and/or a list of devices paired with the surgical hub 2304 to a recommended or anticipated manifest of items and/or devices for the given surgical procedure. If there are any discontinuities between the lists, the surgical hub 2304 can be configured to provide an alert indicating that a particular modular device 2302, patient monitoring device 2324, and/or other surgical item is missing. In one exemplification, the surgical hub 2304 can be configured to determine the relative distance or position of the modular devices 2302 and patient monitoring devices 2324 via proximity sensors, for example. The surgical hub 2304 can compare the relative positions of the devices to a recommended or anticipated layout for the particular surgical procedure. If there are any discontinuities between the layouts, the surgical hub 2304 can be configured to provide an alert indicating that the current layout for the surgical procedure deviates from the recommended layout.

As another example, a situationally aware surgical hub 2304 could determine whether the surgeon (or other medical personnel) was making an error or otherwise deviating from the expected course of action during the course of a surgical procedure. For example, the surgical hub 2304 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2304 determined is being performed. In one exemplification, the surgical hub 2304 can be configured to provide an alert indicating that an unexpected action is being performed or an unexpected device is being utilized at the particular step in the surgical procedure.

Overall, the situational awareness system for the surgical hub 2304 improves surgical procedure outcomes by adjusting the surgical instruments (and other modular devices 2302) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2302 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 6:
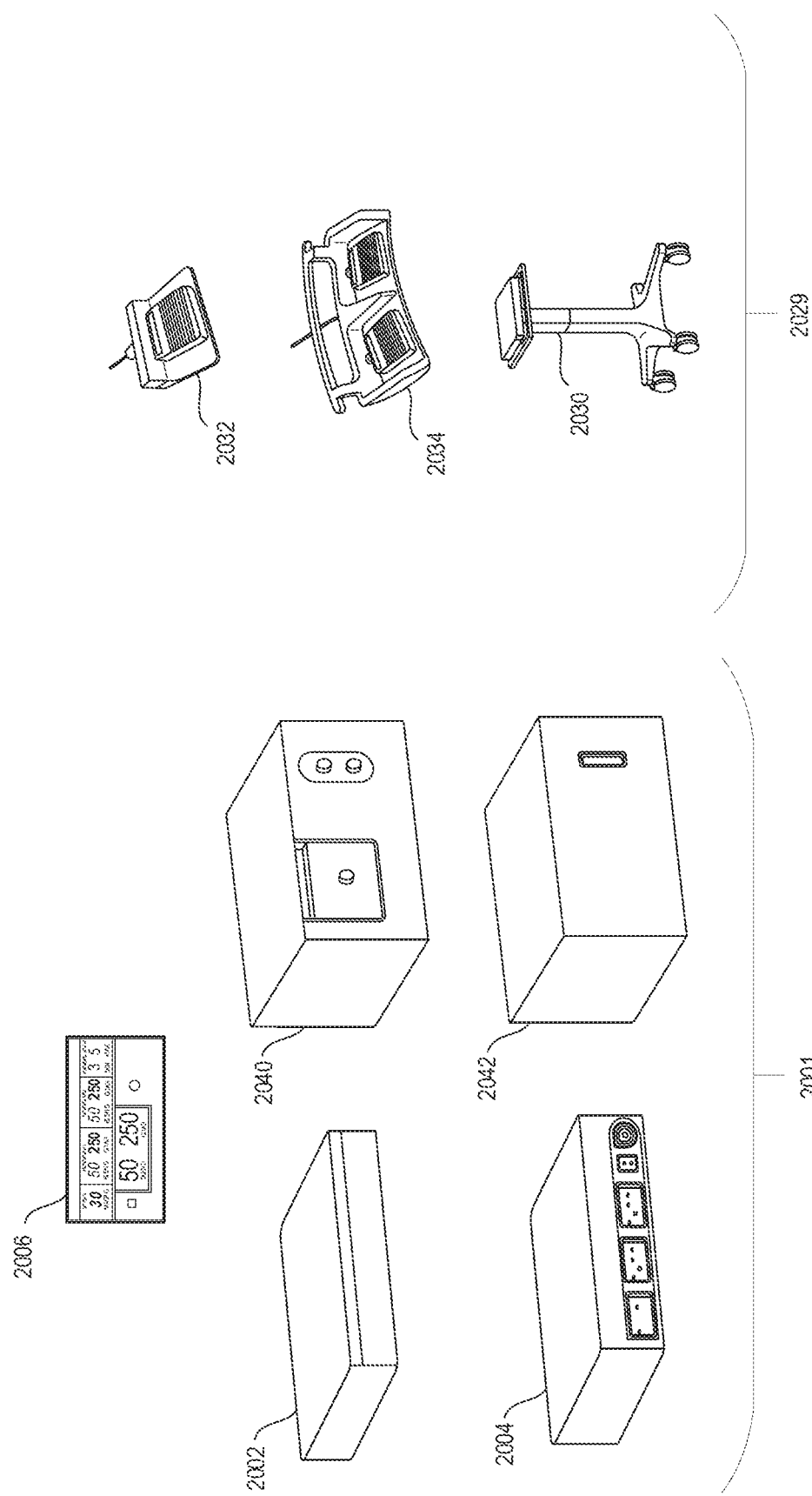
FIG. 6 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 6. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 7B:
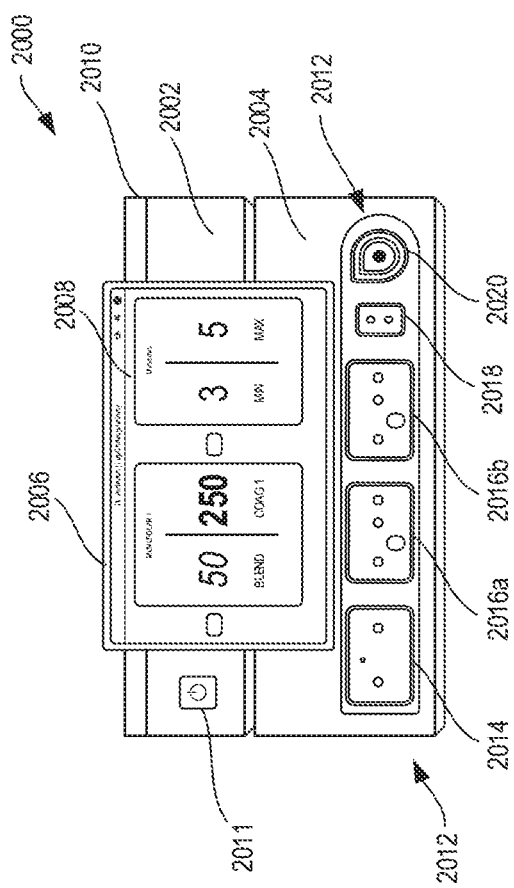
FIG. 7B is the modular energy system shown in FIG. 7A mounted to a cart, in accordance with at least one aspect of the present disclosure.
Figure 7A:
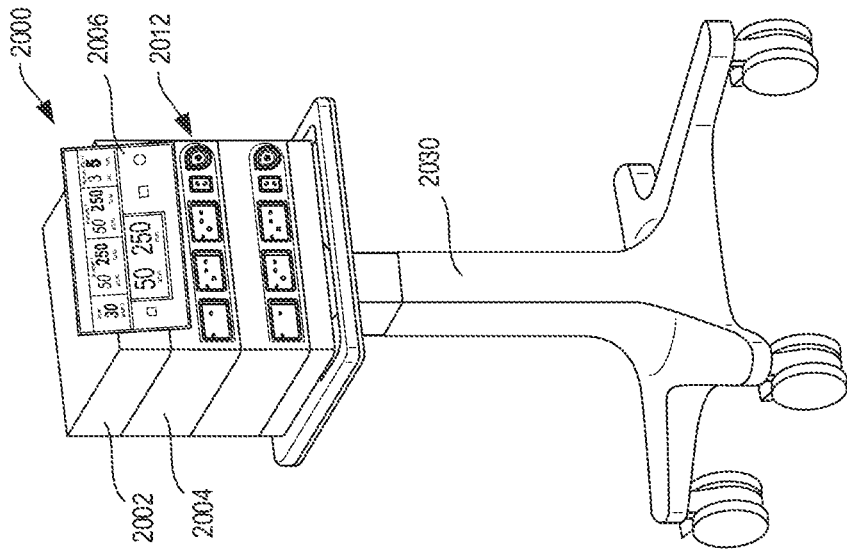
FIG. 7A is a first illustrative modular energy system configuration including a header module and a display screen that renders a graphical user interface (GUI) for relaying information regarding modules connected to the header module, in accordance with at least one aspect of the present disclosure.
Figure 11:
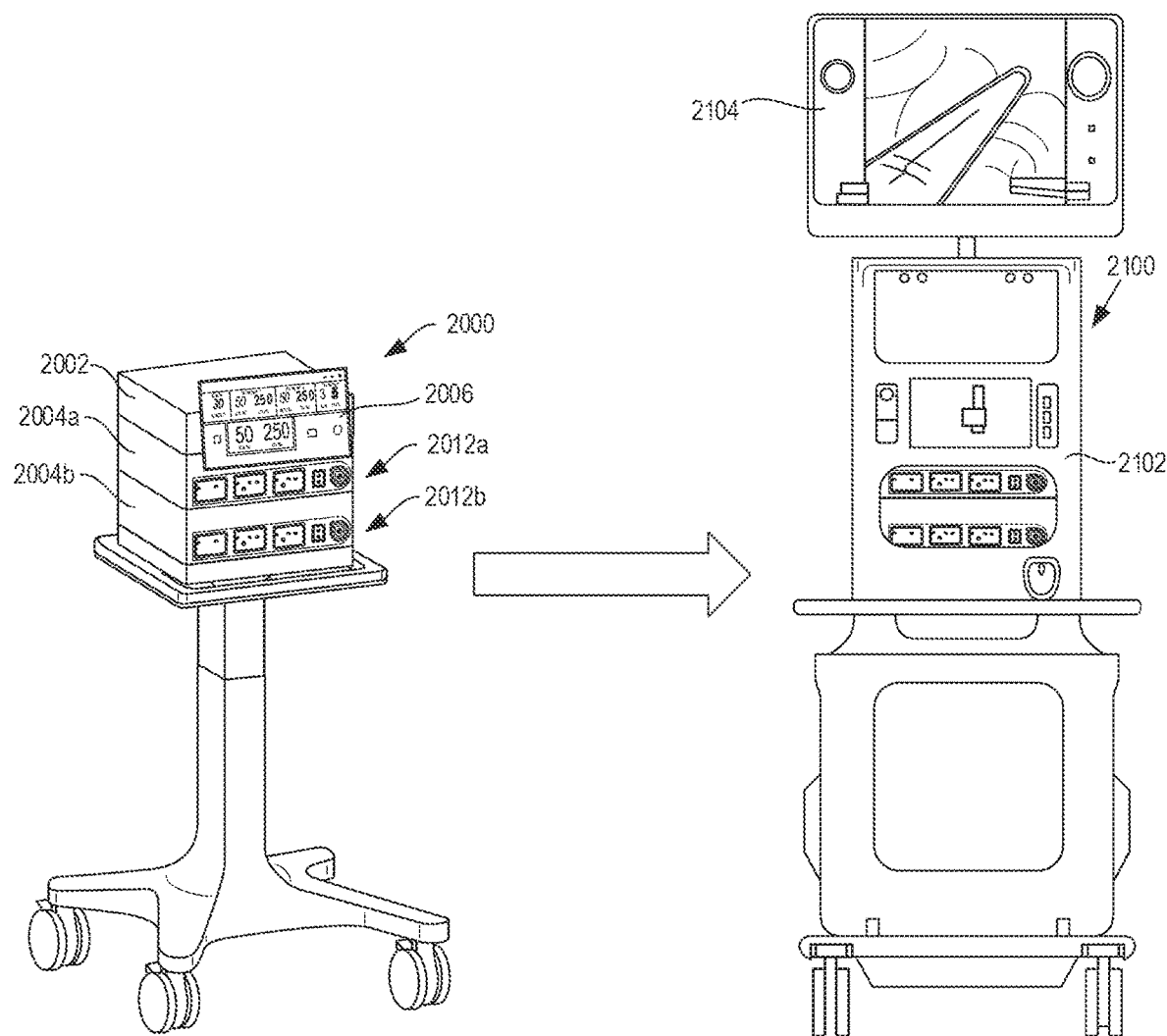
FIG. 11 is a diagram of a modular energy system including communicably connectable surgical platforms, in accordance with at least one aspect of the present disclosure.

Referring now to FIG. 7A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 12. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 11. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 7A, the energy module 2004 can include a port assembly 2012 including a number of different ports configured to deliver different energy modalities to corresponding surgical instruments that are connectable thereto. In the particular aspect illustrated in FIGS. 6-12, the port assembly 2012 includes a bipolar port 2014, a first monopolar port 2016a, a second monopolar port 2016b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 7A and 7B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 8A:
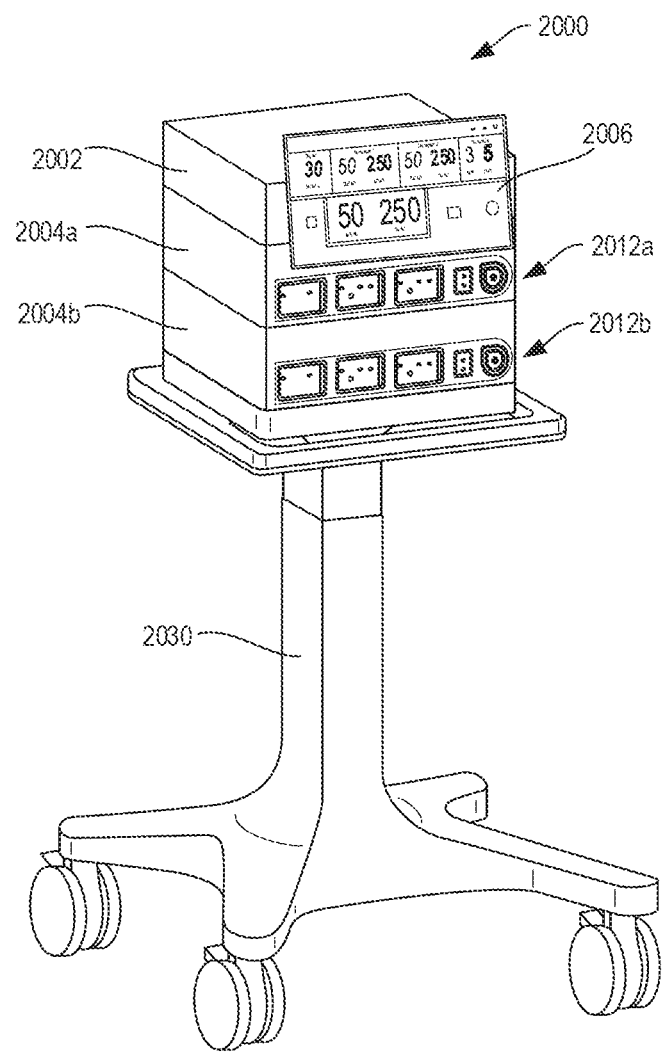
FIG. 8A is a second illustrative modular energy system configuration including a header module, a display screen, an energy module, and an expanded energy module connected together and mounted to a cart, in accordance with at least one aspect of the present disclosure.
Figure 8B:
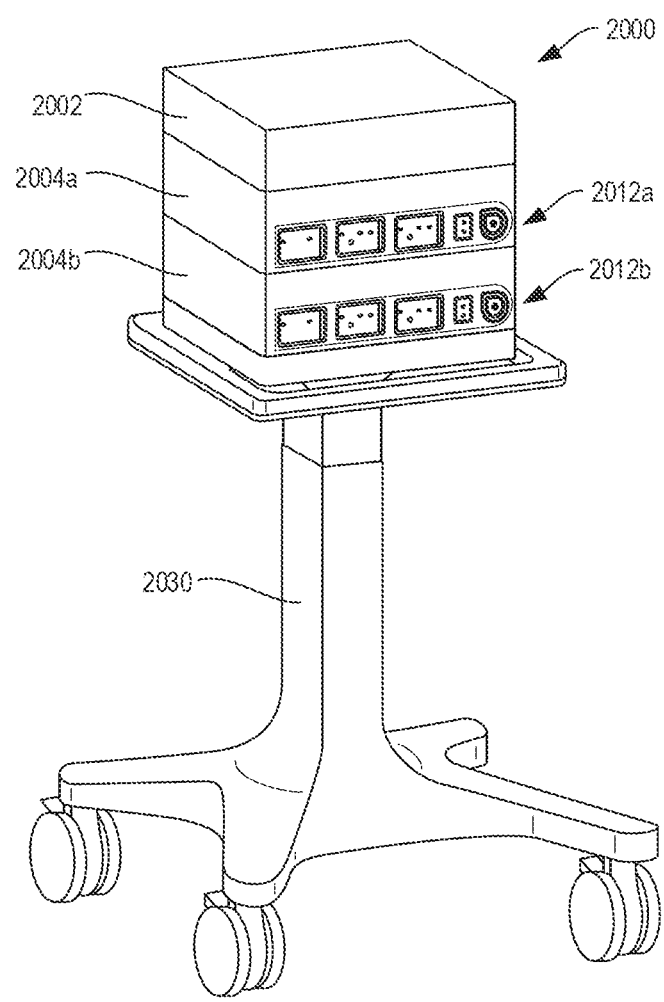
FIG. 8B is a third illustrative modular energy system configuration that is similar to the second configuration shown in FIG. 7A, except that the header module lacks a display screen, in accordance with at least one aspect of the present disclosure.

FIG. 8A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 8B illustrates a third illustrative configuration that is similar to the second configuration, except that the header module 2002 lacks a display screen 2006. This configuration can be suitable for robotic surgical applications or mobile display applications, as noted above.

Figure 9:
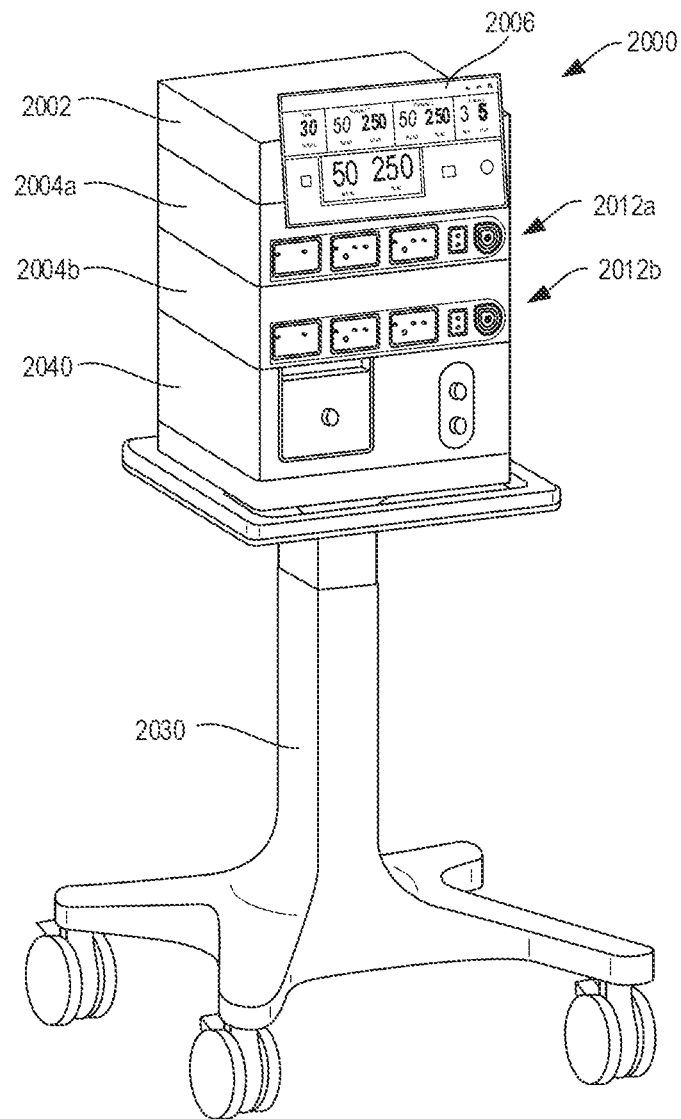
FIG. 9 is a fourth illustrative modular energy system configuration including a header module, a display screen, an energy module, ae expanded energy module, and a technology module connected together and mounted to a cart, in accordance with at least one aspect of the present disclosure.

FIG. 9 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 10:
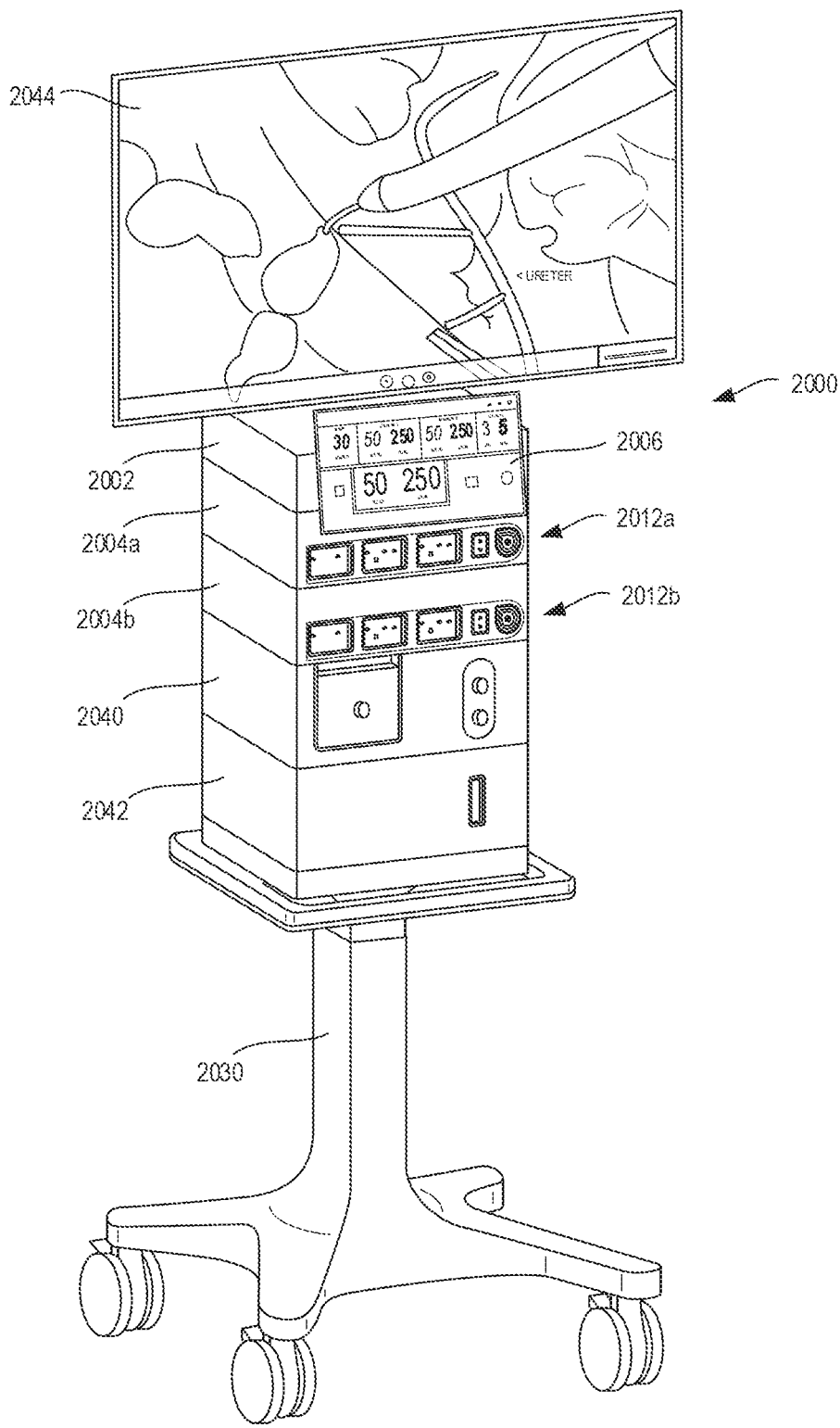
FIG. 10 is a fifth illustrative modular energy system configuration including a header module, a display screen, an energy module, an expanded energy module, a technology module, and a visualization module connected together and mounted to a cart, in accordance with at least one aspect of the present disclosure.

FIG. 10 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 7A-11 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 11. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 12:
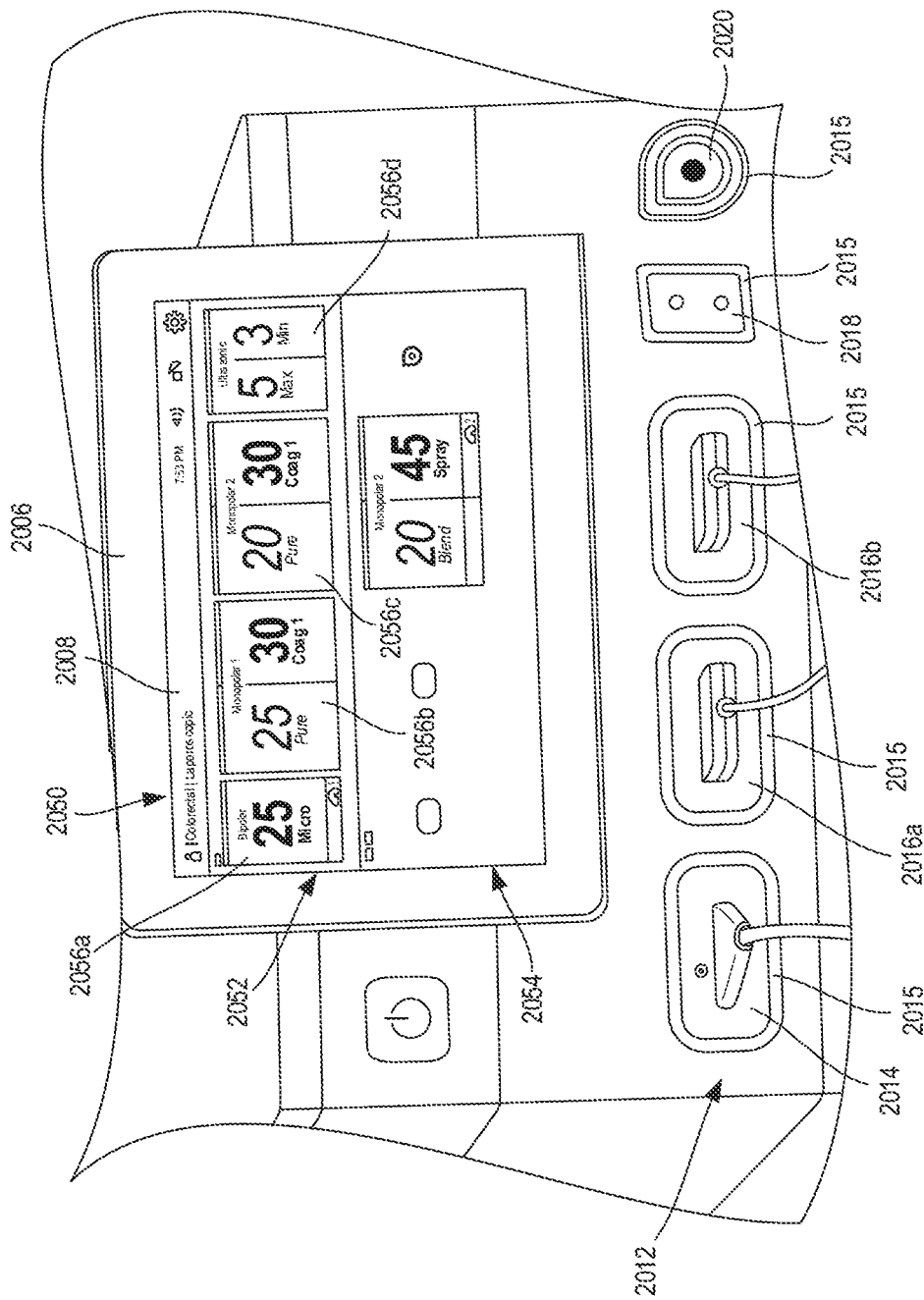
FIG. 12 is a perspective view of a header module of a modular energy system including a user interface, in accordance with at least one aspect of the present disclosure.

Referring now to FIG. 12, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056*a* corresponding to the bipolar port 2014, a second widget 2056*b* corresponding to the first monopolar port 2016*a*, a third widget 2056*c* corresponding to the second monopolar port 2016*b*, and a fourth widget 2056*d* corresponding to the combination energy port 2020. Each of these widgets 2056*a-d* provides data related to its corresponding port of the port assembly 2012 and controls for controlling the modes and other features of the energy modality delivered by the energy module 2004 through the respective port of the port assembly 2012. For example, the widgets 2056*a-d* can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 13:
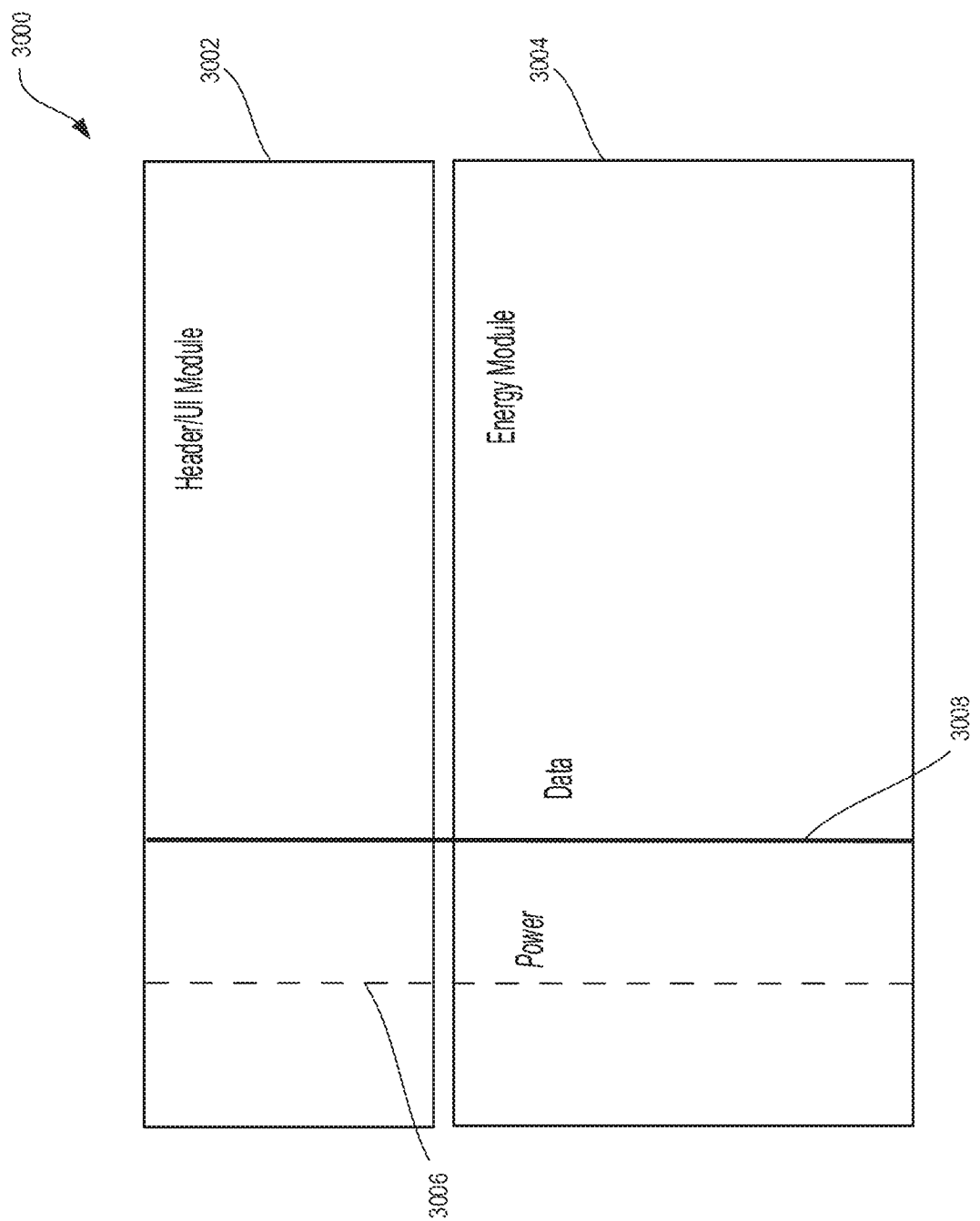
FIG. 13 is a block diagram of a stand-alone hub configuration of a modular energy system, in accordance with at least one aspect of the present disclosure.
Figure 14:
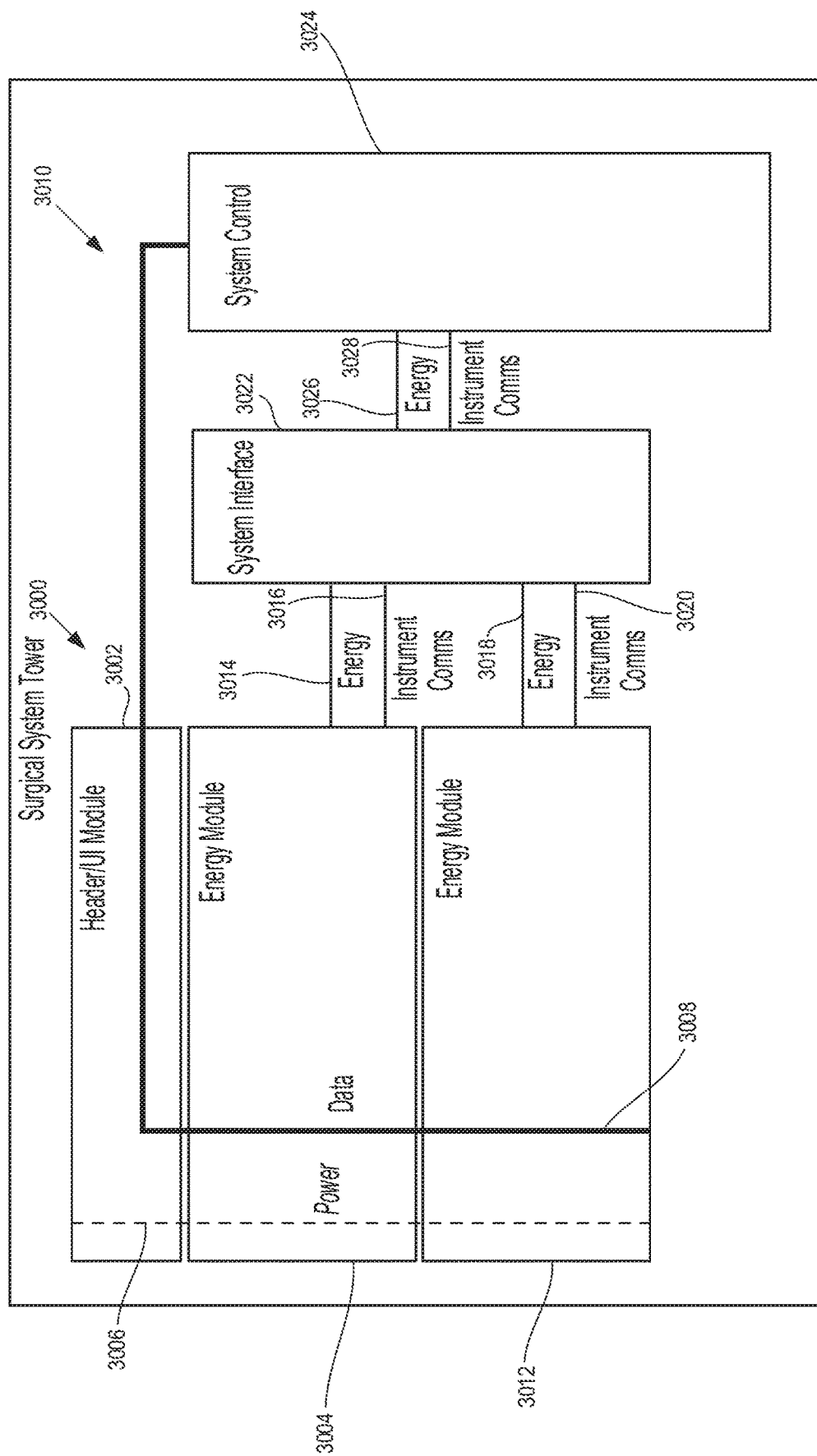
FIG. 14 is a block diagram of a hub configuration of a modular energy system integrated with a surgical control system, in accordance with at least one aspect of the present disclosure.

FIG. 13 is a block diagram of a stand-alone hub configuration of a modular energy system 3000, in accordance with at least one aspect of the present disclosure and FIG. 14 is a block diagram of a hub configuration of a modular energy system 3000 integrated with a surgical control system 3010, in accordance with at least one aspect of the present disclosure. As depicted in FIGS. 13 and 14, the modular energy system 3000 can be either utilized as stand-alone units or integrated with a surgical control system 3010 that controls and/or receives data from one or more surgical hub units. In the examples illustrated in FIGS. 13 and 14, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 14, a surgical hub configuration includes a modular energy system 3000 integrated with a control system 3010 and an interface system 3022 for managing, among other things, data and power transmission to and/or from the modular energy system 3000. The modular energy system depicted in FIG. 14 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 15:
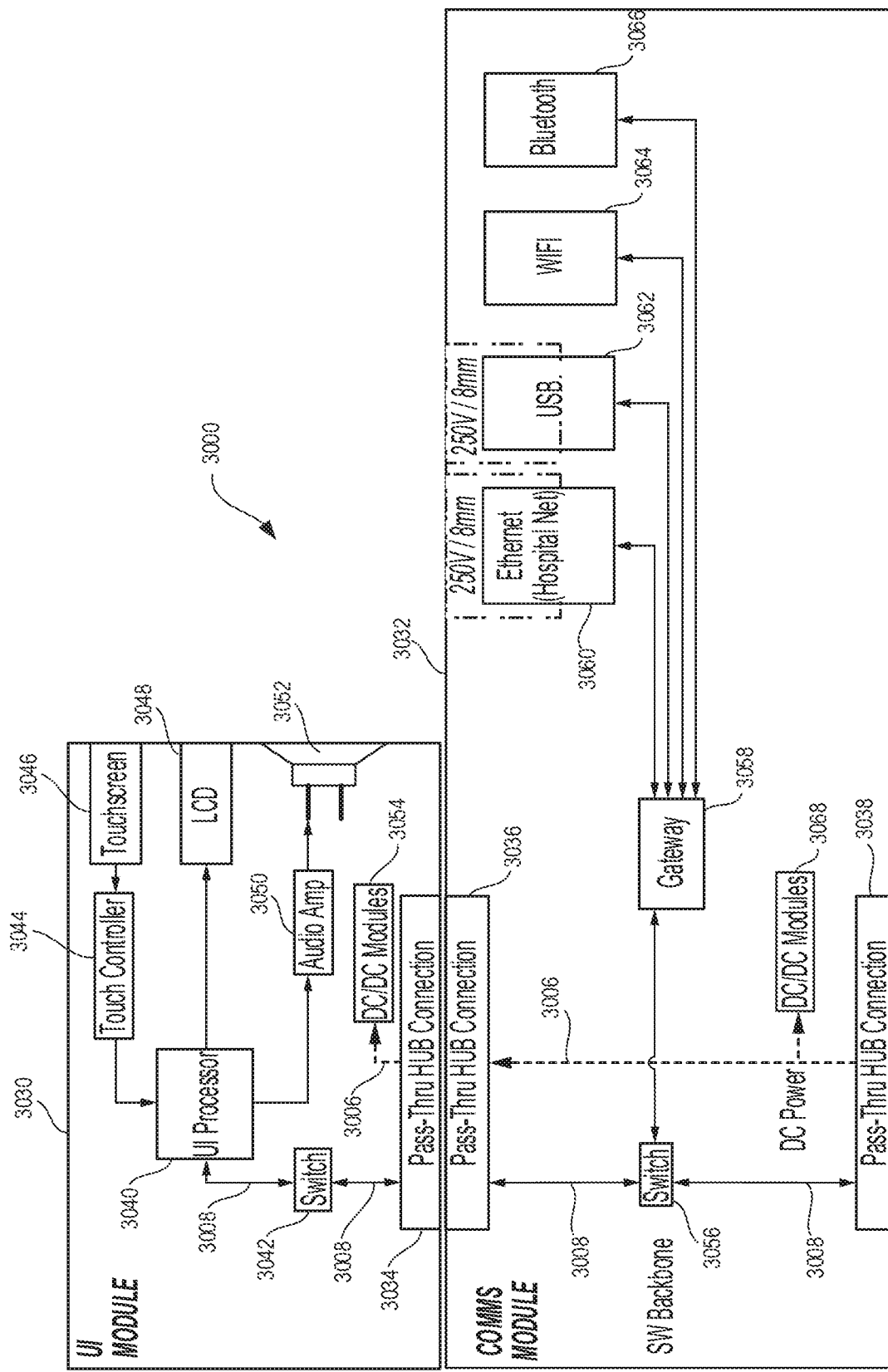
FIG. 15 is a block diagram of a user interface module coupled to a communications module of a modular energy system, in accordance with at least one aspect of the present disclosure.
Figure 16:
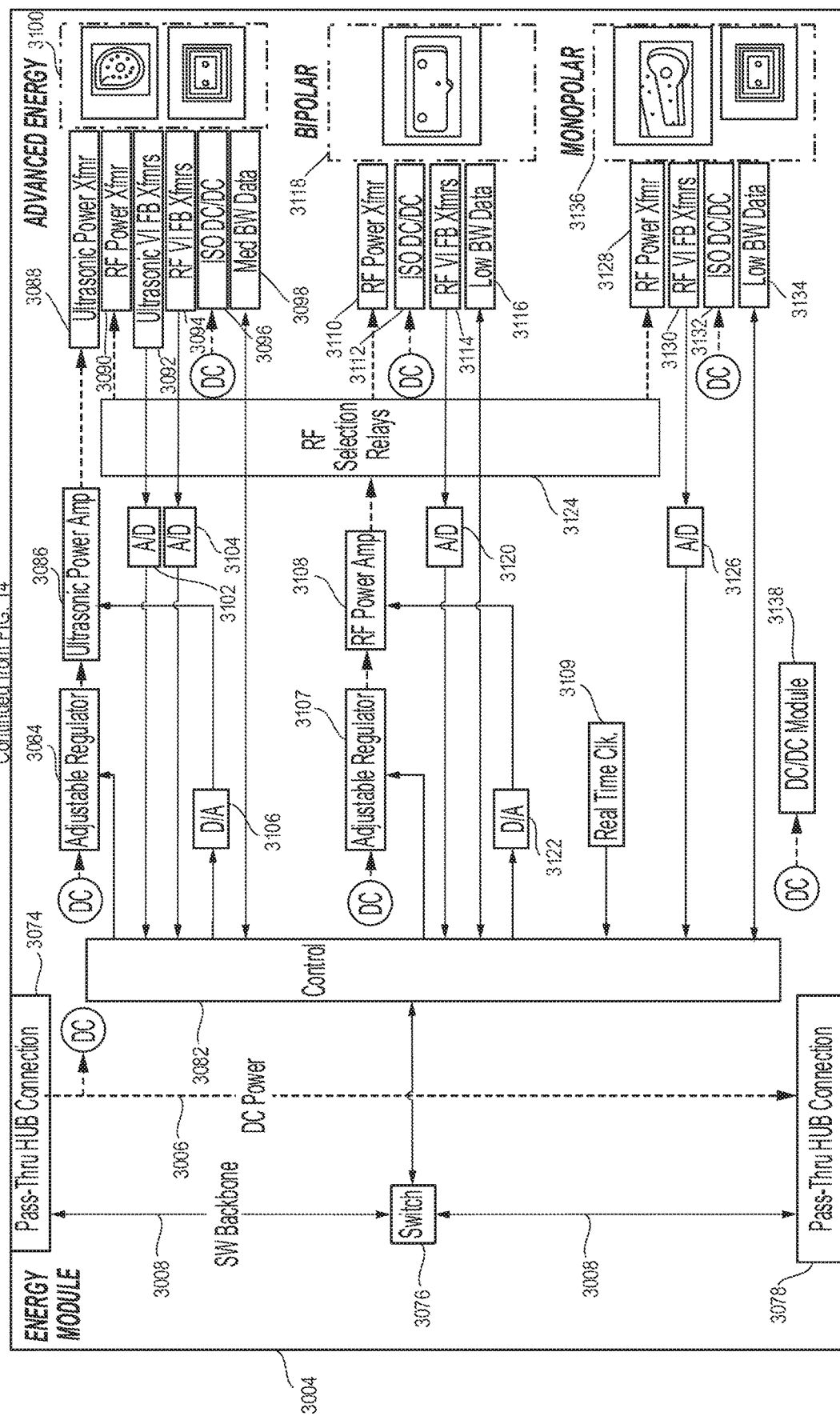
FIG. 16 is a block diagram of an energy module of a modular energy system, in accordance with at least one aspect of the present disclosure.
Figure 17A:
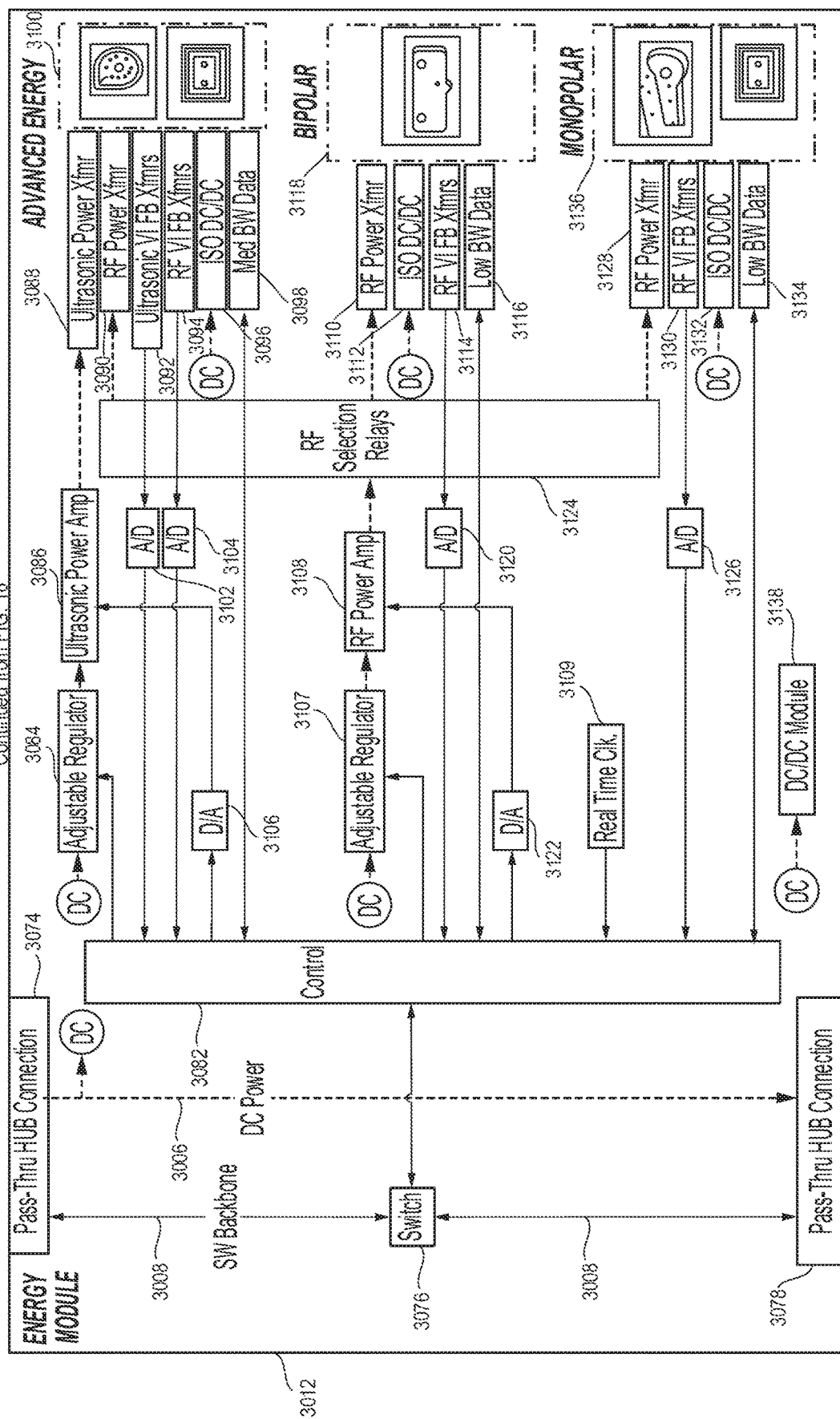
FIGS. 17A and 17B illustrate a block diagram of an energy module coupled to a header module of a modular energy system, in accordance with at least one aspect of the present disclosure.
Figure 17B:
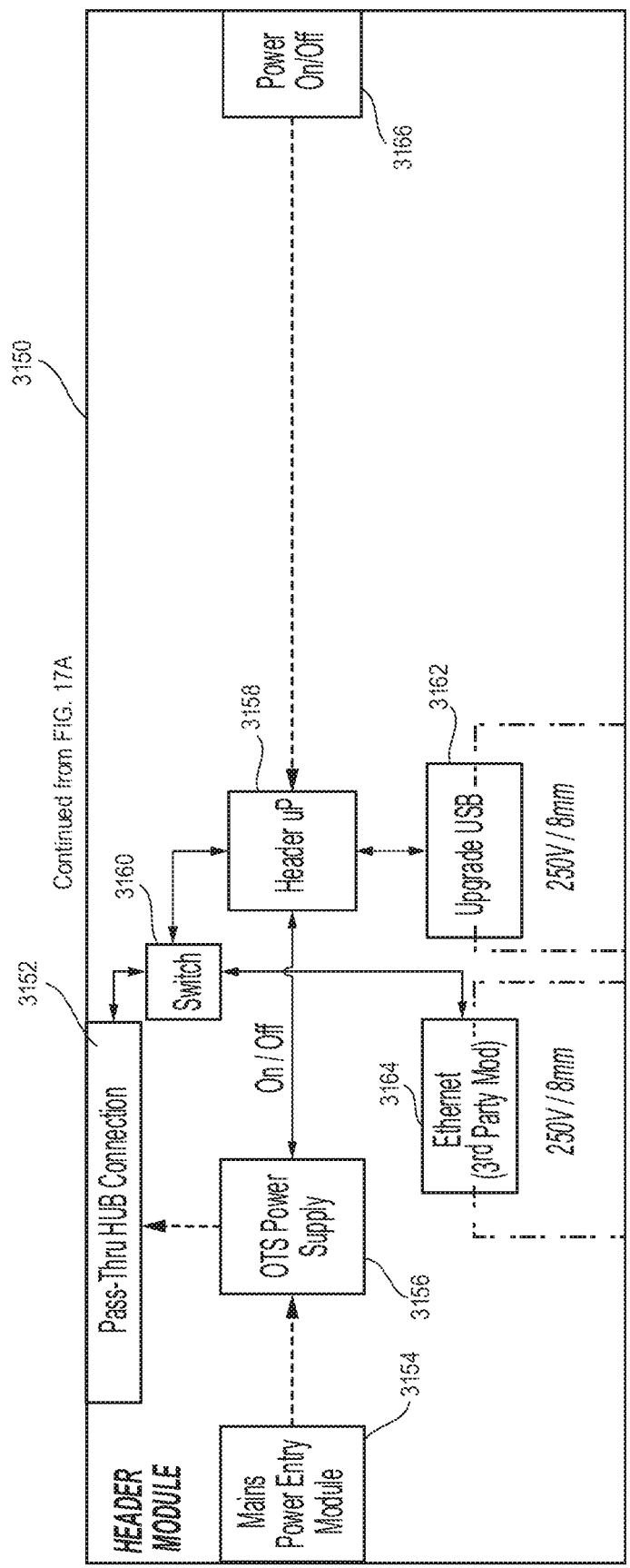

FIGS. 15-17 are block diagrams of various modular energy systems connected together to form a hub, in accordance with at least one aspect of the present disclosure. FIGS. 15-17 depict various diagrams (e.g., circuit or control diagrams) of hub modules. The modular energy system 3000 includes multiple energy modules 3004 (FIG. 16), 3012 (FIG. 17), a header module 3150 (FIG. 17), a UI module 3030 (FIG. 15), and a communications module 3032 (FIG. 15), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 15, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 17) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 15, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WiFi module 3064, and a Bluetooth module 3066, among others. The communications modules may be physical boards located within the communications module 3032 or may be a port to couple to remote communications boards.

Figure 18A:
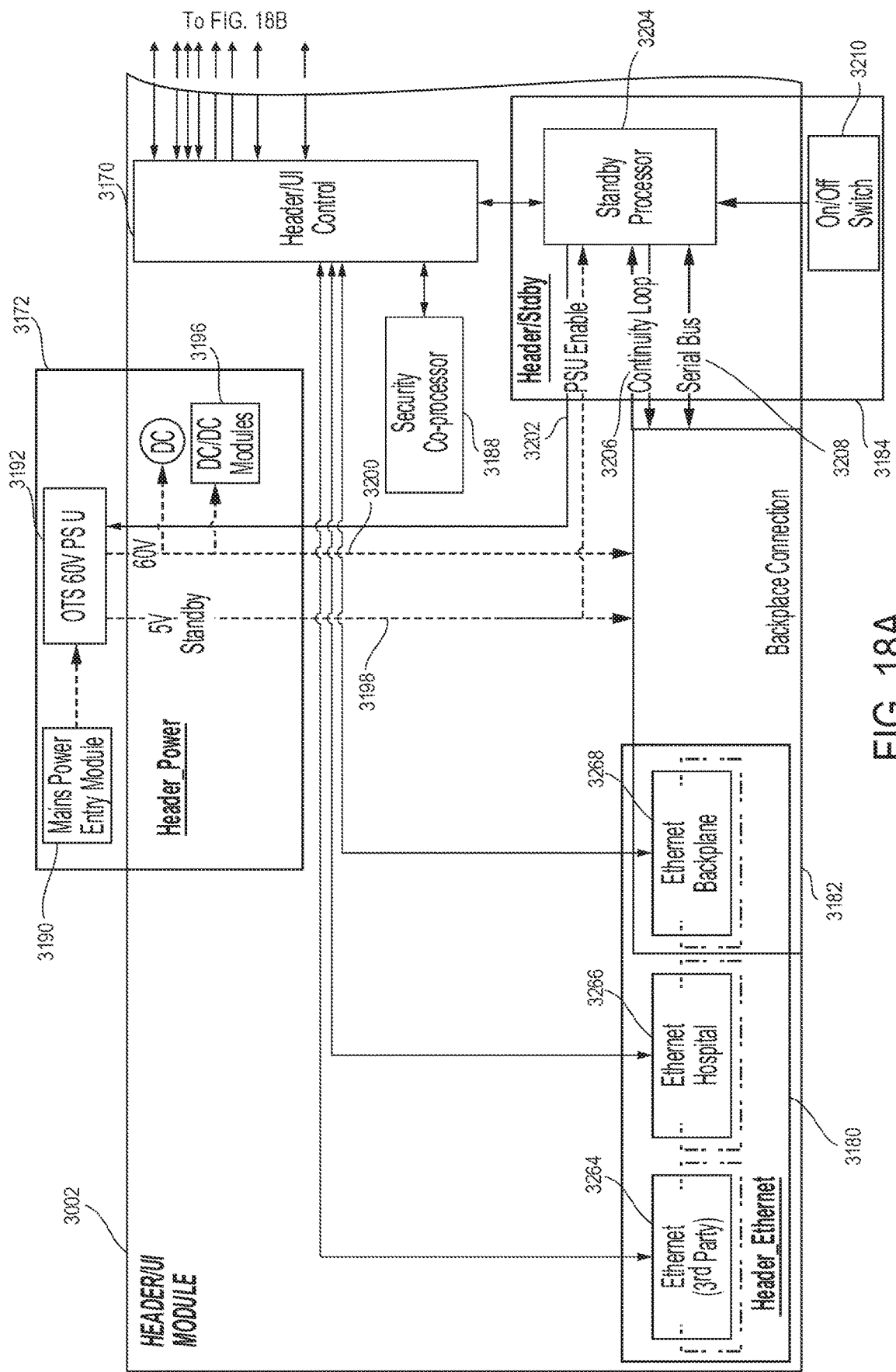
FIGS. 18A and 18B illustrate a block diagram of a header/user interface (UI) module of a modular energy system for a hub, such as the header module depicted in FIG. 15, in accordance with at least one aspect of the present disclosure.
Figure 18B:
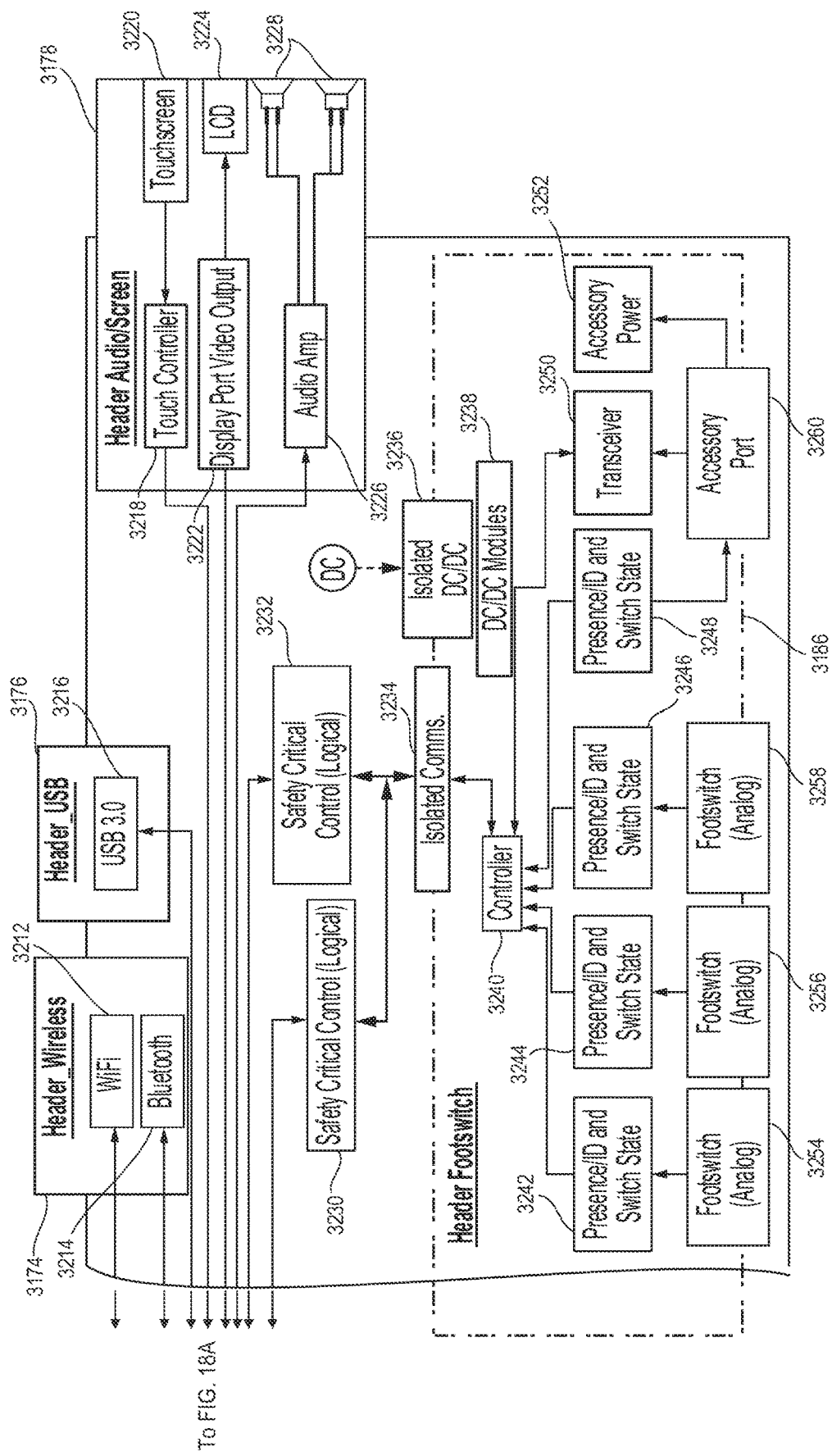

In some aspects, all of the modules (i.e., detachable hardware) are controlled by a single UI module 3030 that is disposed on or integral to a header module. FIG. 17 shows a stand alone header module 3150 to which the UI module 3030 can be attached. FIGS. 13, 14, and 18 show an integrated header/UI Module 3002. Returning now to FIG. 15, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 16, there is shown a block diagram of an energy module 3004, in accordance with at least one aspect of the present disclosure. The communications module 3032 (FIG. 15) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 17, via a second pass-through hub connector 3078. Turning back to FIG. 16, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 17 is a block diagram of a second energy module 3012 coupled to a header module 3150, in accordance with at least one aspect of the present disclosure. The first energy module 3004 shown in FIG. 16 is coupled to the second energy module 3012 shown in FIG. 17 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 17. In another aspect, the second energy module 2012 can be a different energy module compared to the first energy module, such as an energy module illustrated in FIG. 19, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 18 is a block diagram of a header/user interface (UI) module 3002 for a hub, such as the header module depicted in FIG. 15, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security coprocessor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WiFi module 3212 and a Bluetooth module 3214. Both the WiFi module 3212 and the Bluetooth module 3214 are coupled to the header/UI controller 3170. The Bluetooth module 3214 is used to connect devices without using cables and the WiFi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument (s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 19:
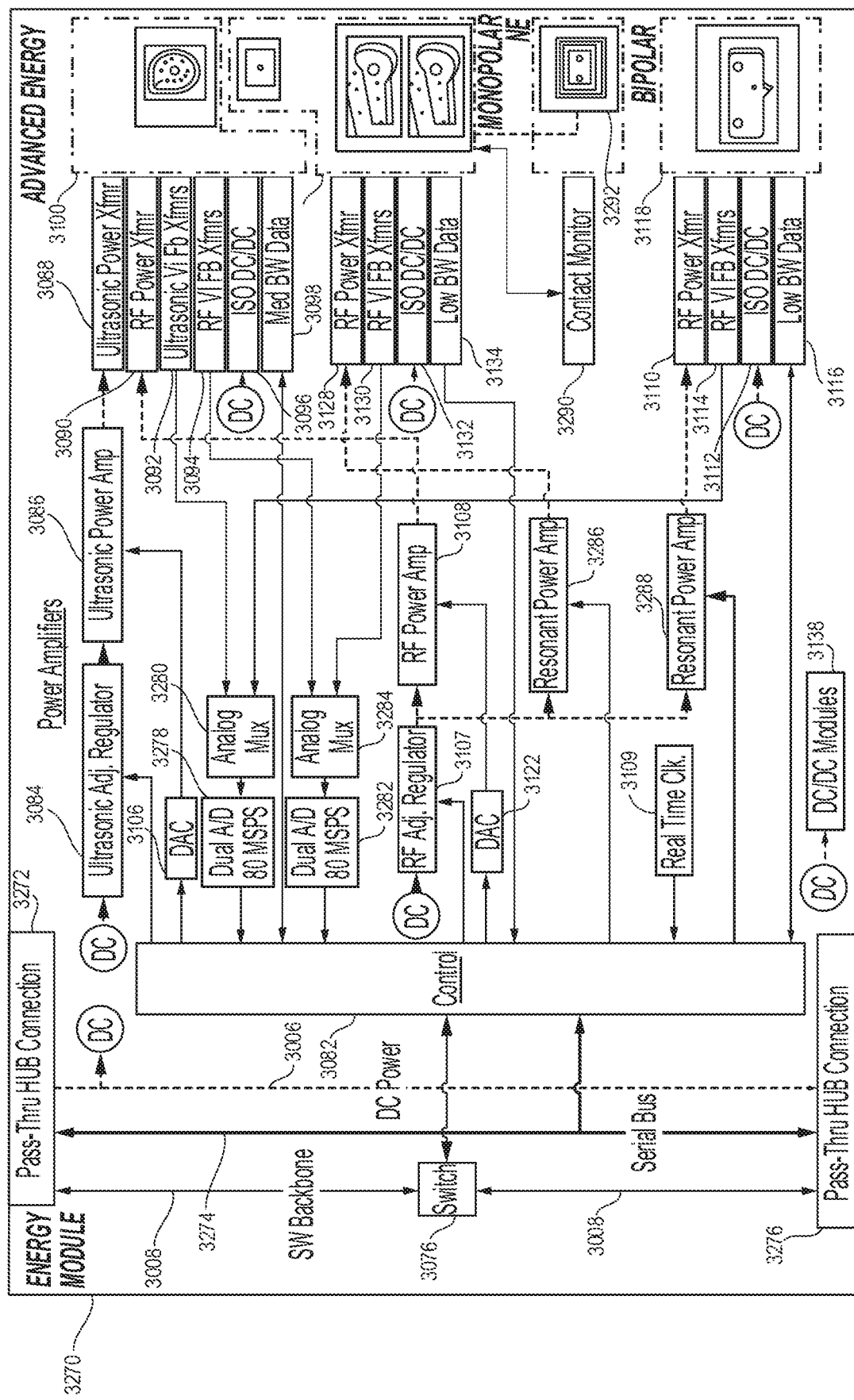
FIG. 19 is a block diagram of an energy module for a hub, such as the energy module depicted in FIGS. 13-18B, in accordance with at least one aspect of the present disclosure.

FIG. 19 is a block diagram of an energy module 3270 for a hub, such as the energy module depicted in FIGS. 13, 14, 16, and 17, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (A/D). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 16 and 17, the energy module 3270 does not include RF selection relays configured to receive an RF output signal from the adjustable buck regulator 3107. In addition, unlike the energy modules 3004, 3012 shown and described in FIGS. 16 and 17, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual A/D 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual A/D 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 13-19, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 13-19, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 13-19, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected and set to a high impedance state.

In one aspect, with reference to FIGS. 13-19, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Modular energy system offers many advantages in a surgical procedure, as described above in connection with the modular energy systems 2000 (FIGS. 6-12), 3000 (FIGS. 13-15). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

Figure 20:
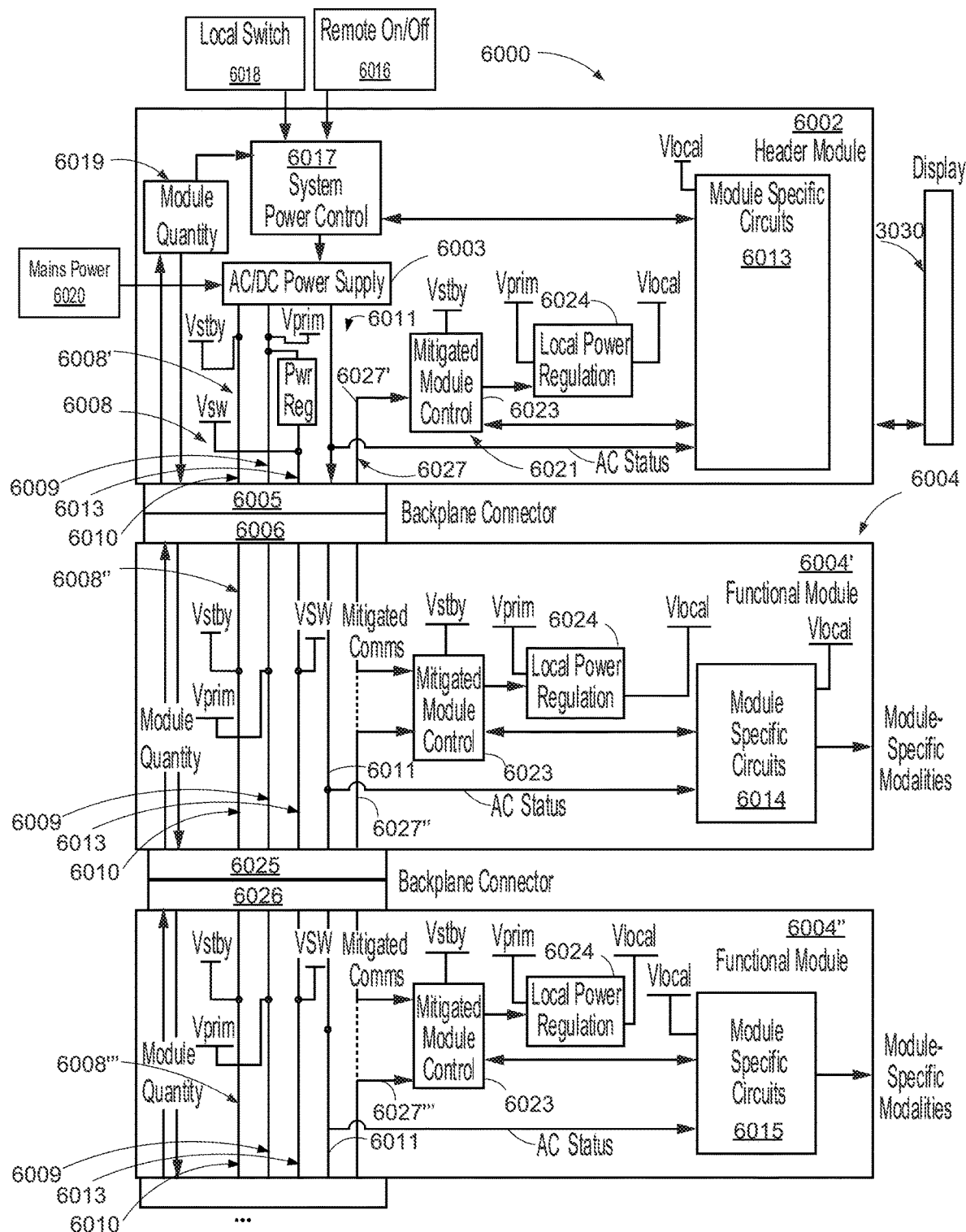
FIG. 20 is a schematic diagram of a modular energy system stack illustrating a power backplane, in accordance with at least one aspect of the present disclosure.

In various aspects, as illustrated in FIG. 20, a modular energy system 6000 that is similar in many respects to the modular energy systems 2000 (FIGS. 6-12), 3000 (FIGS. 13-15). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 20, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 20 demonstrates three separate power domains on the power backplane 6008: a primary power domain 6009, a standby power domain 6010, and an Ethernet switch power domain 6013.

In the example illustrated in FIG. 20, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 20, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 21:
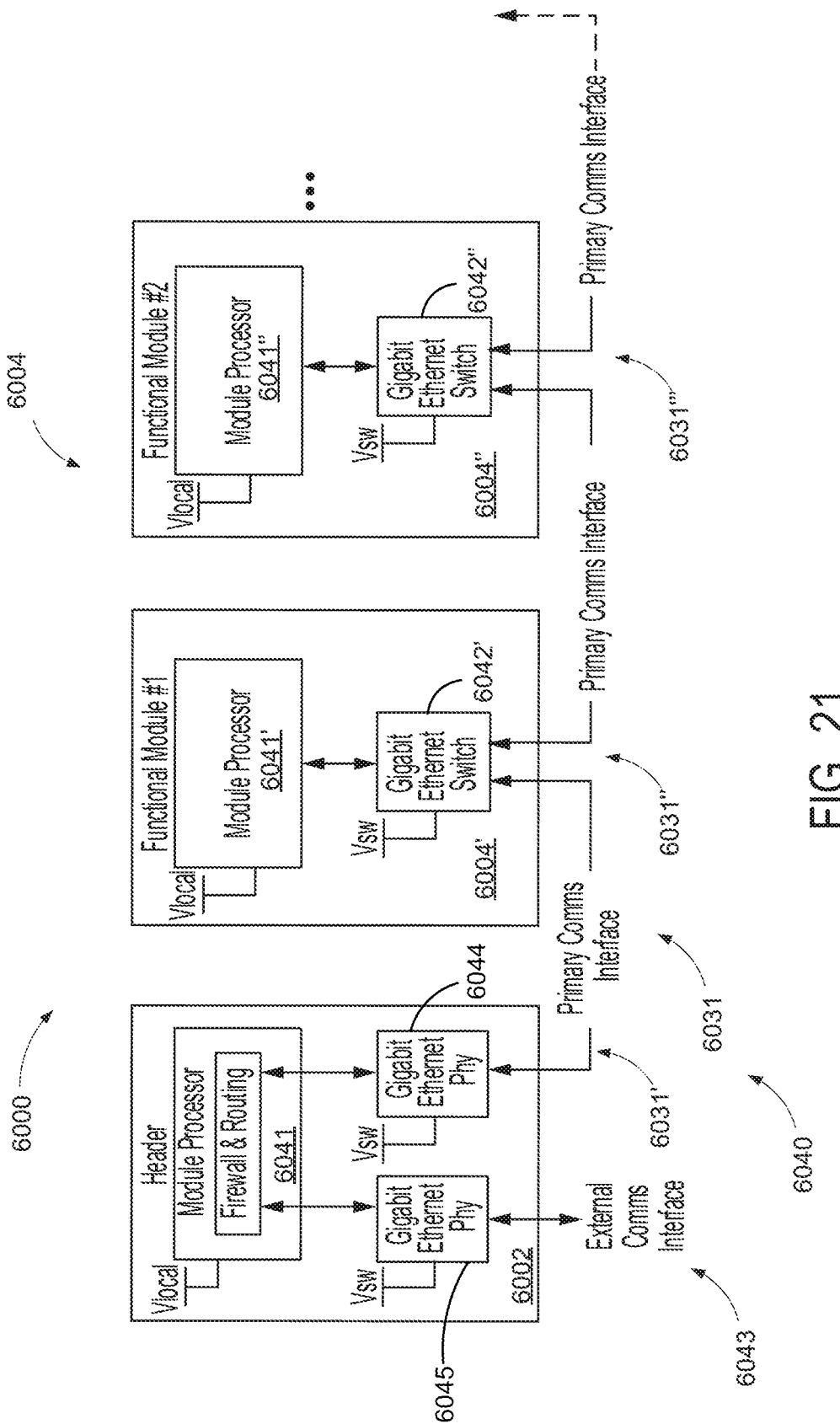
FIG. 21 is a schematic diagram of a modular energy system, in accordance with at least one aspect of the present disclosure.

In various aspects, as illustrated in FIG. 21, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 20, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 20, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 20, the header module 6002 houses a power backplane segment 6008', the first surgical module 6004' houses a power backplane segment 6008", and the second surgical module 6004" houses a power backplane segment 6008'". The power backplane segment 6008' is detachably coupled to the power backplane segment 6008" in the stack configuration. Further, the power backplane 6008" is detachably coupled to the power backplane segment 6008'" in the stack configuration. Accordingly, energy flows from the AC/DC power supply 6003 to the power backplane segment 6008', then to the power backplane segment 6008", and then to the power backplane segment 6008'".

In the example of FIG. 20, the power backplane segment 6008' is detachably connected to the power backplane segment 6008" via pass-through hub connectors 6005, 6006 in the stack configuration. Further, the power backplane segment 6008" is detachably connected to the power backplane segment 6008'" via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008'" from the power backplane segment 6008". However, the connection between the power backplane segment 6008" and the power backplane segment 6008'" remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 20, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 20, the header module 6002 houses a communication backplane segment 6027', the first surgical module 6004' houses a communication backplane segment 6027", and the second surgical module 6004" houses a communication backplane segment 6027'". The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027'" in the stack configuration via the pass-through hub connectors 6025, 6026.

Although the example of FIG. 20 depicts a modular energy system 6000 includes a header module 6002 and two surgical modules 6004' 6004", this is not limiting. Modular energy systems with more or less surgical modules are contemplated by the present disclosure. In some aspects, the modular energy system 6000 includes other modules such as, for example, the communications module 3032 (FIG. 15). In some aspects, the header module 6502 supports a display screen such as, for example, the display 2006 (FIG. 7A) that renders a GUI such as, for example, the GUI 2008 for relaying information regarding the modules connected to the header module 6002. As described in greater detail in connection with the example of FIG. 15, in some aspects, the GUI 2008 of the display screen 2006 can provide a consolidated point of control all of the modules making up the particular configuration of a modular energy system.

FIG. 21 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 21, the header module 6002 houses a communication backplane segment 6031', the first surgical module 6004' houses a communication backplane segment 6031''', and the second surgical module 6004'' houses a communication backplane segment 6031'''. The communication backplane segment 6031' is detachably coupled to the communication backplane segment 6031'' in the stack configuration via the pass-through hub connectors 6005, 6006. Further, the communication backplane segment 6031'' is detachably coupled to the communication backplane segment 6031''' in the stack configuration via the pass-through hub connectors 6025, 6026.

In at least one example, as illustrated in FIG. 21, the primary communications interface 6040 is implemented using the DDS framework running on a Gigabit Ethernet interface. The module processors 6041, 6041', 6041'' are connected to Gigabit Ethernet Phy 6044, and Gigabit Ethernet Switches 6042', 6042''. In the example of FIG. 21, the segmented communication backplane 6031 connects the Gigabit Ethernet Phy 6044 and the Gigabit Ethernet Switches 6042 of the neighboring modules.

In various aspects, as illustrated in FIG. 21, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 20, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 20 and 21, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

User Interface Mitigation Techniques for Modular Energy Systems

Having described a general implementation the header and modules of modular energy systems 2000, 3000, 6000, and various surgical instruments usable therewith, for example, surgical instruments 2204, 2206, and 2208, the disclosure now turns to describe various aspects of modular energy systems comprising user interface mitigation techniques. In other aspects, these modular energy systems are substantially similar to the modular energy system 2000, the modular energy system 3000, and/or the modular energy system 6000 described hereinabove. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

Audio Identification—Double Clocking Data Circuits

As described hereinbelow with reference to FIGS. 22-24, in various aspects, the present disclosure provides modular energy systems 2000, 3000, 6000 comprising user interface mitigation techniques that audio identification double clocking data circuits and associated methods for modular energy system 2000, 3000, 6000 accessories.

In various aspects of the present disclosure, there is a need to identify and confirm audio that a system controller of the modular energy system 2000, 3000, 6000 is playing through a speaker. This may be desirable in audio mitigation techniques to confirm compliance with external standards. Thus, in various aspects, the present disclosure provides circuits and associated methods to uniquely identify a digital audio data stream sent by a controller of the modular energy system 2000, 3000, 6000 to the speakers and confirm that the proper audio data stream was generated by the controller of the modular energy system 2000, 3000, 6000.

Digital audio is often transmitted from a controller to an audio output device such as a Digital-to-Analog Converter (DAC) through a standard protocol called I$^2$S. Those skilled in the art will appreciate that the I$^2$S protocol, also known as an Integrated Inter-IC Sound Bus (I$^2$S), is a serial bus interface standard used for connecting digital audio devices together. The I$^2$S component operates in master mode only. In one aspect, the present disclosure utilizes sending additional data bits inside a standard I$^2$S data frame that serves to identify a unique tone. This technique leverages the fact that most I$^2$S-compatible DACs only consider data present in the audio stream on the rising edge of a clock signal. As such, additional data bits can be inserted in the audio data stream at the falling edge of the clock signal. The additional data bits will be ignored by the DAC but can be read by another controller for mitigation purposes.

Figure 22:
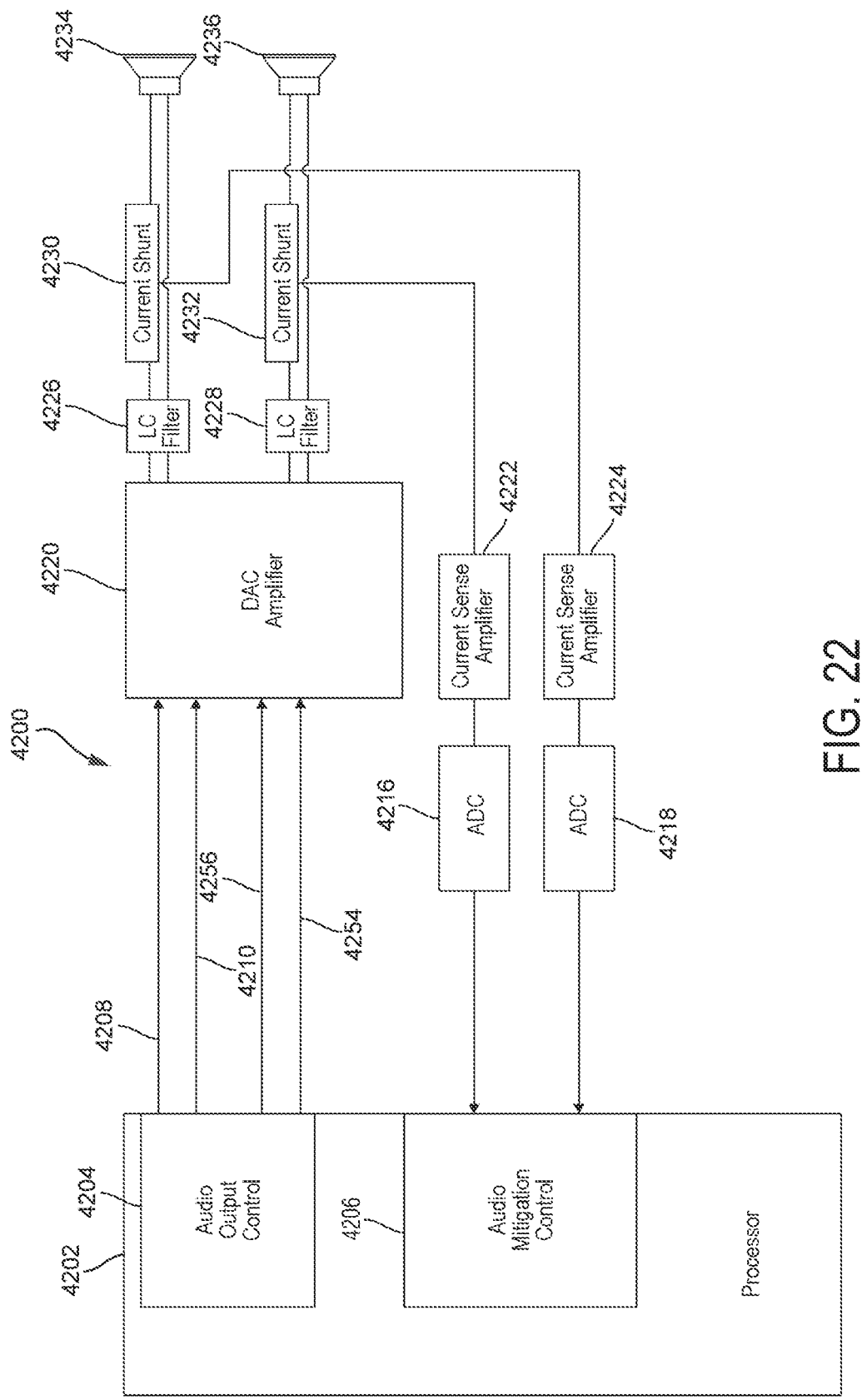
FIG. 22 is a block diagram of an audio output circuit.

FIG. 22 is a block diagram of an audio output circuit 4200. The audio output circuit 4200 includes a processor 4202 coupled to a digital-to-analog converter (DAC)/amplifier circuit 4220 that drives one or more than one speaker 4234, 4236 with an audio tone. The processor includes an audio output control module 4204 and an audio mitigation control module 4206. The audio output control module 4204 and audio mitigation control module 4206 may be implemented in hardware, software, or a combination thereof. In one example, the audio output control module 4204 communicates with the DAC/amplifier circuit 4220 using the I$^2$C serial protocol over a two-wire interface 4208 and control the DAC/amplifier circuit 4220 with hardware control signals 4210. Those skilled in the art will appreciate that the I$^2$C (Inter-Integrated Circuit) protocol is a standard serial, half-duplex, synchronous, multi-master, multi-slave, packet switched, single-ended, serial communication bus.

The processor 4202 sends a digital audio clock signal 4256 and a data signal 4254 to the DAC/amplifier circuit 4220. In one aspect, the data signal 4254 and clock signal 4256 are transmitted to the DAC/amplifier circuit 4220 using a I$^2$S protocol. The I$^2$S-compatible DAC/amplifier circuit 4220 considers data present in the data signal 4254 on the rising edge of the clock signal 4256. This mode is a conventional data signal shown in the upper timing diagram 4250 shown in FIG. 23.

Turning back to FIG. 22, the DAC/amplifier circuit 4220 is coupled to one or more than one speaker 4234, 4236 through one or more than one channel through a filter 4226, 4228, respectively. In the example illustrated in FIG. 22, the DAC/amplifier circuit 4220 includes two analog output channels where a first analog output channel is coupled to a first speaker 4234 through a first filter 4226 and as second analog output channel is coupled to a second speaker 4236 through a second filter 4228. In one aspect, the filter 4226, 4228 may be an inductor/capacitor (LC) filter. A first current shunt 4230 is coupled in series with the first speaker 4234. A second current shunt 4232 is coupled in series with the second speaker 4236. In the example illustrated in FIG. 22, the analog audio signal is provided over the two analog output channels. The first analog channel drives the first speaker 4234 and the second analog channel drives the second speaker 4236. A first current shunt 4230 is coupled to a first current sense amplifier 4224 which is coupled to a first analog-to-digital converter 4218 (ADC) to provide feedback to the audio mitigation control module 4206. Similarly, a second current shunt 4232 is coupled to a second current sense amplifier 4222 which is coupled to a second ADC 4216 to provide feedback to the audio mitigation control module 4206. Alternatively, the ADCs 4216, 4218 may be replaced with comparator circuits.

Activation tones are employed to notify the user that the electrosurgical/ultrasonic instrument has been energized. In the instance that the audio software plays an incorrect tone (i.e., a "button click tone" instead of an "activation tone"), there is a need to mitigate the risk of outputting the wrong tone. In one aspect, risk mitigation may be accomplished by adding additional data bits in the I²S audio signal by the audio mitigation control module 4206 inside the standard I²S data frame. Thus the data signal comprises additional data bits that correspond to a unique tone identification that can be read by the audio mitigation control module 4206 on the falling edge of the clock signal as explained below in the description of FIGS. 23 and 24. The additional data bits are ignored by the DAC/amplifier circuit 4220, which reads data bits only on the rising edge of the clock signal. As used herein, electrosurgical/ultrasonic instrument comprises any one of an electrosurgical instrument that is either monopolar or bipolar, an ultrasonic instrument, or an instrument that employs a combination of electrosurgical and ultrasonic energy, coupled to the energy module 2004 of the modular energy system 2000.

Figure 23:
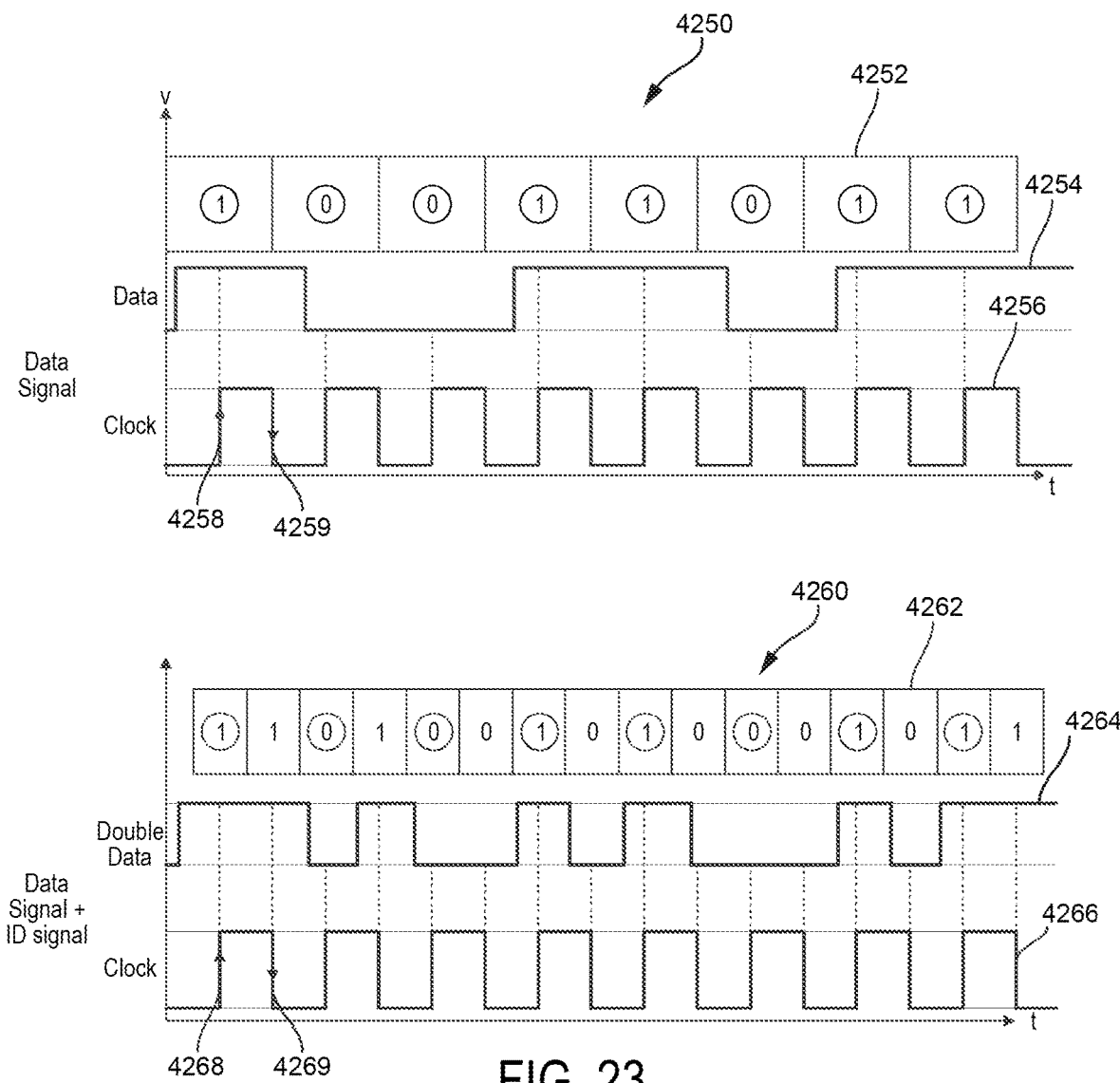
FIG. 23 are timing diagrams of a serial data stream, where the upper timing diagram represents a conventional serial data signal and the lower timing diagram represents a serial data signal with additional bits inserted in the audio data stream, in accordance with at least one aspect of the present disclosure.

FIG. 23 are timing diagrams 4250, 4260 of serial data streams, where the upper timing diagram 4250 represents a first serial data signal 4254 and the lower timing diagram 4260 represents a second serial data signal 4262 which includes the first serial data signal 4254 with additional bits inserted in the audio data stream, in accordance with at least one aspect of the present disclosure. Turning first to the upper timing diagram 4250, in an I²S serial data stream, a serial data signal 4254 is represented as a series of data bits 4252 (10011011) (shown circled) that are read by the DAC/amplifier circuit 4220 (FIG. 22) on the rising edge 4258 of the clock signal 4256 (rising edge bits). The DAC/amplifier 4220 ignores data bits on the falling edge 4259 of the clock signal 4256. The eight data bits 4252 (10011011) represent the audio tone to be played by the speakers 4234, 4236. However, there is no verification or confirmation that the audio tone represented by the eight data bits 4252 (10011011) is the correct audio tone for the current operation of electrosurgical/ultrasonic instrument.

Turning now to the lower timing diagram 4260, in accordance with one aspect of the present disclosure, additional data bits are inserted between the audio data bits 4252 (10011011) shown in the upper timing diagram 4250, to generate a serial double data signal 4264. The serial double data signal 4264 comprises the audio data bits 4252 (10011011) (shown circled) plus unique tone identification data bits (11000001) (shown un-circled) inserted between the audio data bits 4252 (10011011) to form a unique series of data bits 4262 (1101001010001011). The audio data bits 4252 (10011011) are inserted on the rising edge 4268 of the clock signal 4266 (rising edge bits) and the unique tone identification data bits (11000001) are inserted on the falling edge 4269 of the clock signal 4266 (falling edge bits) to form the unique series of data bits 4262 (1101001010001011). The unique tone identification data bits (11000001) inserted on the falling edge 4269 of the clock signal 4266 identify the audio data bits 4252 (10011011) as the correct audio tone for the current operation of the electrosurgical/ultrasonic instrument. Audio bit-depth is not sacrificed. This technique leverages the fact that most I²S-compatible DACs only consider data bits present on the rising edge 4268 of the clock signal 4266. The unique tone identification data bits (11000001) can represent many unique tones and tone combinations and provides for future expandability. Accordingly, the audio mitigation control module 4206 can verify the tone defined by the audio data bits 4252 (10011011) using the unique tone identification data bits (11000001) to identify the audio data bits 4252 (10011011) that represent the audio tone. It will be appreciated that the audio data bits 4252 (10011011) will change on each sample so as to define an actual audio tone, whereas the unique tone identification data bits (11000001) will remain constant, identifying the tone throughout all of the changing audio samples.

Figure 24:
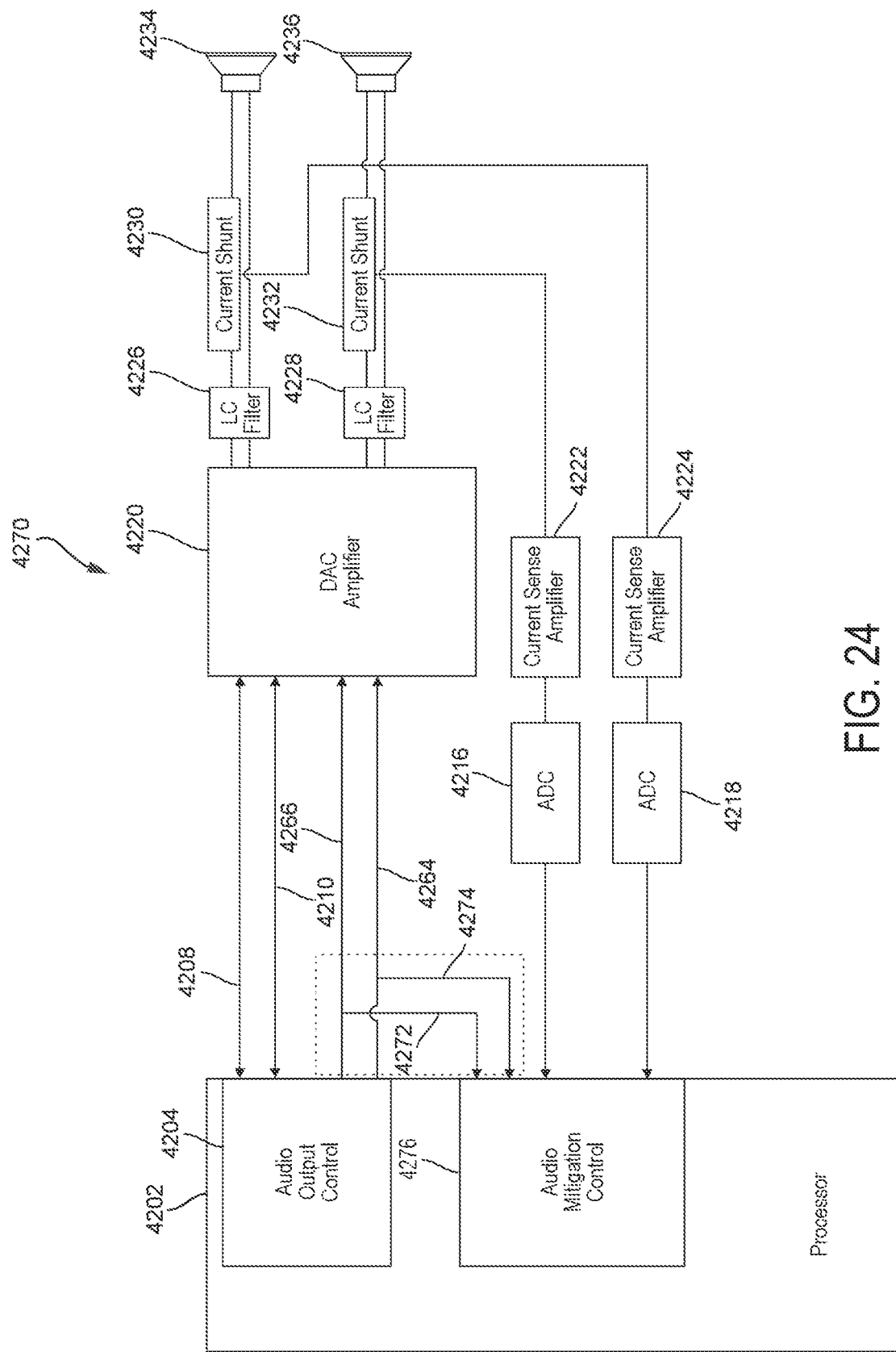
FIG. 24 is a block diagram of an audio output circuit that utilizes additional data bits inside a standard I²S data frame that correspond to unique tone identification, in accordance with at least one aspect of the present disclosure.

FIG. 24 is a block diagram of an audio output circuit 4270 that utilizes additional data bits inside a standard I²S data frame that correspond to unique tone identification, in accordance with at least one aspect of the present disclosure. In the example shown in FIG. 24 and with reference also to FIG. 23, the serial double data signal 4264 and the clock signal 4266 are fed back to the audio mitigation control module 4276 of the processor 4202. The audio mitigation control module 4276 reads the serial double data signal 4264 on the falling edge 4269 of the clock signal 4266 and confirms that the correct tone is sent to the speakers 4234, 4236. As previously discussed, the I²S-compatible DAC/amplifier circuit 4220 only considers data bits present on the rising edge 4268 of the clock signal 4266 and ignores the unique tone identification bits present on the falling edge 4269 of the clock signal 4266. Thus, the additional data bits can represent many unique tones and tone combinations and provides for future expandability.

Feeding back the serial double data signal 4264 and the clock signal 4266 to the audio mitigation control module 4276 provides an elegant solution and can be read by the audio mitigation control module 4276 as digital data without any extra hardware. The additional data bits read on the falling edge 4269 of the clock signal 4266 can represent many unique tones and tone combinations that provides for future expandability. Further, this technique provides assurance that tones are correctly sent to and played by the speakers 4234, 4236 without sacrificing audio bit-depth as all the audio data bits can be used for playing audio tones. Accordingly, if an incorrect tone is detected, based on knowing the expected tone due to a knowledge of what operations are taking place, or similar activity, the processor 4202 may present a fault to a user, cease the surgical functions, among other mitigating actions.

Mitigation for Energy System User Interface (UI) Display

As described hereinbelow with reference to FIGS. 25-28, in various aspects, the present disclosure provides modular energy systems 2000, 3000, 6000 comprising user interface mitigation techniques for user interface (UI) displays of the modular energy systems 2000, 3000, 6000. An energy generator component of the modular energy system 2000, 3000, 6000 may improperly generate a visual indication of instrument activation status on a user interface (UI) display as required by external standards. For example, to prevent the generation of an incorrect UI display, the present disclosure provides circuits and associated methods to actively confirm that a generated visual indication is appropriate and correct, thereby reducing or eliminating the risk of displaying an incorrect UI message or graphic. In one aspect, the present disclosure provides circuits and associated methods to monitor a copy of display signals to validate the entire display data-path.

In one general aspect, it may be necessary for an energy module 2004, 3004, 6004 component of the modular energy system 2000, 3000, 6000 to provide a visual indication of instrument activation status. In the modular energy system 2000, 3000, 6000 described herein, this may be accomplished, at least in part, by changing the graphics on a graphical display unit. In this instance, the modular energy system 2000, 3000, 6000 should ensure that the display state matches the instrument activation state at all times. There may be several points of failure in the display generation path: failure of the software creating the graphics may fail, the hardware display drivers may fail, any data conversion processes may malfunction, etc. In one aspect, the present disclosure comprises a header module 2002, 3003, 6002 of the modular energy system 2000, 3000, 6000 comprises a circuit which, if a risk analysis determines is necessary, is able to confirm proper operation of a significant portion of the data pathway to the display. A block diagram of such a circuit is described below.

Figure 25:
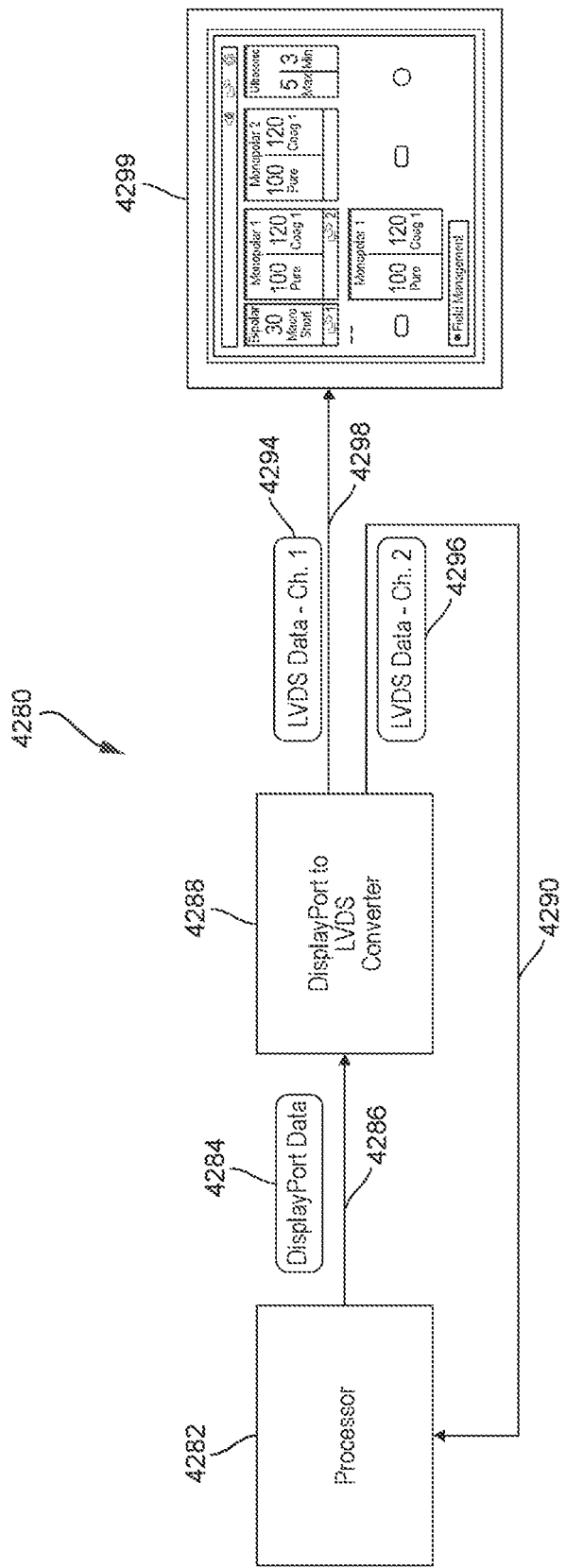
FIG. 25 is a block diagram of a circuit for mitigating the function of a user Interface (UI) display of a modular energy system, or similar surgical equipment, in accordance with at least one aspect of the present disclosure.

FIG. 25 is a block diagram of a circuit 4280 for mitigating the function of a user interface (UI) display 4299 of a modular energy system 2000, 3000, 6000 or similar surgical equipment, in accordance with at least one aspect of the present disclosure. The circuit 4280 comprises a processor 4282 coupled to a video data converter circuit such as, for example, a DisplayPort to low-voltage differential signaling (LVDS) converter circuit 4288. Those skilled in the art will appreciate that DisplayPort is a digital display interface standard by the Video Electronics Standards Association (VESA). The DisplayPort interface is primarily used to connect a video source to a display device and it can also carry audio, USB, and other forms of data. DisplayPort can replace VGA, FPD-Link, and Digital Visual Interface (DVI).

DisplayPort-formatted data 4284 from the processor 4282 is applied to the DisplayPort to LVDS converter 4288 via a standard DisplayPort interface 4286. The LVDS data 4294, differential video signaling data, on channel-1 is provided to the UI display 4299 via line 4298. LVDS data 4296 on channel-2 is fed back to the processor via line 4290. As shown, the data 4294 on channel-1 is the same as the data on channel-2.

The processor 4282, which may be implemented as a system on a chip (SoC or the main processor in the header module 2002, 3004, 6004 of the modular energy system 2000, 3000, 6000) generates graphics internally in software, which is then driven out through the standard DisplayPort interface 4286. The DisplayPort-formatted data 4284 then is translated into an LVDS signal (standard display interface signaling) through a specialized onboard converter device such as the DisplayPort to LVDS converter circuit 4288. The output of the DisplayPort to LVDS converter circuit 4288 has two distinct display channels: channel-1 and channel-2, that may be utilized individually or in tandem. In one aspect, in accordance with the present disclosure, the DisplayPort to LVDS converter circuit 4288 connects one channel, e.g., channel-1, to the actual user display 4299 and connects the second channel, e.g., channel-2, back to the processor 4282 for interpretation of the LVDS data 4296. The DisplayPort to LVDS converter circuit 4288 is configured to "mirror" the channels (channel-1, channel-2) such that identical data is driven out of both output channels (channel-1, channel-2).

In this way, the processor 4282 confirms the operation of the DisplayPort to LVDS converter circuit 4288 using the LVDS signals on line 4290 carrying the LVDS data 4296 on channel-2, which change over time. If the LVDS signals on line 4290 remain static and do not alter state over time, the processor 4282 may conclude that something in the display path is malfunctioning. Further, in one aspect, the processor 4282 interprets the LVDS feedback signals to reconstruct the resulting image defined by the LVDS data 4296 on channel-2, which should be identical to the LVDS data 4294 on channel-1. The reconstructed resulting image can then be compared against an expected image to confirm that the DisplayPort data 4284 is correct, is being converted to LVDS data 4294, 4296 correctly, and that the image appearing on the screen of the UI display 4299 is appropriate for the given instrument activation state (or other surgical context).

In one aspect, the LVDS data 4296 on channel-2 is provided to a second processor that is different from the processor 4282. The LVDS data 4296 on channel-2 second provides a copy of the differential video signaling data to the second processor. The second processor is configured to determine whether the differential video signaling data on the second output channel is changing over time.

Figure 26:
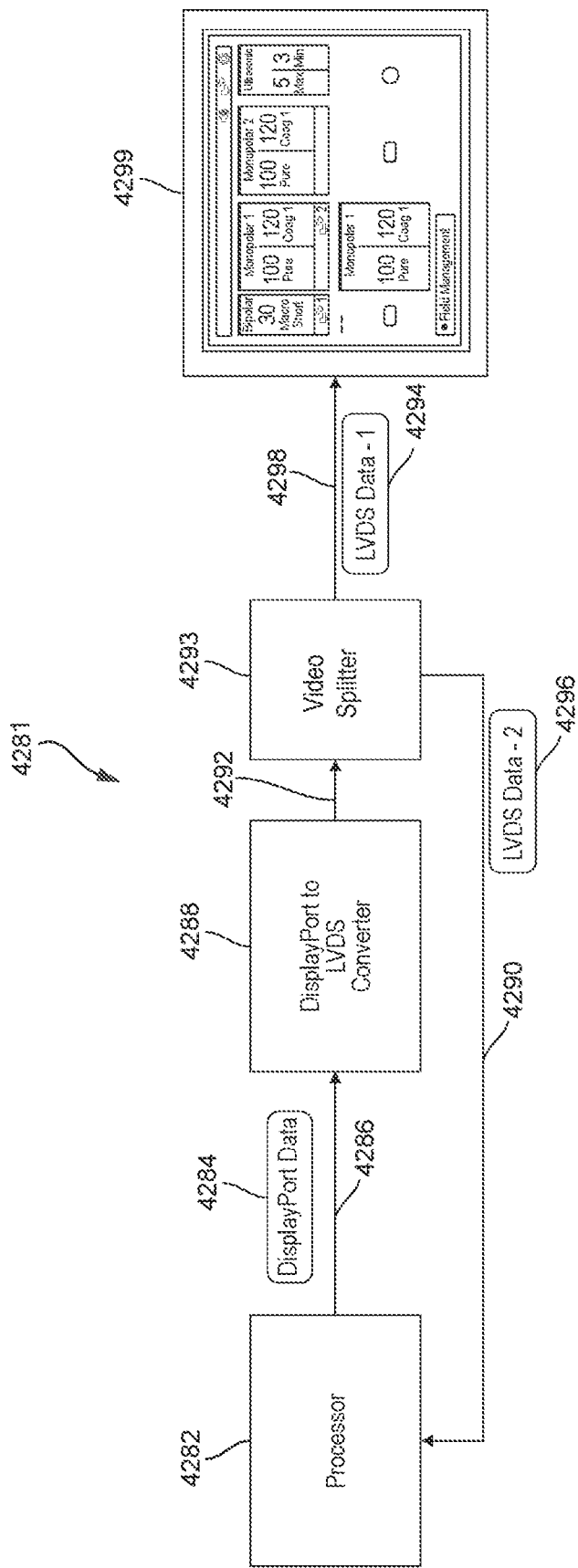
FIG. 26 is a block diagram of an LVDS converter circuit having one output channel, which is passed through a video splitter circuit coupled to the output channel of the LVDS converter circuit, the video splitter circuit having two video data outputs, in accordance with at least aspect of the present disclosure.

In FIG. 26, the LVDS converter circuit 4288 has one output channel 4292, which is passed through a video splitter circuit 4293 coupled to the output channel of the LVDS converter circuit 4288, where the video splitter circuit 4293 has two video data outputs 4294, 4296, in accordance with at least aspect of the present disclosure. The first data output 4294 is coupled to the UI display 4299 via line 4298 and the second data output 4296 is coupled back to the processor 4282 on line 4290. In one aspect, the LVDS data 4296 on is provided to a second processor that is different from the processor 4282. The LVDS data 4296 on provides a copy of the differential video signaling data to the second processor. The second processor is configured to determine whether the differential video signaling data on the second output channel is changing over time.

Figure 27:
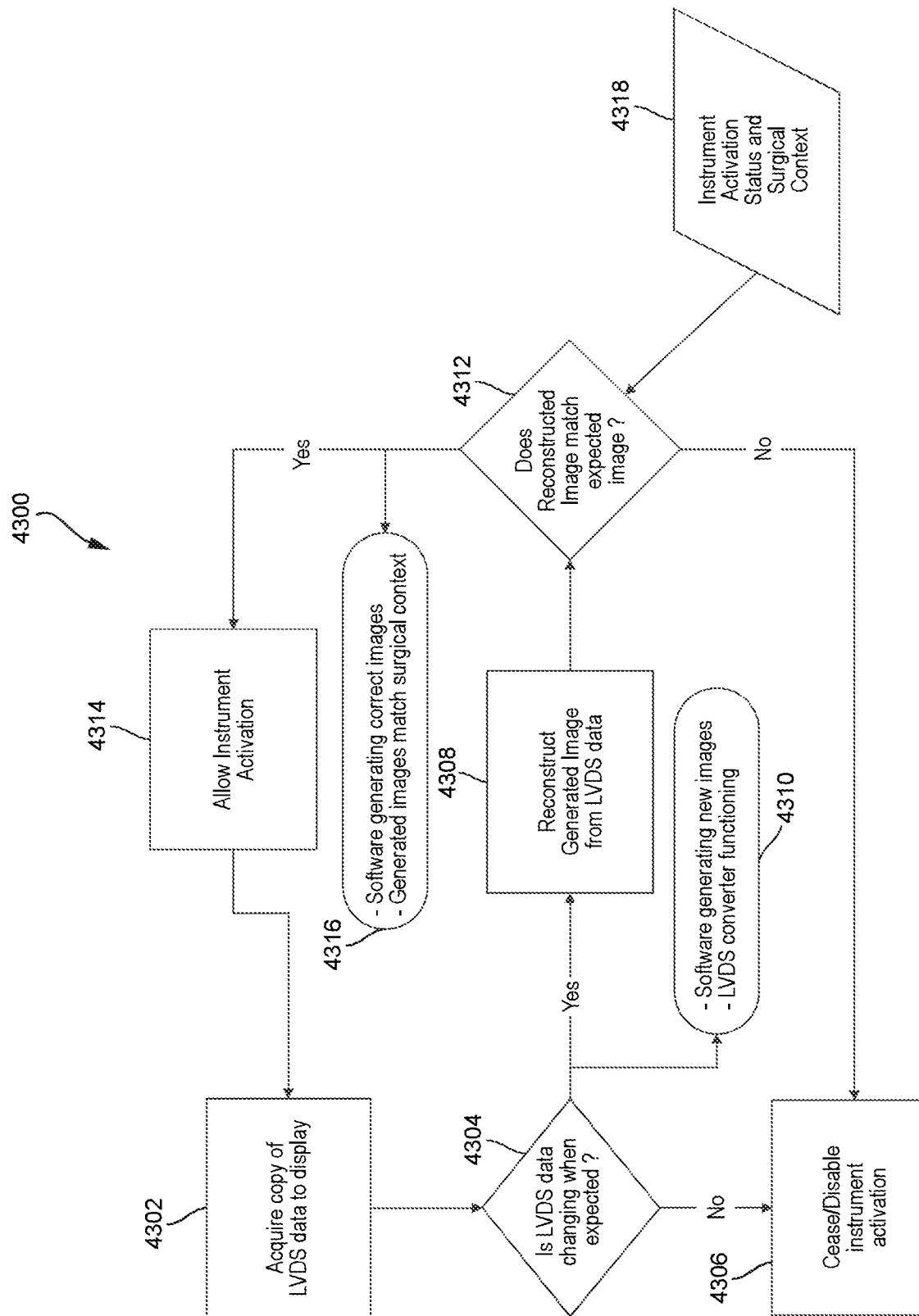
FIG. 27 is a flow diagram of a method for mitigating the function of the user Interface (UI) display of the modular energy system shown in FIG. 25 (25), or similar surgical equipment, in accordance with at least one aspect of the present disclosure.

FIG. 27 is a flow diagram of a method 4300 for mitigating the function of the user Interface (UI) display 4299 of the modular energy system circuit 4280 shown in FIG. 25, or similar surgical equipment, in accordance with at least one aspect of the present disclosure. With reference also to FIG. 25, the method 4300 may be implemented with the circuit 4280, for example. In accordance with the method 4300, the processor 4282 acquires 4302 a copy of the LVDS data 4296 on channel-2 to be displayed. The processor 4282 determines 4304 whether the LVDS data 4296 on channel-2 is changing over time when expected. If the LVDS data 4296 on channel-2 is not changing when expected, the processor 4282 ceases/disables 4306 instrument activation or other surgical functions. If the LVDS data 4296 on channel-2 is changing when expected, the processor 4282 determines that the software is generating 4310 new images and determines that the DisplayPort to the LVDS converter 4288 is functioning and the LVDS data 4294 on channel-1 is likely proper. The processor 4282 then reconstructs 4308 the generated image from the LVDS data 4296 on channel-2. If the reconstructed image does not match the expected image, the processor 4282 ceases/disables 4306 instrument activation or other surgical functions. If the reconstructed image matches the expected image, the processor 4282 determines that the software is generating 4316 correct images and the generated images match the surgical context and enables 4314 instrument activation. The method 4300 returns to the processor 4282 acquiring 4302 a copy of the LVDS data 4296 on channel-2 to display and the process repeats as described above.

Figure 28:
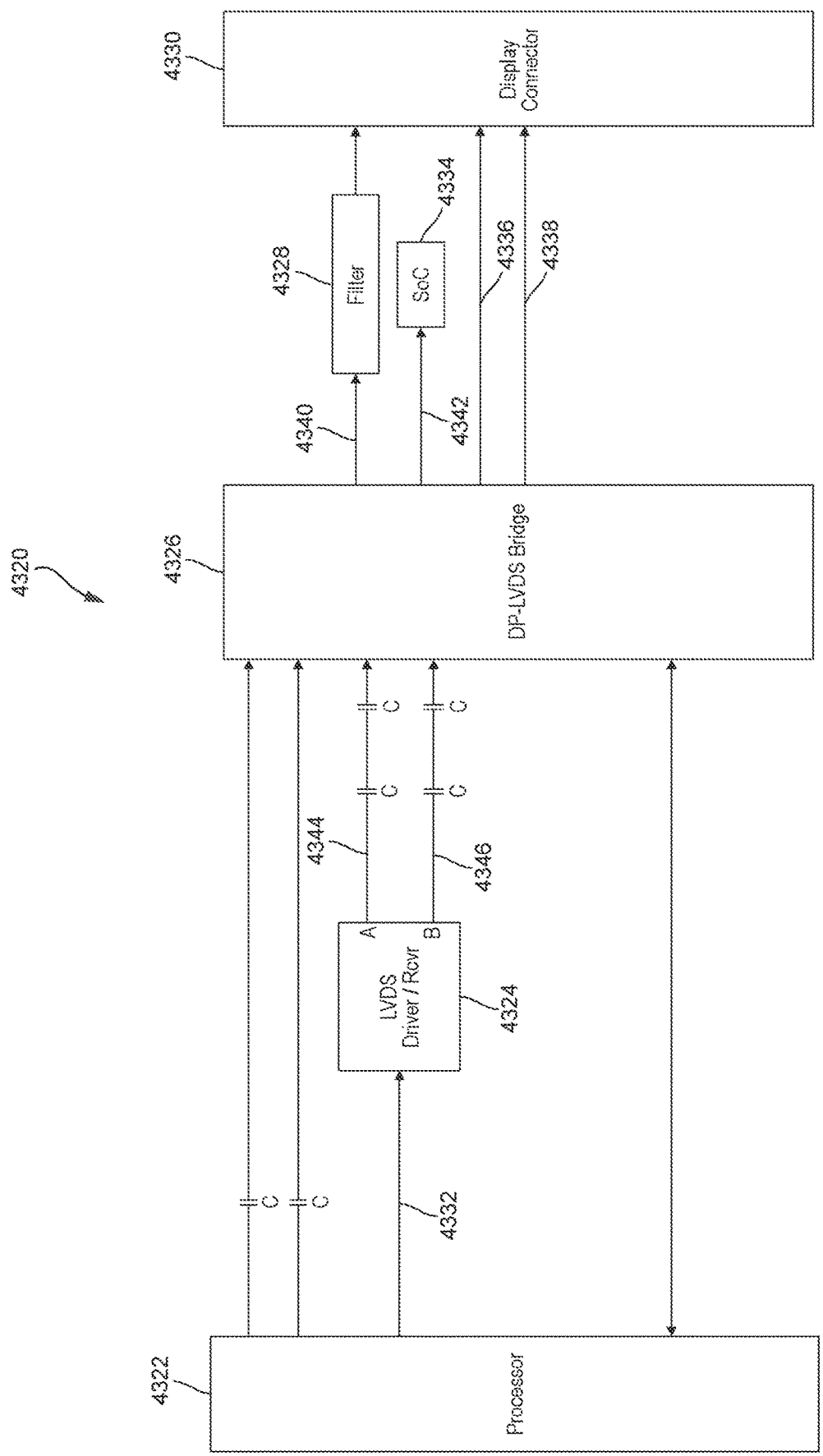
FIG. 28 is a block diagram of a circuit for mitigating the function of a user Interface (UI) display of a module energy system, or similar surgical equipment, in accordance with at least one aspect of the present disclosure.

FIG. 28 is a block diagram of a circuit 4320 for mitigating the function of a user Interface (UI) display of a modular energy system 2000, 3000, 6000 or similar surgical equipment, in accordance with at least one aspect of the present disclosure. The method 4300 shown in FIG. 27 may be implemented with the circuit 4320, for example. The output 4332 of the processor 4322 is coupled to a LVDS driver/receiver circuit 4324. The outputs 4344, 4346 of the LVDS driver/receiver circuit 4324 are coupled to a DP-LVDS bridge circuit 4326. The DP-LVDS bridge circuit 4326 is an embedded DisplayPort to LVDS bridge device that enables connectivity between an embedded DisplayPort (eDP) source and a LVDS display panel (not shown) coupled to a display connector 4330. The DP-LVDS bridge circuit 4326 processes the incoming DisplayPort (DP) stream, performs DP to LVDS protocol conversion and transmits a processed stream in LVDS format. In one aspect, the DP-LVDS bridge circuit 4326 may comprises two high-speed ports: a receive port facing the DP Source (for example, CPU/GPU/chip set) and a transmit port facing the LVDS receiver (for example, LVDS display panel controller).

A first LVDS output 4340 of the DP-LVDS bridge circuit 4326 is coupled to a common mode filter 4328 to suppress EMI/RFI common mode noise on high speed differential serial Display Port lines and other high speed serial interfaces. The common mode filter 4328 may comprise a very large differential bandwidth to comply with standards and can protect and filter two differential lanes. A second LVDS output 4342 of the DP-LVDS bridge circuit 4326 is coupled to a system-on-chip 4334 (SoC). A pulse width modulation output 4336 (PWMO) of the DP-LVDS bridge circuit 4326 is coupled to the display panel via the display connector 4330. A backlight enable output 4338 of the DP-LVDS bridge circuit 4326 is also coupled to the display via a display connector 4330.

Audio Mitigation Using Super-Audible Tones

As described hereinbelow with reference to FIGS. FIGS. 29-38, in various aspects, the present disclosure provides modular energy systems 2000, 3000, 6000 comprising audio mitigation circuits and associated methods for using super-audible tones in the modular energy systems 2000, 3000, 6000. In various aspects, electrosurgical energy modules 2004, 3004, 6004 in a modular energy system 2000, 3000, 6000 use audio tones to indicate alarms, alerts, and energy activations. Audio feedback is part of a protocol to alert the user that the electrosurgical instrument has been energized by the energy module 2004, 3004, 6004 and is functioning properly. Accordingly, in one aspect, audio feedback protocols employ hardware/software mitigation techniques. One potential audio failure that requires mitigation is the possibility that the software plays an incorrect audio file. Accordingly, there is a need for hardware/software techniques for mixing audio files, where each file is checked against an expected asset.

In one aspect, the present disclosure provides a hardware/software technique that employs pre-processing of audio assets, where each audio asset is filtered to reserve a portion of the spectrum outside the audible range referred to herein s super-audible to indicate that the tones are in the upper ranges of the audio frequency spectrum. This super-audible range is divided into bins, where each bin can be allocated to a unique audio asset. The audio file may be mixed with a sine wave of the allocated identification (ID) frequency prior to being loaded into the energy module 2004, 3004, 6004 of the modular energy system 2000, 3000, 6000.

In one aspect, when the modular energy system 2000, 3000, 6000 software receives a request to play one or more than one audio file, the audio files are mixed (if necessary) and streamed to an audio amplifier, such as the DAC/amplifier circuit 4220 shown in FIG. 24. In one implementation, the header module 2002, 3002, 6002 of the modular energy system 2000, 3000, 6000 may include a programmable circuit, such as the audio mitigation control module 4276, for example, to access the audio data lines between the processor 4202 and the DAC/amplifier 4220, for example. In another implementation, the data is accessed through the current sense amplifiers 4222, 4224 is applied to the ADCs 4216, 4218 and the digital outputs are provided to the audio mitigation control module 4276 portion of the processor 4202. This allows the DAC/amplifier 4220 and speaker filters 4226, 4228 to be included in the mitigation function performed by the audio mitigation control module 4276 portion of the processor 4202 based on the digitized data received from the ADCs 4216, 4218. The audio mitigation control module 4276 may be implemented in software, firmware, or hardware such as an FPGA circuit.

The programmable circuit may be configured to perform the following functions when audio is played:
1) Fetch from software expected audio data file unique identification numbers stored in a memory coupled to the processor;
2) Implement a filter to filter audio data to isolate the super-audible frequency range, where the filter may be a high pass or band pass filter;
3) Under-sample (decimate) the audio data down to baseband (0 Hz to max super-audible frequency) to enable a smaller fast Fourier transform (FFT) calculation without sacrificing bin size;
4) Calculate the FFT of the under-sampled data;
5) Perform a peak detect function on the FFT; and
6) Compare the peaks to expected super-audible unique identification tones.

Depending on the under-sampling factor, the frequencies may show up as Fs/2−tone_freq, as described hereinbelow.

In one aspect, the present disclosure provides circuits and associated methods for pre-processing audio assets of the energy module 2004, 3004, 6004 of the modular energy system 2000, 3000, 6000. In one aspect, a portion of the spectrum outside the audible range is reserved. For example, this reserved range may be selected as the frequency band of 20 kHz-24 kHz. The original audio assets outside the reserved band are low-pass filtered to remove any audio content within the reserved band. Unique super-audible tones are applied to each audio asset within the reserved band to serve as an ID. In one aspect, the reserved band audio assets are divided into 50 Hz bins to produce a total of 80 unique IDs. In another aspect, the reserved band audio assets are divided into 31.49 Hz bins, resulting in 256 unique IDs. In this way, the audio file contains the original audio asset within frequencies below the reserved band, in addition to unique super-audible tone or tones serving as unique IDs within the reserved band.

With reference also to the audio output circuit 4270 shown in FIG. 24, the audio files are sent to an audio DAC/amplifier 4220 by the software in the processor 4202. The software may mix multiple audio files for simultaneous activations, for example. In one implementation, a programmable circuit, such as an FPGA, for example, intercepts the audio file on its way to the amplifier DAC/amplifier 4220. In another implementation, the analog current between the DAC/amplifier 4220 and the speakers 4234, 4236 is read via the current shunts 4230, 4232. The audio data is filtered by the filters 4226, 4228 to isolate the super-audible range of frequencies 20-24 kHz. The current sensed by the current shunts 4230, 4232 is applied to corresponding current sense amplifiers 4224, 4222. The ADCs 4216, 418 digitize the outputs of the current sense amplifiers 4222, 4224 for further digital processing by the processor 4202 digital mitigation control module 4276.

The filters 4226, 4228 may be high pass filter or band pass filters. In one implementation, the filter 4226, 4228 may be a band pass filter when using a class-D versus linear amplifier. A class-D amplifier produces a lot of high frequency artifacts that can be removed with a band pass filter. Filtering is performed prior to under-sampling. Subsequently, the audio data is under-sampled to "fold" the super-audible frequency band down to baseband. This technique enables a smaller FFT calculation without sacrificing bin size. Using peak detection, the presence of unique identification tones, as described in connection the lower timing diagram 4260 in FIG. 23, can be determined which indicates which specific audio file or combination of files is being sent to the audio amplifier. This technique also may be employed without the optional step of under-sampling or folding the super-audible frequency band to baseband. The programmable circuit checks the identified audio files identified by the super-audible frequencies (IDs) against expected audio files. If a mismatch between the expected audio files and the files being sent to the audio amplifier is detected, a fault may be presented to the user, surgical functions may be ceased or prevented, or some other corrective action may be taken.

Example audio files are described hereinbelow with reference to FIGS. 29-37. In each of the graphs shown in FIGS. 29-37, the vertical axis represents amplitude (dB) and the horizontal axis represents frequency (kHz)

Figure 29:
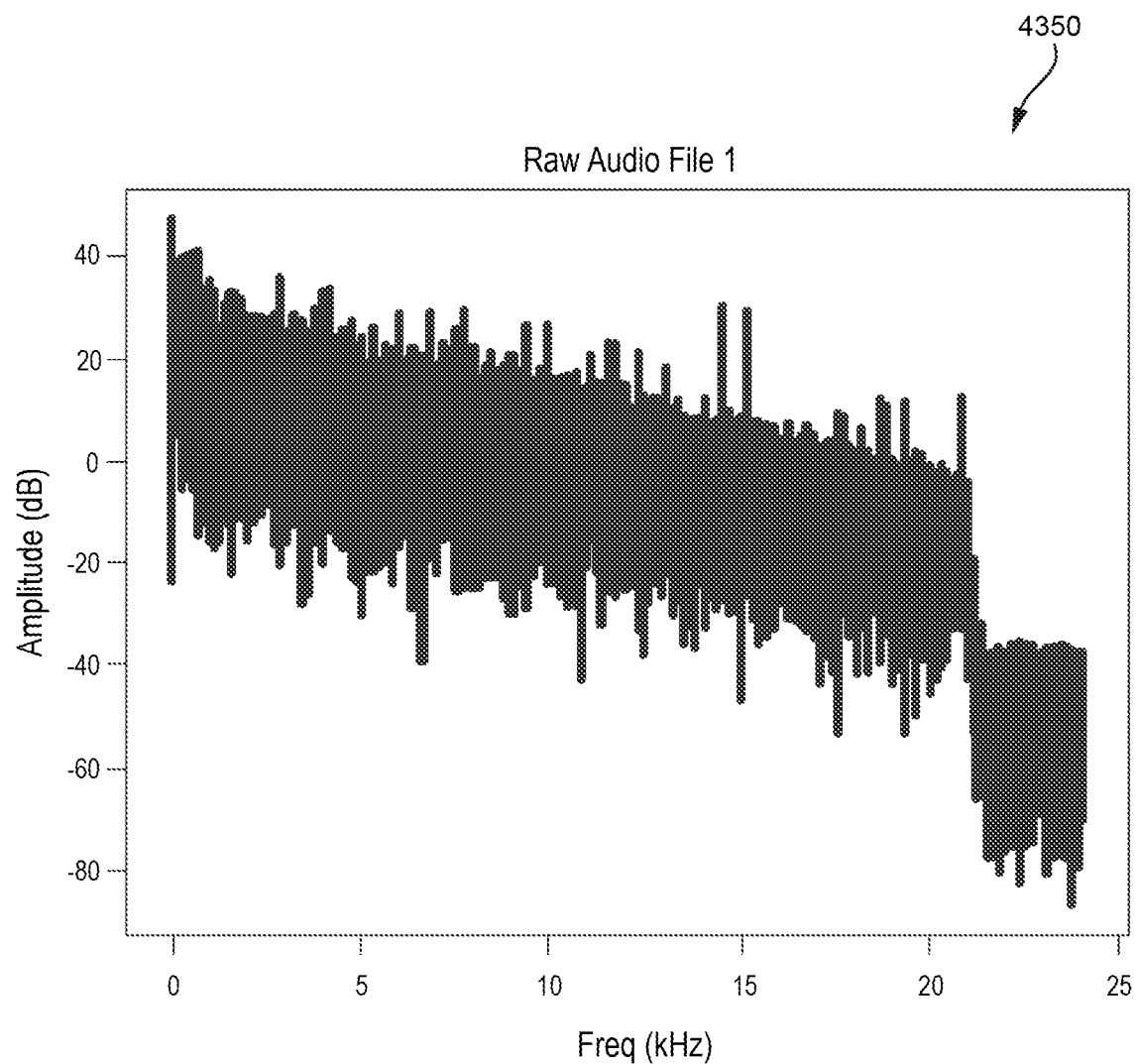
FIG. 29 is a graph of a frequency spectrum of a first raw unfiltered audio file.
Figure 30:
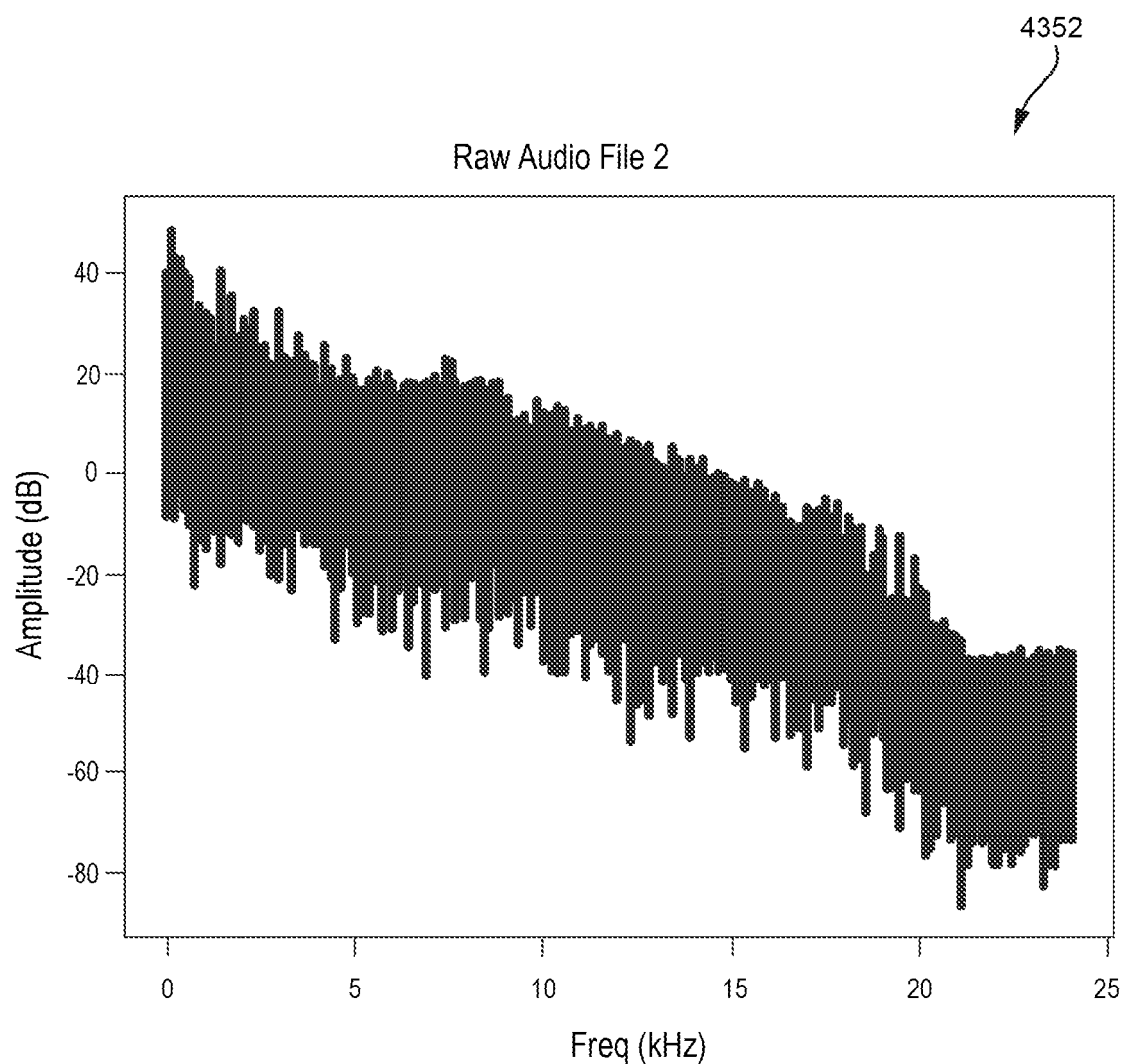
FIG. 30 is a graph of a frequency spectrum of a second raw unfiltered audio file.

FIG. 29 is a graph of a frequency spectrum of a first raw unfiltered audio file 4350 and FIG. 30 is a graph of a frequency spectrum of a second raw unfiltered audio file 4352.

Figure 31:
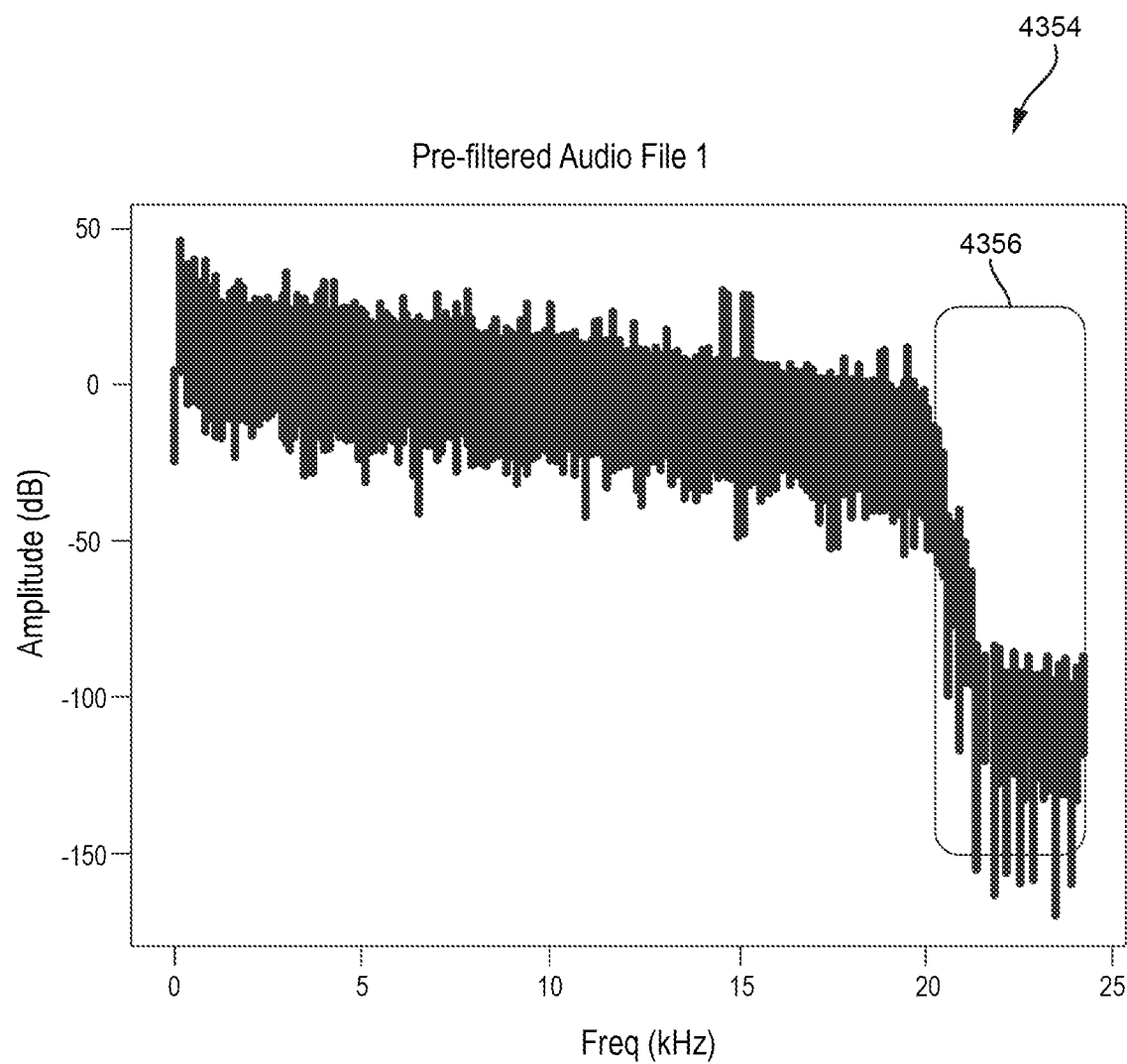
FIG. 31 is a graph of a frequency spectrum of a first pre-filtered audio file and a first target super-audible range (20-24 kHz).
Figure 32:
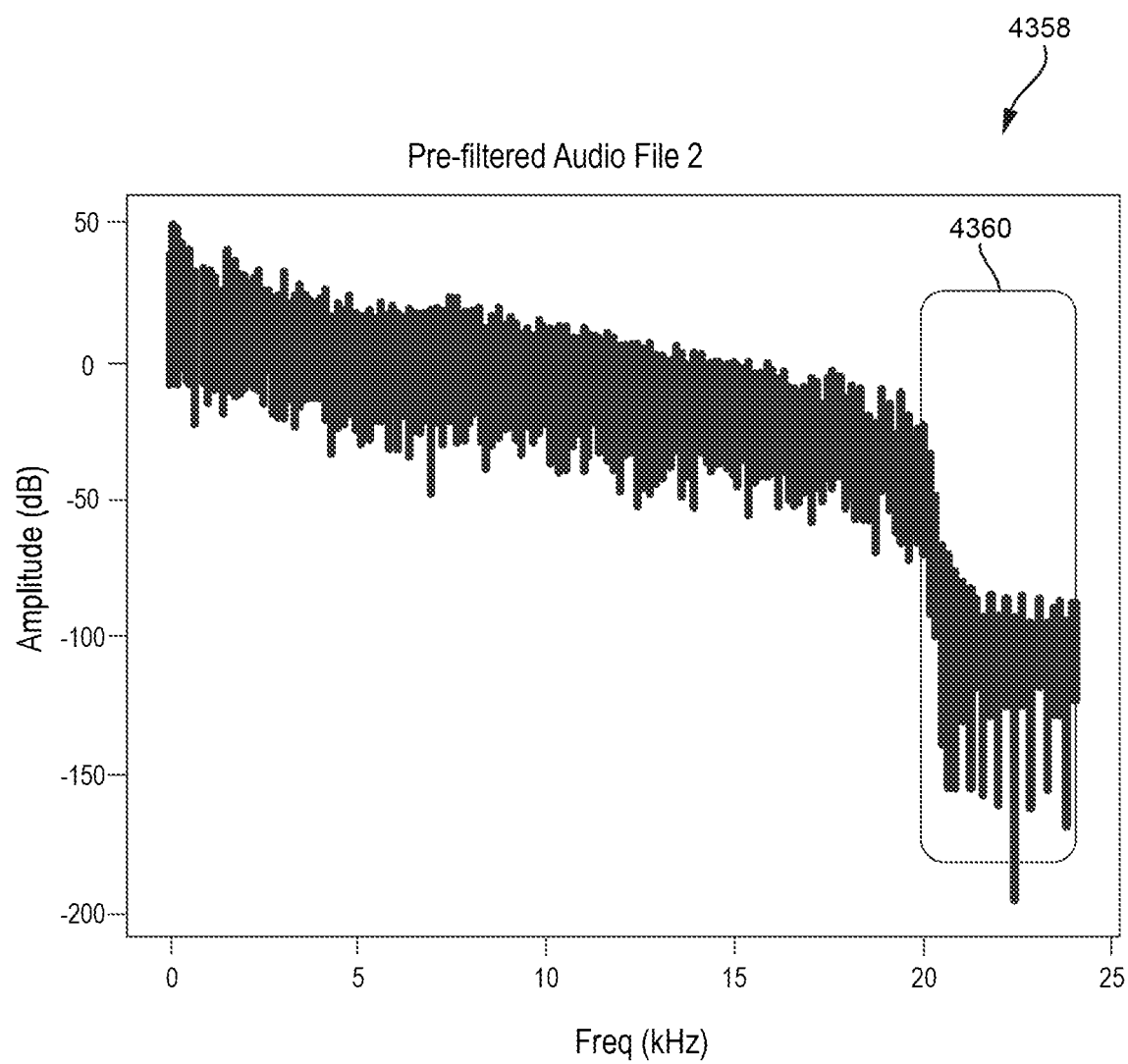
FIG. 32 is a graph of a frequency spectrum of a second pre-filtered audio file and a second target super-audible range (20-24 kHz).

FIG. 31 is a graph of a frequency spectrum of a first pre-filtered audio file 4354 and a first target super-audible range 4356 (20-24 kHz). FIG. 32 is a graph of a frequency spectrum of a second pre-filtered audio file 4358 and a second target super-audible range 4360 (20-24 kHz). Each audio file 4354, 4358 is low-pass filtered before applying any super-audible identification tones in the super-audible range (20 kHz-24 kHz).

Figure 33:
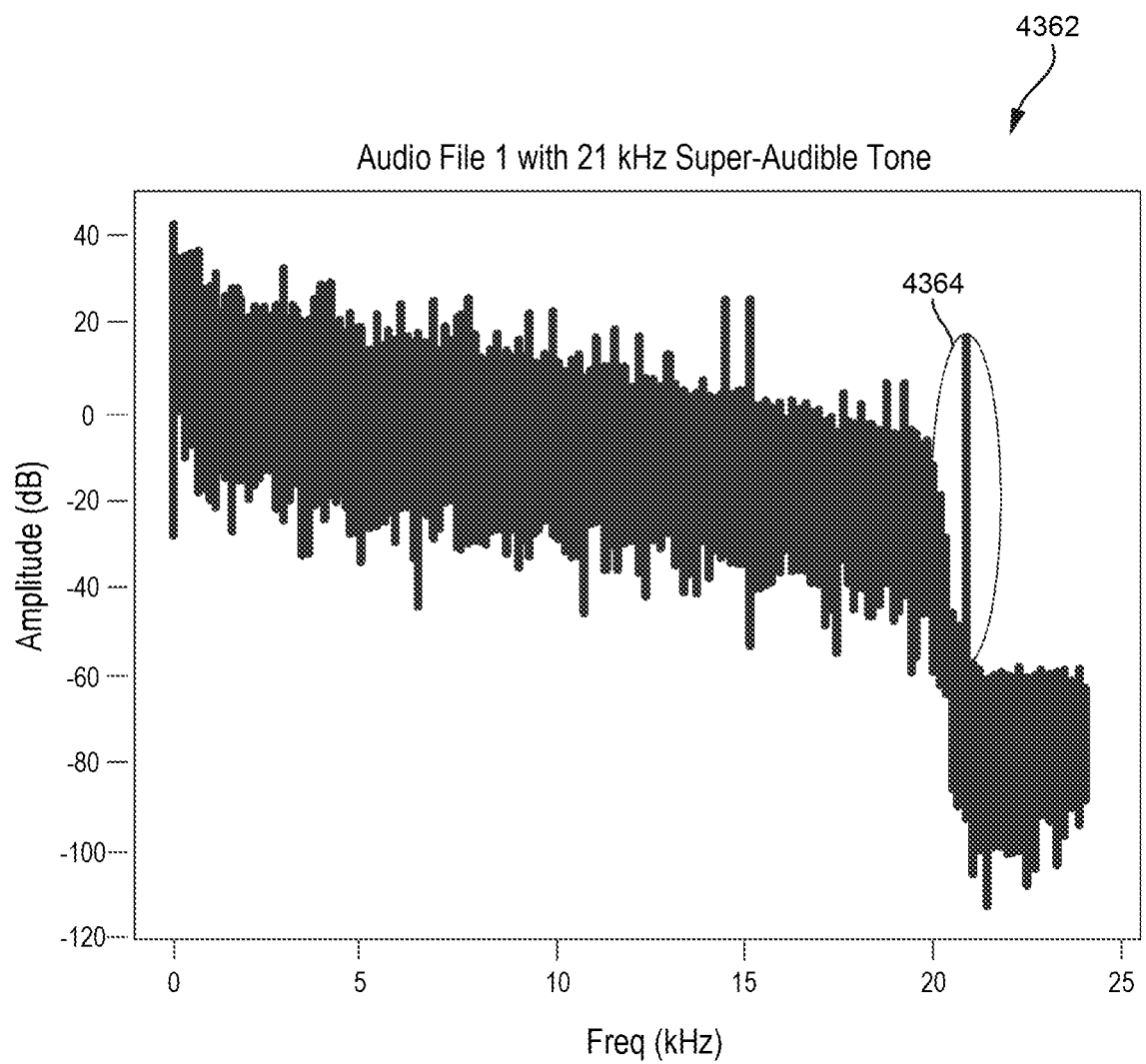
FIG. 33 is a graph of a frequency spectrum of a first audio file with a single 21 kHz super-audible tone.
Figure 34:
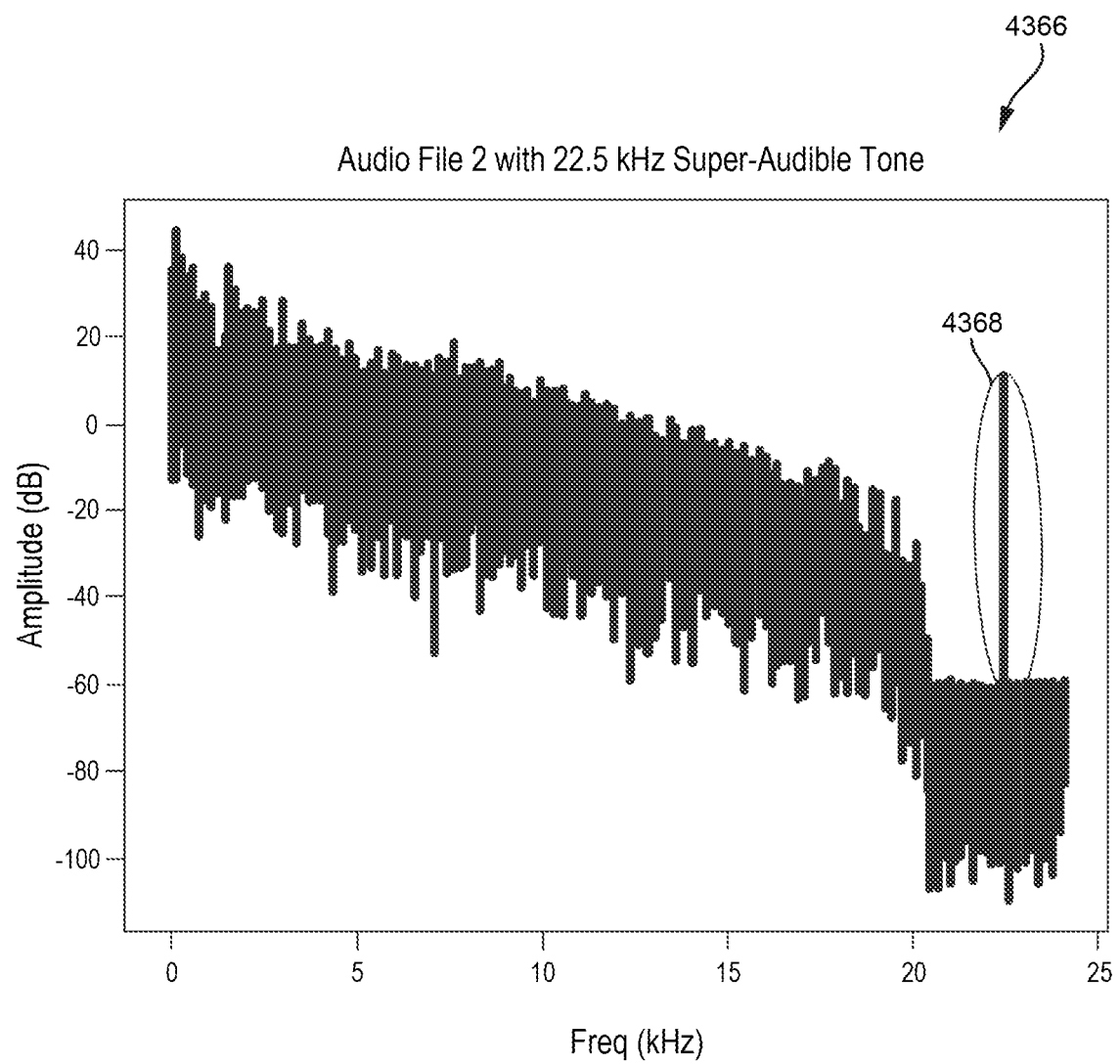
FIG. 34 is a graph of a frequency spectrum of a second audio file with a single 22.5 kHz super-audible tone.

FIG. 33 is a graph of a frequency spectrum of a first audio file 4362 with a single 21 kHz super-audible tone 4364. FIG. 34 is a graph of a frequency spectrum of a second audio file 4366 with a single 22.5 kHz super-audible tone 4368. The single, unique super-audible tone 4364, 4368 is applied to each of the pre-filtered audio files 4354 (FIG. 31), 4358 (FIG. 32) prior to loading into the energy module 2004. The first and second audio files 4362, 4366 each with a single super-audible tone 4364, 4368, respectively, are mixed in the energy module 2004.

Figure 35:
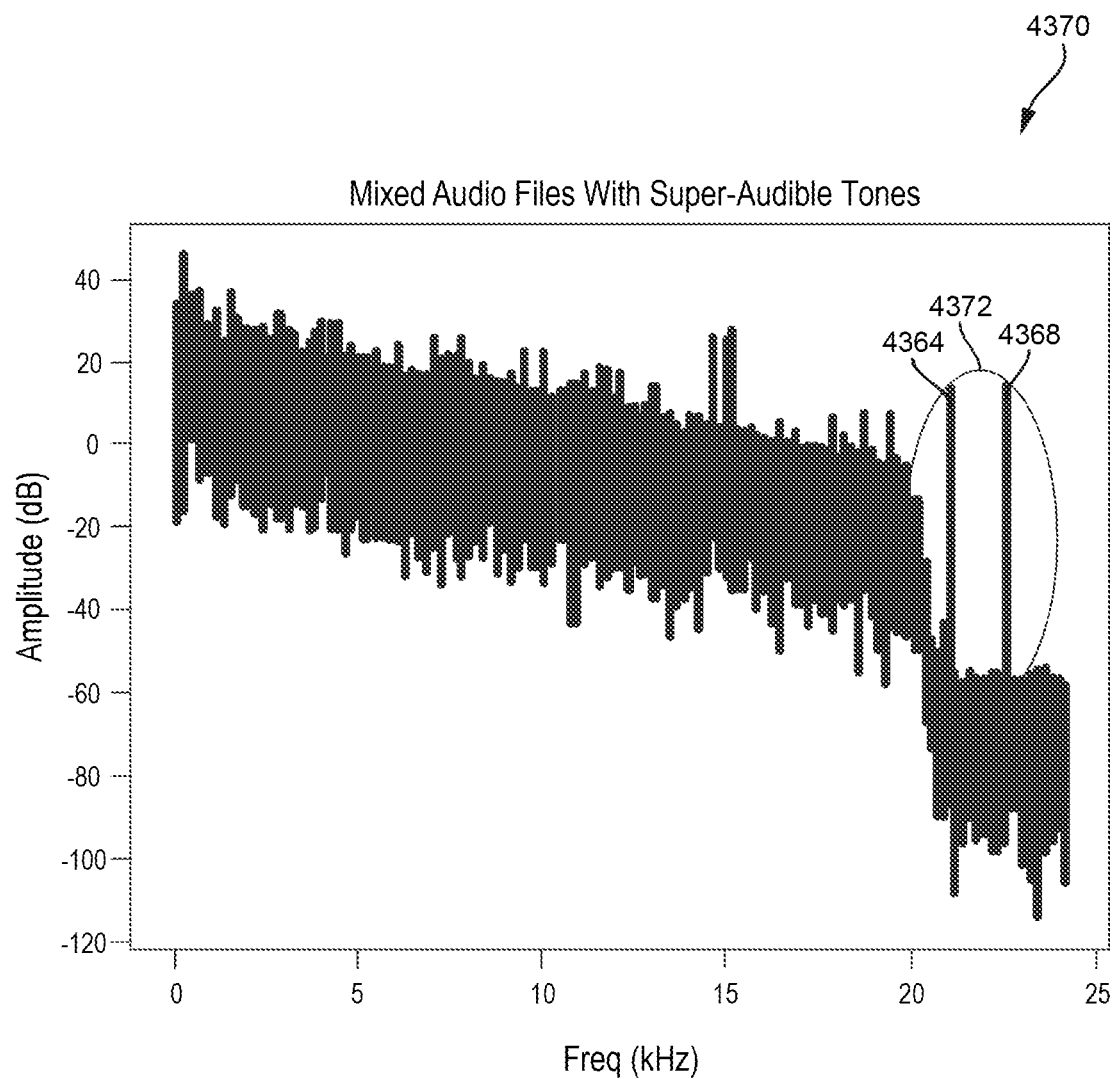
FIG. 35 is a graph of a frequency spectrum of a mixed audio file with super-audible tones.

FIG. 35 is a graph of a frequency spectrum of a mixed audio file 4370 with super-audible tones 4372. The mixed audio file 4370 is produced by mixing the first and second audio files 4362, 4366 (FIGS. 33, 34) each with a single super-audible tone 4364, 4368, respectively. The first and second audio files 4362, 4366 are mixed in the energy module 2004 to produce the mixed audio file 4370 when simultaneous audio is required. The unique super-audible tones 4364, 4368 remain in the frequency spectrum.

Figure 36:
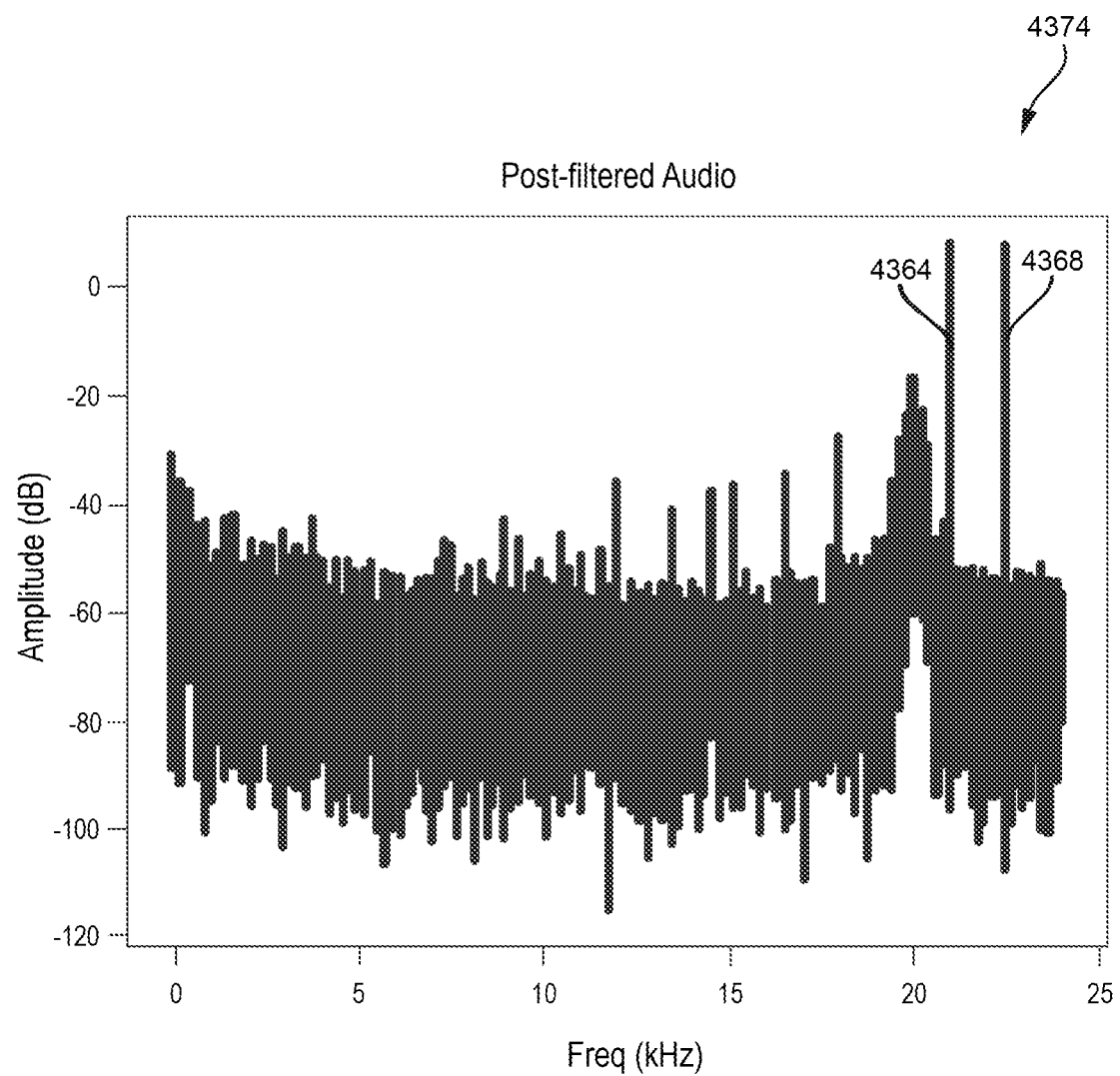
FIG. 36 is a graph of a frequency spectrum of a post filtered mixed audio file.

FIG. 36 is a graph of a frequency spectrum of a post filtered mixed audio file 4374. The mixed audio file 4370 (FIG. 35) is captured either on its way to the amplifier or is current sensed by a current sense amplifier and is band-pass filtered to isolate the target super-audible band comprising the super-audible tones 4364, 4368.

Figure 37:
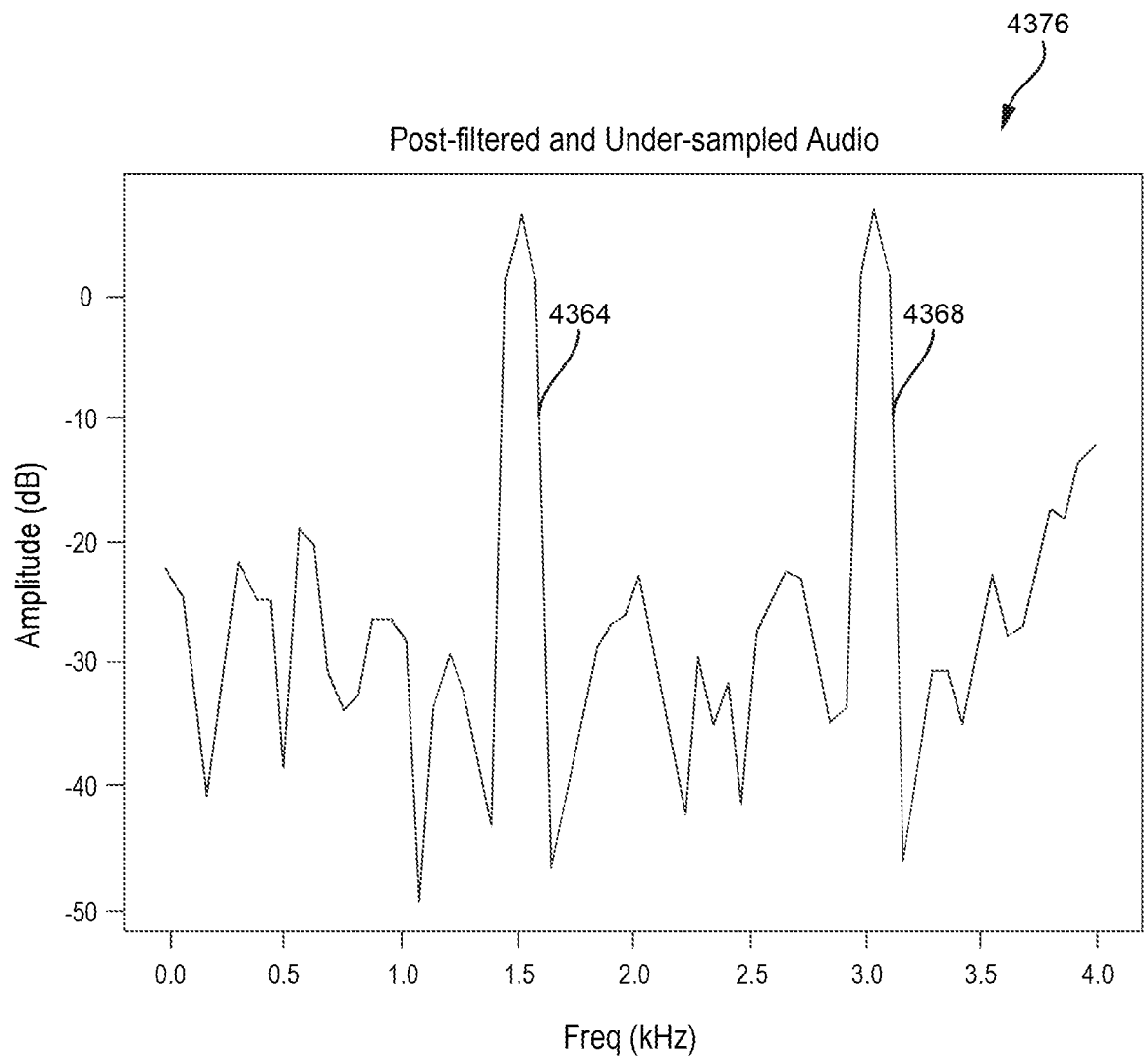
FIG. 37 is a graph of a frequency spectrum of a post-filtered and under-sampled audio file.

FIG. 37 is a graph of a frequency spectrum of a post-filtered and under-sampled audio file 4376. The post filtered mixed audio file 4374 (FIG. 36) data is under-sampled (decimated) and an FFT of the post filtered mixed audio file 4374 is calculated. The super-audible tones 4364, 4368 show up, after under-sampling, as ((Fs/2)−tone_freq), where Fs is the under-sampling sample rate and tone_freq is the frequency of a given super-audible tone.

Figure 38:
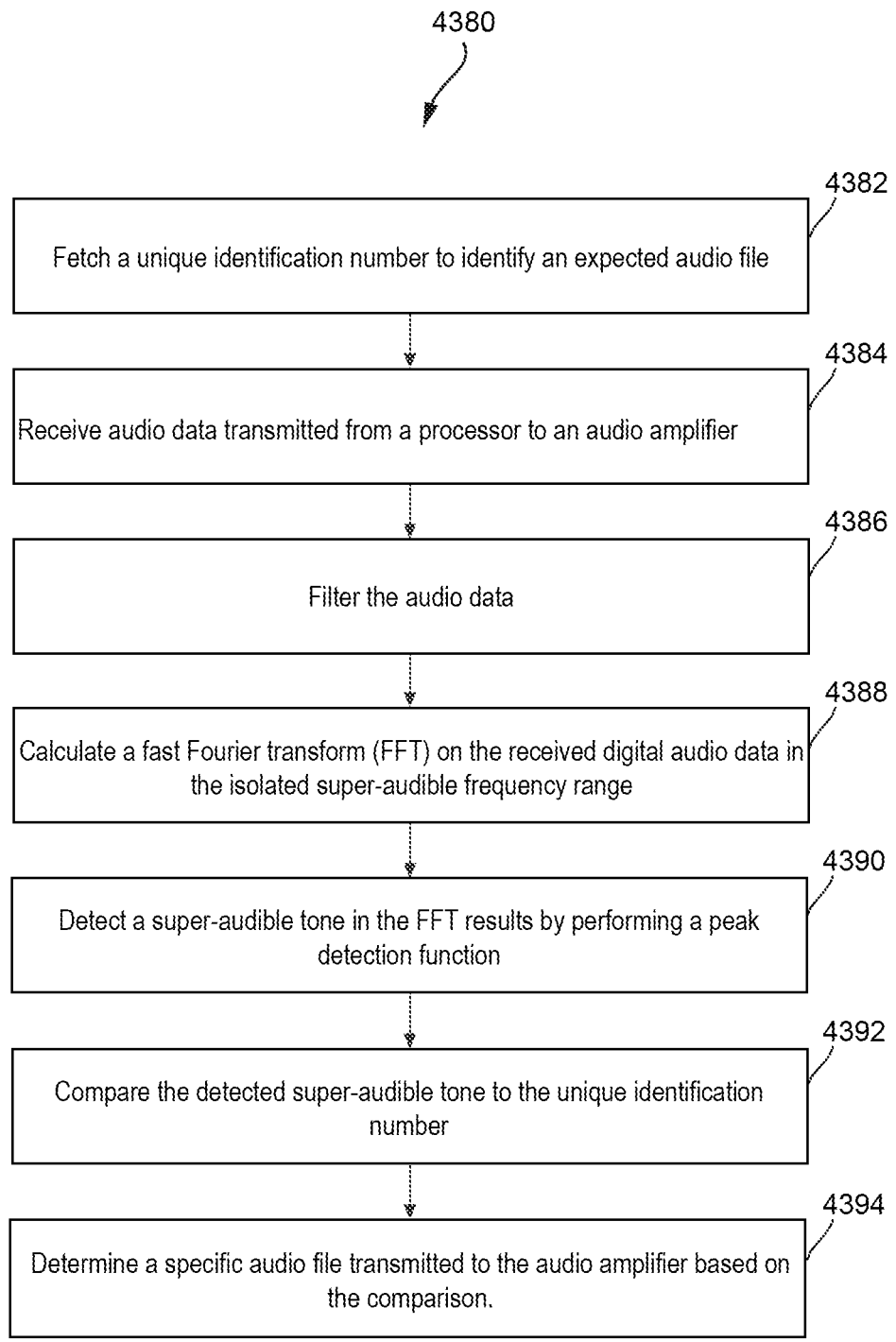
FIG. 38 is a logic diagram of an audio mitigation method using super-audible tones, in accordance with at least one aspect of the present disclosure.

FIG. 38 is a logic diagram of an audio mitigation method 4380 using super-audible tones, in accordance with at least one aspect of the present disclosure. The method 4380 may be implemented with the audio output circuit 4270 shown in FIG. 24. As previously discussed, the audio output circuit 4270 comprises a processor 4202, an audio amplifier 4220 coupled to the processor 4202 by audio data lines, and an audio mitigation control circuit 4276 coupled to the processor 4202 and the audio amplifier 4220. The audio mitigation control circuit 4276 is configured to fetch 4382, from a memory coupled to the audio mitigation control circuit 4276, a unique identification number to identify an expected audio file, the audio file comprising audio data, such as for example the serial double data signal 4264 shown in FIG. 23. The audio data comprises an audio asset, e.g., the serial data signal 4254 represented as a series of data bits 4252 (10011011), and a unique super-audible tone, e.g., the unique tone identification data bits (11000001) (shown uncircled in FIG. 23) inserted between the audio data bits 4252 (10011011) to form a unique series of data bits 4262 (1101001010001011), to identify the audio asset.

According to the method 4380, the audio mitigation control circuit 4276 is configured to receive 4384 the audio data 4264 transmitted from the processor 4202 to the audio amplifier 4220. The audio data is filtered 4386 by the filters 4226, 4228 to isolate a super-audible frequency range of the audio data. In various aspects, the filters 4226, 4228 may be implemented as band-pass filters or high-pass filters. The filtered audio data is sensed by the current amplifiers 4222, 4224 and converted to digital data by the ADCs 4216, 4218 and read by the audio mitigation control circuit 4276. The audio mitigation control circuit 4276 is further to configured to calculate 4388 a fast Fourier transform (FFT) on the received digital audio data in the isolated super-audible frequency range. The audio mitigation control circuit 4276 is further to configured to detect 4390 a super-audible tone in the FFT results by performing a peak detection function. The audio mitigation control circuit 4276 is further configured to compare 4392 the detected super-audible tone to the unique identification number, e.g., the unique tone identification data bits (11000001) (shown un-circled in FIG. 23) inserted between the audio data bits 4252 (10011011) to form a unique series of data bits 4262 (1101001010001011), to identify the expected audio file and determine 4394 a specific audio file transmitted to the audio amplifier 4220 based on the comparison.

In various other aspect, the audio mitigation control circuit 4276 is further configured to under-sample the filtered audio data down to baseband and calculate a fast Fourier transform (FFT) on the under-sampled filtered audio data.

In one aspect, the audio assets may be divided into 50 Hz bins to produce a total of 80 unique identification numbers. In another aspect, the audio assets may be divided into 31.49 Hz bins to produce 256 unique identification numbers.

In one aspect, the audio mitigation control circuit 4276 may be configured to detect a mismatch between the expected audio file and the specific audio file transmitted to the audio amplifier and present a fault to a user interface, cease surgical functions based on the detected mismatch between the expected audio file and the specific audio file transmitted to the audio amplifier, or prevent surgical functions based on the detected mismatch between the expected audio file and the specific audio file transmitted to the audio amplifier.

EXAMPLES

Various aspects of modular energy systems comprising user interface mitigation techniques described herein with reference to FIGS. 22-38 are set out in the following numbered examples.

Example 1. An audio circuit, comprising: a processor configured to generate a digital audio signal, wherein the audio signal comprises audio data bits inserted on the rising edge of a clock signal and additional data bits inserted on a falling edge of the clock signal, wherein the audio data bits on the rising edge represent a digital audio tone and the additional data bits inserted on the falling edge represent a unique tone identification of the audio data bits on the rising edge; a digital-to-analog converter configured to: receive the digital audio signal; convert the audio data bits inserted on the rising edge; and ignore the additional data bits on the falling edge; an audio mitigation control module configured to: receive the digital audio signal; read the additional data bits on the falling edge; and confirm that the audio data bits inserted on the rising edge represent a correct digital audio tone based on the unique tone identification.

Example 2. The audio circuit of Example 1, wherein the audio mitigation control module is implemented in any one of software or hardware or a combination of software and hardware.

Example 3. The audio circuit of any one or more of Examples 1 through 2, further comprising an amplifier circuit coupled to the digital-to-analog converter.

Example 4. The audio circuit of any one or more of Examples 1 through 3, wherein the digital-to-analog converter comprises two analog output channels, wherein a first analog output channel is coupled to a first speaker and as second analog output channel is coupled to a second speaker.

Example 5. The audio circuit of Example 4, further comprising: a first current shunt coupled in series with the first speaker; and a second current shunt coupled in series with the second speaker.

Example 6. The audio circuit of Example 5, comprising: a first current sense amplifier having an input coupled to the first current shunt and an output coupled to an input of a first analog-to-digital converter (ADC); and a second current sense amplifier having an input coupled to the second current shunt and an output coupled to an input of a second ADC; wherein each output of the first and second ADCs is coupled to the audio mitigation control module.

Example 7. A circuit for mitigating a function of a user interface (UI) display of a modular energy system, the circuit comprising: a processor configured to couple to a surgical instrument; a display; and a video data converter circuit configured to receive formatted video data that represents an expected image to be displayed on the display and to provide differential video signaling data to the display and a copy of the differential video signaling data to the processor; wherein the processor is configured to determine whether the copy of the differential video signaling data is changing over time.

Example 8. The circuit of Example 7, wherein the video data converter circuit comprises an input channel coupled to the processor and first and second output channels; wherein the input channel is configured to receive the formatted video data from the processor; wherein the first output channel is coupled to the display to provide differential video signaling data to the display; and wherein the second output channel is coupled to the processor to provide the copy of the differential video signaling data to the processor.

Example 9. The circuit of Example 8, further comprising a second processor coupled to the second output channel, wherein the second processor is different from the processor; wherein the second output channel is configured to provide a copy of the differential video signaling data to the second processor; and wherein the second processor is configured to determine whether the differential video signaling data on the second output channel is changing over time.

Example 10. The circuit of any one or more of Examples 7 through 9, further comprising a video splitter circuit having an input channel and first and second output channels; wherein the video data converter circuit comprises an input channel coupled to the processor and an output channel coupled to the video splitter circuit; wherein the first output channel of the video splitter circuit is coupled to the display to provide differential video signaling data to the display; and wherein the second output channel of the video splitter circuit is coupled to the processor to provide the copy of the differential video signaling data to the processor.

Example 11. The circuit of Example 10, further comprising a second processor coupled to the second output channel of the video splitter circuit, wherein the second processor is different from the processor; wherein the second output channel of the video splitter circuit is configured to provide a copy of the differential video signaling data to the second processor; and wherein the second processor is configured to determine whether the differential video signaling data on the second output channel is changing over time.

Example 12. The circuit of any one or more of Examples 7 through 11, wherein the formatted video data is DisplayPort formatted data.

Example 13. The circuit of any one or more of Examples 7 through 12, wherein the video data converter is configured to convert the formatted video data to low voltage differential signaling data.

Example 14. The circuit of any one or more of Examples 7 through 13, wherein the video data converter circuit comprises a driver circuit coupled to a bridge circuit.

Example 15. The circuit of any one or more of Examples 7 through 14, wherein the processor is configured to reconstruct an image based on the differential video signaling data on the second output channel.

Example 16. The circuit of Example 15, wherein the processor is configured to: compare the reconstructed image to the expected image; and enable activation of the surgical instrument based on a match between the reconstructed image and the expected image.

Example 17. The circuit of any one or more of Examples 15 through 16, wherein the processor is configured to: compare the reconstructed image to the expected image; and disable activation of the surgical instrument based on a mismatch between the reconstructed image and the expected image.

Example 18. The circuit of any one or more of Examples 7 through 17, wherein the processor is configured to disable activation of the surgical instrument based on the differential video signaling data on the second output channel not changing over time when expected.

Example 19. A method of mitigating a function of a user interface (UI) display of a modular energy system, the method comprising: receiving, by a video data converter circuit, formatted video data at an input channel of the video data converter circuit, wherein the input channel is coupled to a processor and the formatted video data represents an expected image to be displayed on a display, the video data converter having two output channels, wherein a first output channel is coupled to the display and a second output channel is coupled back to the processor, wherein the processor is configured to couple to a surgical instrument; providing, by the video data converter circuit, differential video signaling data to the display from the first output channel of the video data converter circuit; providing, by the video data converter circuit, a copy of the differential video signaling data to the processor from the second output channel; and determining, by the processor, whether the differential video signaling data on the second output channel is changing over time.

Example 20. The method of Example 19, comprising reconstructing, by the processor, an image based on the differential video signaling data on the second output channel.

Example 21. The method of Example 20, comprising: comparing, by the processor, the reconstructed image to the expected image; and enabling, by the processor, activation of the surgical instrument based on a match between the reconstructed image and the expected image.

Example 22. The method of any one or more of Examples 20 through 21, comprising: comparing, by the processor, the reconstructed image to the expected image; and disable, by the processor, activation of the surgical instrument based on a mismatch between the reconstructed image and the expected image.

Example 23. The method of any one or more of Examples 19 through 22, comprising disabling, by the processor, activation of the surgical instrument based on the differential video signaling data on the second output channel not changing over time when expected.

Example 24. An audio circuit, comprising: a processor; an audio amplifier coupled to the processor by audio data lines; an audio mitigation control circuit coupled to the processor and the audio amplifier, a digital-to-analog converter (DAC) comprising a first analog output channel coupled to a first speaker; a first current shunt coupled in series with the first speaker; a first current sense amplifier having an input coupled to the first current shunt and an output coupled to an input of a first analog-to-digital converter (ADC); and wherein the output of the first ADC is coupled to the audio mitigation control module; wherein the audio mitigation control circuit is configured to: fetch, from a memory coupled to the audio mitigation control circuit, a unique identification number to identify an expected audio file, the audio file comprising audio data comprising an audio asset and a unique super-audible tone to identify the audio asset; receive the audio data from the output of the first ADC; filter the audio data to isolate a super-audible frequency range of the audio data; calculate a fast Fourier transform (FFT) on the audio data in the isolated super-audible frequency range; perform a peak detection function on the FFT results to detect a super-audible tone; compare the detected super-audible tone to the unique identification number to identify the expected audio file; and determine a specific audio file transmitted to the audio amplifier based on the comparison.

Example 25. The audio circuit of Example 24, wherein the audio mitigation control circuit is configured to under-sample the filtered audio data down to baseband.

Example 26. The audio circuit of Example 25, wherein the audio mitigation control circuit is configured to calculate a fast Fourier transform (FFT) on the under-sampled filtered audio data.

Example 27. The audio circuit of any one or more of Examples 24 through 26, wherein the audio assets are divided into 50 Hz bins to produce a total of 80 unique identification numbers.

Example 28. The audio circuit of any one or more of Examples 24 through 27, wherein the audio assets are divided into 31.49 Hz bins to produce 256 unique identification numbers.

Example 29. The audio circuit of any one or more of Examples 24 through 28, wherein the audio mitigation control circuit is configured to detect a mismatch between the expected audio file and the specific audio file transmitted to the audio amplifier and present a fault to a user interface.

Example 30. The audio circuit of Example 29, wherein the audio mitigation control circuit is configured to cease surgical functions based on the detected mismatch between the expected audio file and the specific audio file transmitted to the audio amplifier.

Example 31. The audio circuit of any one or more of Examples 29 through 30, wherein the audio mitigation control circuit is configured to prevent surgical functions based on the detected mismatch between the expected audio file and the specific audio file transmitted to the audio amplifier.

Example 32. The audio circuit of any one or more of Examples 24 through 31, wherein the filter is implemented as a band-pass filter.

Example 33. The audio circuit of any one or more of Examples 24 through 32, wherein the filter is implemented as a high-pass filter.

Example 34. The audio circuit of any one or more of Examples 24 through 33, wherein the DAC comprises a second analog output channel; the audio circuit further comprising: a second speaker coupled to the second analog channel of the DAC; a second current shunt coupled in series with the second speaker; a second ADC; a second current sense amplifier having an input coupled to the second current shunt and an output coupled to an input of the second ADC; wherein the output of the second ADC is coupled to the audio mitigation control module; and wherein the audio mitigation control circuit is configured to receive the audio data from the output of the second ADC.

Example 35. An audio circuit, comprising: a processor; an audio amplifier coupled to the processor by audio data lines; an audio mitigation control circuit coupled to the processor and the audio amplifier, wherein the audio mitigation control circuit is configured to: fetch, from a memory coupled to the audio mitigation control circuit, a unique identification number to identify an expected audio file, the audio file comprising audio data comprising an audio asset and a unique super-audible tone to identify the audio asset; receive the audio data transmitted from the processor to the audio amplifier; filter the audio data to isolate a super-audible frequency range of the audio data; calculate a fast Fourier transform (FFT) on the audio data in the isolated super-audible frequency range; perform a peak detection function on the FFT results to detect a super-audible tone; compare the detected super-audible tone to the unique identification number to identify the expected audio file; and determine a specific audio file transmitted to the audio amplifier based on the comparison.

Energy Delivery Mitigations for Modular Energy Systems

Having described a general implementation of modular energy systems 2000, 3000, and 6000, and various surgical instruments usable therewith, for example, surgical instruments 2204, 2206, and 2208, the disclosure now turns to various aspects of modular energy systems comprising energy delivery mitigations. In other aspects, these modular energy systems are substantially similar to the modular energy system 2000, the modular energy system 3000, and/or the modular energy system 6000 described hereinabove. For the sake of brevity, various details of other modular energy systems described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

Mitigated Interface for Energy Footswitch Activation

As described hereinbelow with reference to FIG. 39, in various aspects, the present disclosure provides modular energy systems 2000, 3000, 6000 comprising a mitigated interface for energy footswitch activation. In general terms throughout the present disclosure, coupled refers to wireless or wired connections between two components. For illustrative purposes and not limitations, the accessory described in this context is a footswitch that is used to activate energy to an electrosurgical/ultrasonic instrument. As used herein, electrosurgical/ultrasonic instrument comprises any one of an electrosurgical instrument that is either monopolar or bipolar, an ultrasonic instrument, or an instrument that employs a combination of electrosurgical and ultrasonic energy, connected to the energy module 2004, 3004, 6004 of the modular energy system 2000, 3000, 6000. Accordingly, in one aspect, the accessory may comprise one or more than one footswitch configured to activate an electrosurgical/ultrasonic instrument by communicating switch states to the modular energy module 2000, 3000, 6000. In one aspect, the mitigated interface detects the state of each coupled footswitch, or other accessory, as well as the type of footswitch, or other accessory, that is coupled to the modular energy system 2000, 3000, 6000. In another aspect, the present disclosure provides a robust wireless mesh communication network to improve the reliability of wireless communications between accessories and the modular energy system 2000, 3000, 6000 in an operating room (OR) environment.

In one aspect, the present disclosure provides a modular energy system 2000, 3000, 6004 comprising a header module 2002, 3002, 6002 and at least one energy module 2004, 3004, 6004 with support for multiple footswitches and footswitch types to control the activation of electrosurgical/ultrasonic instruments connected to the energy module 2004, 3004, 6004. In one aspect, to accommodate support for multiple footswitches and footswitch types, an isolated interface is disposed between a host controller in the header module 2002, 3002, 6002 and the footswitch ports into which the footswitches are coupled to the header module 2002, 3002, 6002. The isolated interface detects the state of the connected footswitch as well as the type of connected footswitch. The isolated interface comprises isolation circuitry, which is typically physically large and costly. Therefore, it is desirable to minimize the number of discrete signals crossing the isolation boundary to minimize the number of isolation circuitry required in a given application. It is also desirable to provide mitigation techniques at the isolated interface to minimize the probability that an energy device such as an electrosurgical/ultrasonic instrument receives an uncommanded erroneous activation signal from the accessory.

Figure 39:
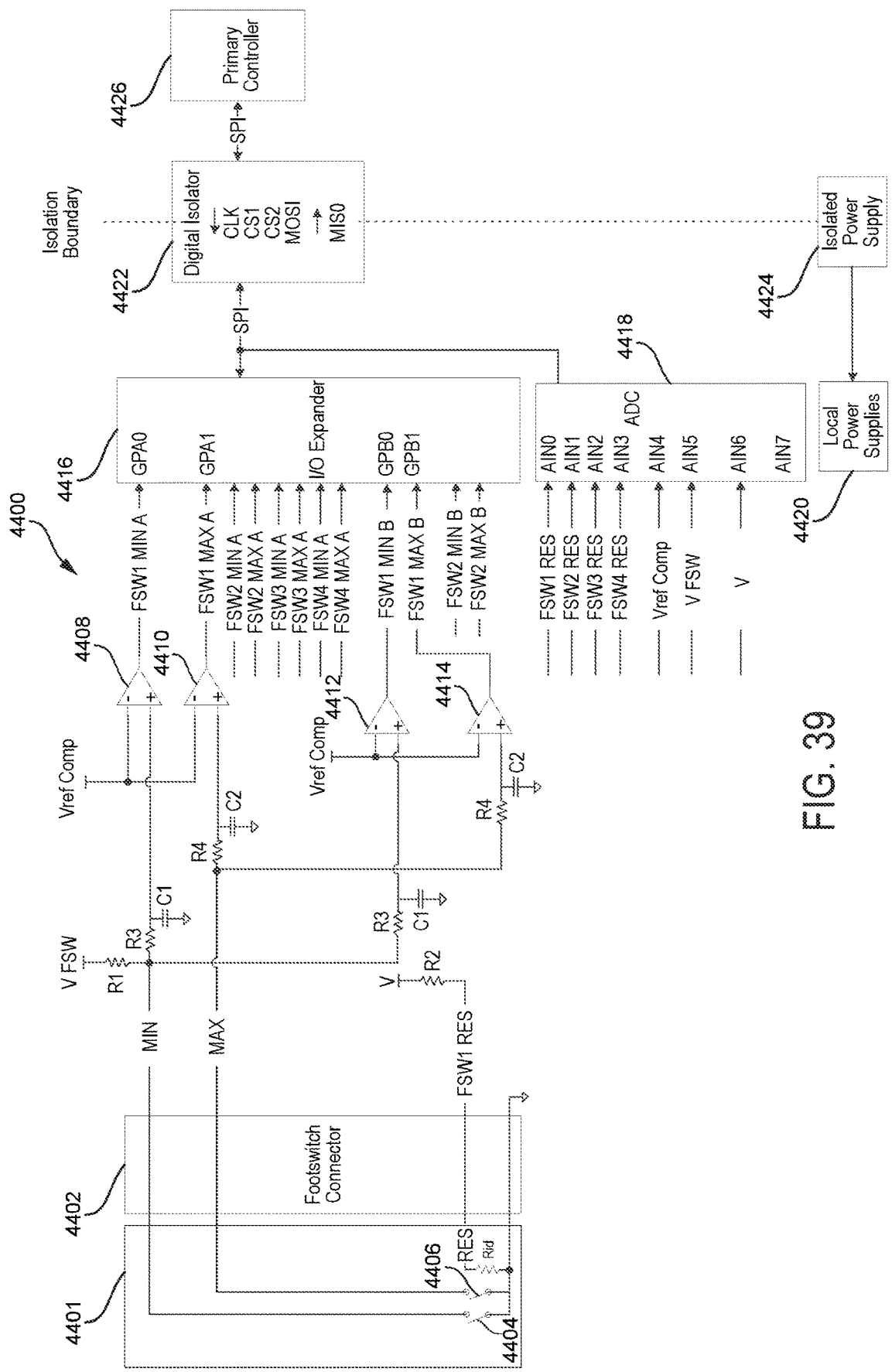
FIG. 39 is a schematic diagram of an isolated footswitch interface circuit to support and mitigate footswitch activation for multiple footswitches and types of footswitches, in accordance with at least one aspect of the present disclosure.

FIG. 39 is a schematic diagram of an isolated switch interface circuit 4400 to support and mitigate footswitch activation for multiple footswitches and types of footswitches, in accordance with at least one aspect of the present disclosure. The isolated switch interface circuit 4400 comprises a footswitch 4401 coupled to a footswitch connector 4402. In one aspect, the footswitch 4401 comprises a minimum (MIN) switch 4404 and a maximum (MAX) switch 4406 output. A footswitch identification circuit comprising, for example, a resistor "R id" is used to identify the type of footswitch 4401 coupled to the footswitch connector 4402. It will be appreciated that, although the present examples is directed to a footswitch, the isolated switch interface circuit 4400 may be adapted for any switch used to control activation or deactivation of a surgical instrument coupled to the energy module 2004 of a modular energy system 2000.

The MIN switch 4404 is coupled through the footswitch connector 4402 to a first footswitch detection circuit comprising a first comparator 4408. The MAX switch 4406 is coupled through the footswitch connector 4402 to a second comparator 4410. A reference voltage Vref Comp is applied to each of the first and second comparators 4408, 4410. The voltage signals generated by closing or opening the MIN and MAX switches 4404, 4406 are compared to the reference voltage Vref Comp at the respective inputs of the first and second comparators 4408, 4410. The output FSW1 MIN A of the first comparator 4408 and the output FSW1 MAX A of the second comparator 4410 are applied to an input/output (I/O) expander circuit 4416. The FSW1 RES voltage signal is used to identify the type of footswitch 4401 coupled to the footswitch connector 4402 is applied to an input of an analog-to-digital converter (ADC) circuit 4418.

The MIN switch 4404 is also coupled through the footswitch connector 4402 to a duplicate footswitch detection circuit comprising a third comparator 4412. The MAX switch 4406 is also coupled through the footswitch connector 4402 to a duplicate footswitch detection circuitry comprising a fourth comparator 4414. A reference voltage Vref Comp is applied to each of the third and fourth comparators 4412, 4414. The voltage signals generated by closing or opening the MIN and MAX switches 4404, 4406 are compared to the reference voltage Vref Comp at the respective inputs of the third and fourth comparators 4412, 4414. The output FSW1 MIN B of the first comparator 4412 and the output FSW1 MAX B are applied to the I/O expander circuit 4416. The duplicate footswitch detection circuitry mitigates energy footswitch activation to a surgical instrument coupled to the energy module 2004, 3004, 6004. It will be appreciated that the duplicate footswitch detection circuitry mitigates against potential failures in the detection circuitry.

The output of the I/O expander circuit 4416 is connected to a digital isolator circuit 4422 and to a primary controller 4426 over a serial peripheral interface (SPI), e.g., single digital serial communication bus. The primary controller 4426 comprises a processor. The primary controller 4426 compares the outputs of the first and second footswitch detection circuits and either activates or deactivates energy to the surgical instrument coupled to the energy module 2004 based on the results of the comparison. For example, the primary controller 4426 will activate or deactivate if the outputs of the first and second footswitch detection circuits match. If there is a mismatch between the outputs of the first and second footswitch detection circuits, the primary controller 4426 will deactivate energy to the surgical instrument. In the instance where the first and second footswitch detection circuits each include a single comparator 4408 and a duplicate comparator 4412, the primary controller 4426 compares the outputs of the single comparator 4408 and the duplicate comparator 4412.

In the instance where the first and second footswitch detection circuits each include multiple comparators such as a first and second comparator 4408, 4410 and first and second duplicate comparators 4412, 4414, the primary controller 4426 compares the outputs of the first comparator 4408 with the first duplicate comparator 4412 and compares the output of the second comparator 4410 with the second duplicate comparator 4414. This process may be scaled up to a predetermined number of footswitches and corresponding number of comparators and duplicate comparators. In this manner, the primary controller 4426 can mitigate the risk of any given footswitch signal by comparing the outputs of the primary comparators to the corresponding duplicate comparators.

As shown in FIG. 39, the digital isolator circuit 4422 defines an isolation boundary between the primary controller 4426 and the isolated switch interface circuit 4400. An isolated power supply 4424 supplies power to the local power supplies 4420 of the isolated switch interface circuit 4400.

Still with reference to FIG. 39, additional footswitches FSW2, FSW3, FSW4, and others, can be added to the isolated switch interface circuit 4400. These additional footswitches FSW2, FSW3, FSW4, and others, are coupled to the I/O expander circuit 4416 and to the primary controller 4426 over the SPI bus and through the digital isolator circuit 4422. The ID resistor values FSW2 RES, FSW3 RES, FSW4 RES, and others, identify the type of footswitches FSW2, FSW3, FSW4, and others. In one aspect, the ID resistor values FSW1 RES, FSW2 RES, FSW3 RES, FSW4 RES are applied to the ADC circuit 4418 in the form of voltages. In other implementations, currents or other parameters may be applied to the ADC circuit 4418 to identify the type of footswitches. The ADC circuit 4418 is coupled to the primary controller 4426 over the SPI bus and through the digital isolator circuit 4422. The signal Vref_Comp is provided as input to the ADC circuit 4418. The Vref_Comp signal is provided to the input of the ADC circuit 4418 such that the primary controller 4426 can perform a self-test of the comparator reference voltage Vref_Comp.

The disclosed I/O expander circuit 4416 and the ADC circuit 4418 are connected on the single SPI bus. The ADC circuit 4418 monitors a resistor value FSW1 RES integrated into each attached footswitch 4401 for detecting unique footswitch types. The I/O expander circuit 4416 monitors the MIN state and the MAX state of each footswitch 4401. Employing the I/O expander circuit 4416 with greater than or equal to twice the number of required I/O, the footswitch states MIN, MAX can be mitigated by duplicating the detection circuitry. Accordingly, the isolated switch interface circuit 4400 detects the switch state of each connected footswitch 4401 as well as the type of footswitch 4401 connected. The isolated switch interface circuit 4400 minimizes the number of discrete signals crossing the isolation boundary as isolation circuitry is typically physically large and costly. Further, the isolated switch interface circuit 4400 provides mitigation techniques on the interface to minimize the probability that an energy device receives an uncommanded activation. Accordingly, using a single digital, serial communication bus SPI for bridging across the isolation boundary minimizes the number of signals required by the isolated switch interface circuit 4400. This technique minimizes the number of discrete signals crossing the isolation boundary to minimize the isolation circuitry required in a given application and simplifies the implementation.

In one aspect, the present disclosure provides a method of mitigating erroneous outputs from an isolated footswitch interface circuit 4400 for a modular energy system 2000. The method comprises receiving, at a first input of a first comparator 4408, a state of a first switch 4404 of a first footswitch 4401 coupled to the first input of the first comparator 4408 and a reference voltage Vref_Comp coupled to a second input of the first comparator 4408. The method comprises, receiving, at a first input of a first duplicate comparator 4412, the state of the first switch 4404 coupled to the first input of the first duplicate comparator 4412 and the reference voltage Vref_Comp coupled to a second input of the first duplicate comparator 4412. The method comprises comparing, by the controller 4426 coupled to the outputs of the first comparator 4408 and the first duplicate comparator 4412, the output of the first comparator 4408 with the output of the first duplicate comparator 4412. The method comprises determining, by the controller 4426, activation or deactivation of a surgical instrument coupled to the controller 4426 based on the comparison.

The method further comprises receiving, by an analog to digital converter 4418 (ADC) coupled to the controller 4426, a first footswitch identification signal FSW1 RES and identifying, by the controller 4426, a type of the footswitch 4401 based on the first switch identification signal FSW1 RES. In another aspect, the method further comprises the primary controller 4426 measuring the "Vref Comp" voltage and determining that it is within its expected range by measuring the voltage at the ADC 4418 input.

The method further comprises receiving, at a first input of a second comparator 4410, a state of a second switch 4406 of the first footswitch 4401 coupled to the first input of the second comparator 4410 and a reference voltage Vref Comp coupled to a second input of the second comparator 4410. The method comprises, receiving, at a first input of a second duplicate comparator 4414, the state of the second switch 4406 coupled to the first input of the second duplicate comparator 4414 and the reference voltage Vref Comp coupled to a second input of the second duplicate comparator 4414. The method comprises comparing, by the controller 4426 coupled to outputs of the second comparator 4410 and the second duplicate comparator 4414, the output of the second comparator 4410 with the output of the second duplicate comparator 4414.

The method further comprises determining, by the controller 4426, activation or deactivation of a surgical instrument coupled to the controller 4426 based on the comparison. In one aspect, the method comprises receiving, by the ADC 4418, a comparator reference voltage Vref Comp and measuring, by the controller 4426, the comparator reference voltage Vref Comp applied to the ADC 4418. The method further comprises determining, by the controller 4426, that the comparator reference voltage Vref Comp is within predetermined limits and enabling, by the controller 4426, activation of the surgical instrument in the instance that the comparator reference voltage Vref Comp is within the predetermined limits and disabling, by the controller 4426, activation of the surgical instrument in the instance that the comparator reference voltage Vref Comp is not within the predetermined limits.

In other aspects, the mitigation method further comprises mitigating the circuitry by measuring the voltage rails V and detecting an error if these voltages V are outside an expected range. In one aspect, the ADC 4418 also may receive at its input one or more of the power supply, V and V FSW, for example, and reference voltages, Vref Comp, for example, used by the detection circuitry. In another aspect, the ADC 4418 also may receive at its input one or more of the power supply and reference voltages used by the detection circuitry scaled by a scaling circuitry. Accordingly, in various aspects, the method further comprises receiving, at an input to the ADC 4418, one or more of the power supply V and V FSW and reference voltages Vref Comp used by the detection circuitry, or one or more of the power supply and reference voltages used by the detection circuitry scaled by a scaling circuitry. The method further comprises comparing, by the controller 4426, a measurement of the power supply V and V FSW and reference voltages Vref Comp to an expected range to determine proper operation of the voltage supply circuitries.

Robust Wireless Accessory Communication

As described hereinbelow with reference to FIGS. 40-46, in various aspects, the present disclosure provides modular energy systems 2000, 3000, 6000 comprising robust wireless accessory communication techniques. Wireless communication can potentially be unreliable in an operating room (OR) environment, due to various sources of electromagnetic interference or other sources of interference. For many applications (such as footswitch-activation), a robust method of communicating wirelessly is needed. The present disclosure provides circuits and associated methods for robust wireless accessory communication in an OR environment.

Figure 40:
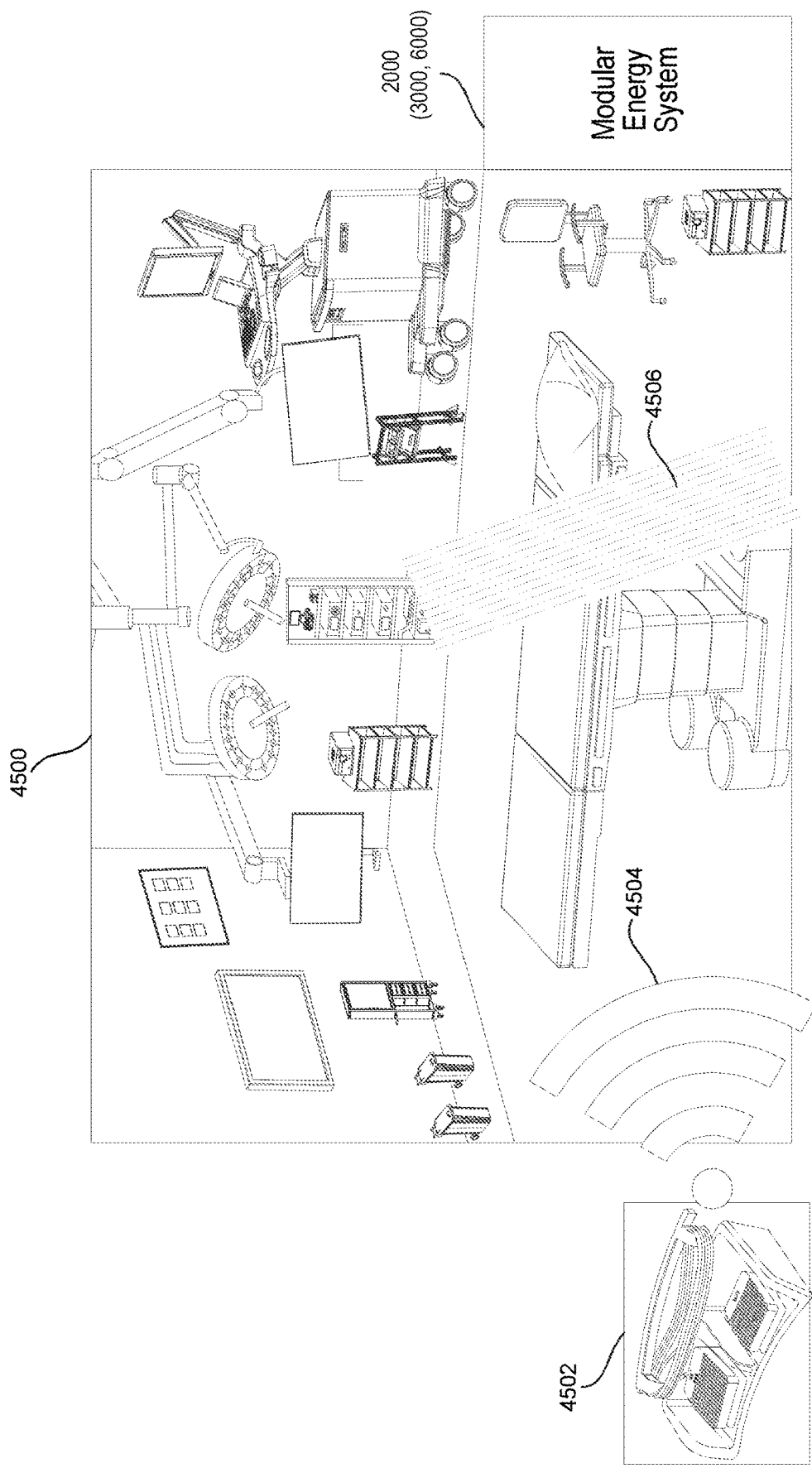
FIG. 40 shows an operating room (OR) with an accessory communicating wirelessly to a modular energy system.

FIG. 40 shows an operating room 4500 (OR) with an accessory communicating wirelessly to a modular energy system 2000, 3000, 6000. In example illustrated in FIG. 40, the accessory is a wireless footswitch 4502 in wireless communication with the modular energy system 2000, 3000, 6000. Interference 4506 in the OR 4500 can block the wireless signals 4504 and may impact the reliability of related communications. For example, wireless signals 4504 transmitted by the footswitch 4502 may not reach the modular energy system 2000, 3000, 6000 to activate or deactivate an electrosurgical/ultrasonic instrument used in an OR procedure. In other aspects, the accessory may comprise multiple footswitches or other devices coupled to the modular energy system 2000, 3000, 6000.

FIG. 41 is a schematic representation of a wireless mesh network 4510, in accordance with at least one aspect of the present disclosure. Those skilled in the art will appreciate that a wireless mesh network (WMN) may be any communications network made up of radio nodes organized in a mesh topology. The WMN can also be implemented in the form of a wireless ad hoc network. A mesh refers to rich interconnection among devices or nodes 1-11. Wireless mesh networks may comprise of mesh clients, mesh routers, and gateways. This differs from typical point-to-point or "star" topologies in that any "node" 1-11 on the mesh 4510 can communicate with one, many, or all other nodes 1-11 on the mesh 4510. In one aspect, the wireless mesh network 4510 may be implemented as a Bluetooth Mesh, a relatively new wireless standard that supports communications in a WMN. Further, nodes 1-11 can "forward" messages to other nodes 1-11 to allow for long-range communication, or for redundant communication paths.

FIG. 42 is a bock diagram of a modular energy system 2000, 3000, 6000 comprising multiple radios 4512, 4516, in accordance with at least one aspect of the present disclosure. Each radio 4512, 4516 is configured to transmit or receive unique wireless signals 4514, 4518, respectively communicated over the wireless mesh network 4510 (FIG. 41).

FIG. 43 is a diagram of a footswitch 4520 comprising multiple radios 4522, 4526, in accordance with at least aspect of the present disclosure. Each radio 4522, 4526 is configured to transmit or receive unique wireless signals 4524, 4528 communicated over the wireless mesh network 4510 (FIG. 41).

With reference to FIGS. 40-43, each accessory in the OR 4500, such as the footswitch 4520 may comprise multiple radios 4522, 4526 to transmit or receive wireless signals 4524, 4528 to communicate with the modular energy system 2000, 3000, 6000 over the wireless mesh network 4510. Each footswitch 4520 radio 4522, 4526 determines the state of the footswitch 4520. Each modular energy system 2000, 3000, 6000 radio 4512, 4516 and footswitch 4520 radio 4522, 4526 defines one or more than one node 1-11 defined by the wireless mesh network 4510. Thus, in the instance of a radio 4512 failure, other radios 4516, 4522, 4526 would be operational in the wireless mesh network 4510. It will appreciated that the modular energy system 2000, 3000, 6000 and the footswitch 4520 may comprise a single radio. Single radio implementation would still provide a benefit to the wireless mesh network 4510 topology to overcome interference 4506 in the OR 4500.

Figure 44:
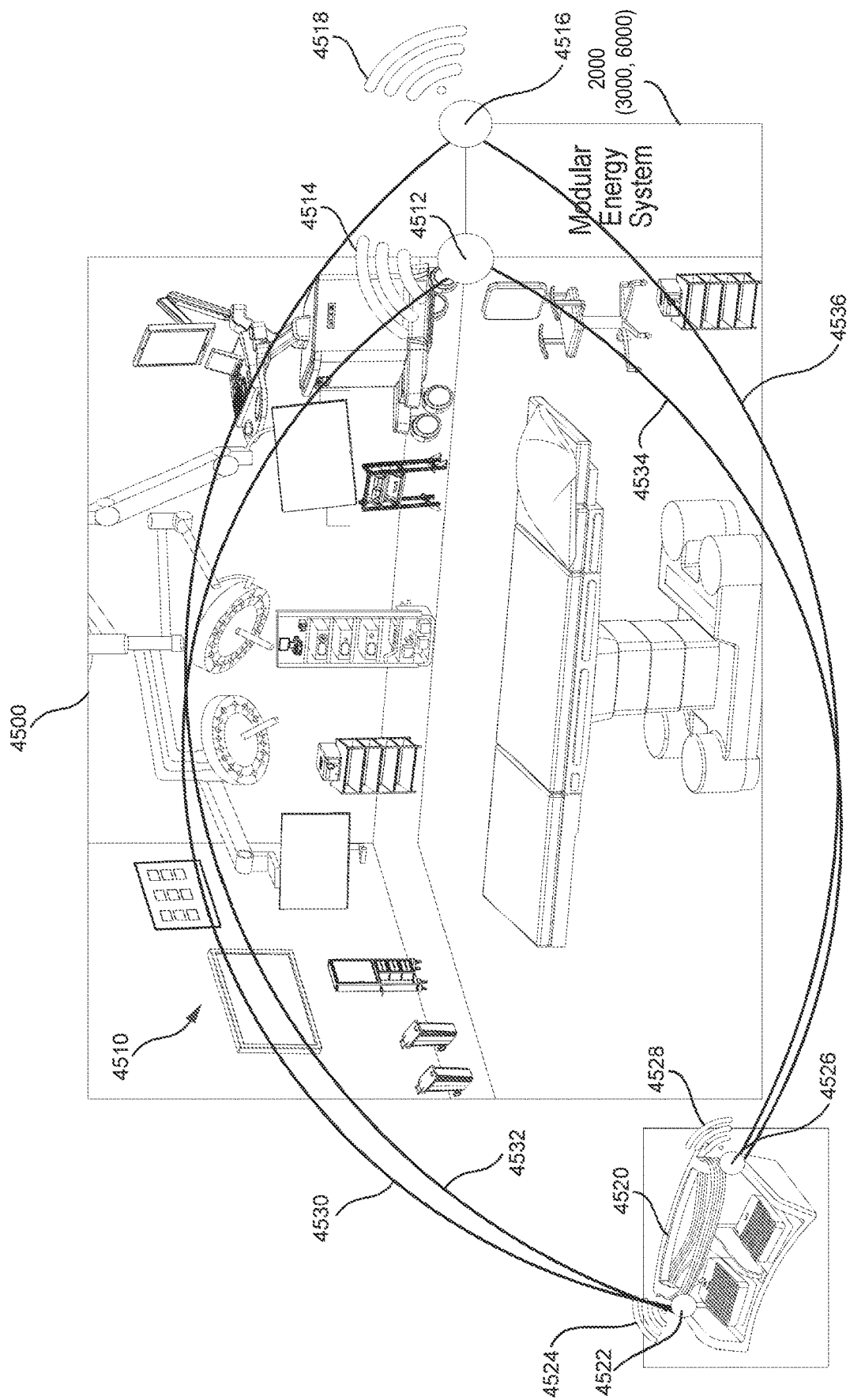
FIG. 44 shows an OR equipped with an accessory communicating wirelessly to a modular energy system over a wireless mesh network implemented by multiple radios, in accordance with at least one aspect of the present disclosure.

FIG. 44 shows an OR 4500 equipped with an accessory communicating wirelessly to a modular energy system 2000, 3000, 6000 over a wireless mesh network 4510 implemented by multiple radios 4512, 4516, 4522, 4526, in accordance with at least one aspect of the present disclosure. In example illustrated in FIG. 44, the accessory is a wireless footswitch 4502 in wireless communication with the modular energy system 2000, 3000, 6000. The wireless mesh network 4510 (e.g., Bluetooth Mesh) comprising multiple nodes 1-11, for example, is implemented with multiple radios 4512, 4516, 4522, 4526, among others, in the modular energy system 2000, 3000, 6000 and footswitch 4530 accessory. The wireless mesh network 4510 topology facilitates the implementation of redundant wireless communication paths 4530, 4532, 4534, 4536, to form a robust wireless accessory communication network. Thus, if a wireless communication path 4530 were to fail, there are three other wireless communication paths 4532, 4534, 4536 still available for reliable communication.

In the example implementation illustrated in FIGS. 42-44, the wireless footswitch 4520 comprises two wireless radios 4524, 4526 defining two mesh nodes, e.g., Bluetooth Mesh nodes, each independently reading the states of the footswitch 4520. This provides full redundancy at the footswitch 4520 level. Further, the modular energy system 2000, 3000, 6000 comprises two wireless radio 4512, 4516 defining two mesh nodes, e.g., Bluetooth Mesh nodes, creating redundancy at the modular energy system 2000, 3000, 6000 level as well. The radios 4512, 4516, 4522, 4526 (e.g., nodes) create redundant wireless communication paths 4530, 4532, 4534, 4536 between the footswitch 4520 and the modular energy system 2000, 3000, 6000.

Figure 45:
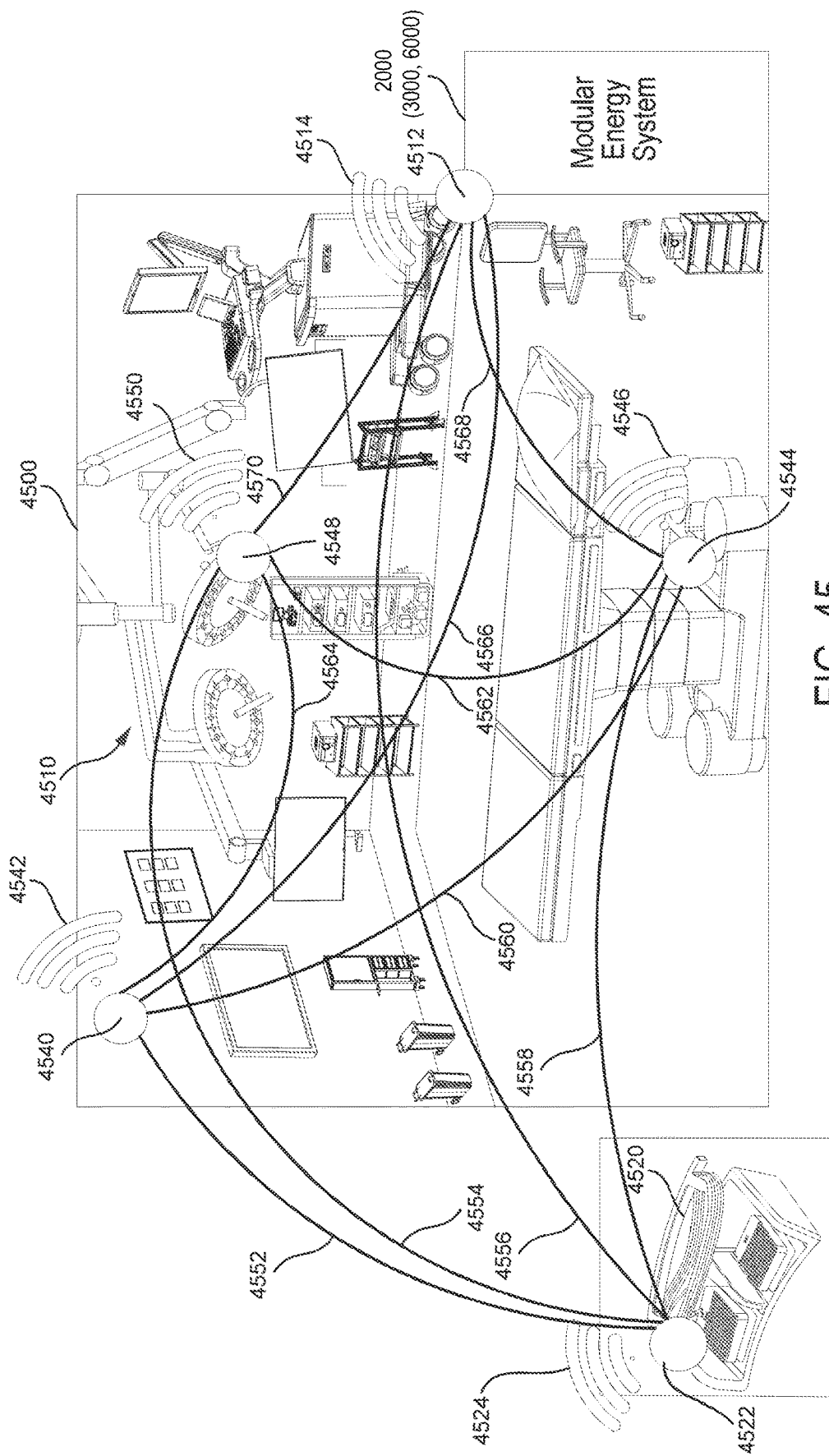
FIG. 45 is an operating room (OR) configured with additional "repeater" nodes optionally be placed around the OR environment to provide a robust wireless mesh network, in accordance with at least one aspect of the present disclosure.

FIG. 45 is an operating room 4500 (OR) configured with additional "repeater" nodes optionally be placed around the OR environment to provide a robust wireless mesh network 4510, in accordance with at least one aspect of the present disclosure. In the example shown in FIG. 45, the footswitch 4520 comprises a single radio 4522 to transmit and receive wireless signals 4525 and defining a wireless node in the wireless mesh network 4510. The modular energy system 2000, 3000, 6000 also comprises a single radio 4512 to transmit and receive wireless signals 4514 and defining another wireless node in the wireless mesh network 4510. To add redundancy to and improve robustness of the wireless mesh network 4510 in the OR 4500, additional nodes may be located in the OR 4550, e.g., underneath a table, on ceiling, etc. These additional nodes 4540, 4544, 4548 each can receive and transmits wireless signals 4542, 4546, 4550, respectively, over redundant wireless communication paths 4552, 4554, 4556, 4558, 4560, 4562, 4564, 4566, 4568, 4570 to forward messages to other nodes, creating redundant nodes in the wireless mesh network 4510 between the footswitch 4520 and the modular energy system 2000, 3000, 6000. The redundant wireless communication paths 4552-4570 result in a redundant wireless mesh network 4510 that is robust to single (or multiple) fault conditions.

The wireless mesh network 4510 shown in FIG. 45 increases the maximum distance between the footswitch 4520 and the modular energy system 2000 and increases redundancy in communication paths 4552, 4554, 4556, 4558, 4560, 4562, 4564, 4566, 4568, 4570. Although the example shown in FIG. 45 shows only one active radio 4522 in the footswitch 4520 and one active radio 4512 in the modular energy system 2000, 3000, 6000, this can be expanded to multiple radios per footswitch 4520 and modular energy system 2000, 3000, 6000.

Figure 46:
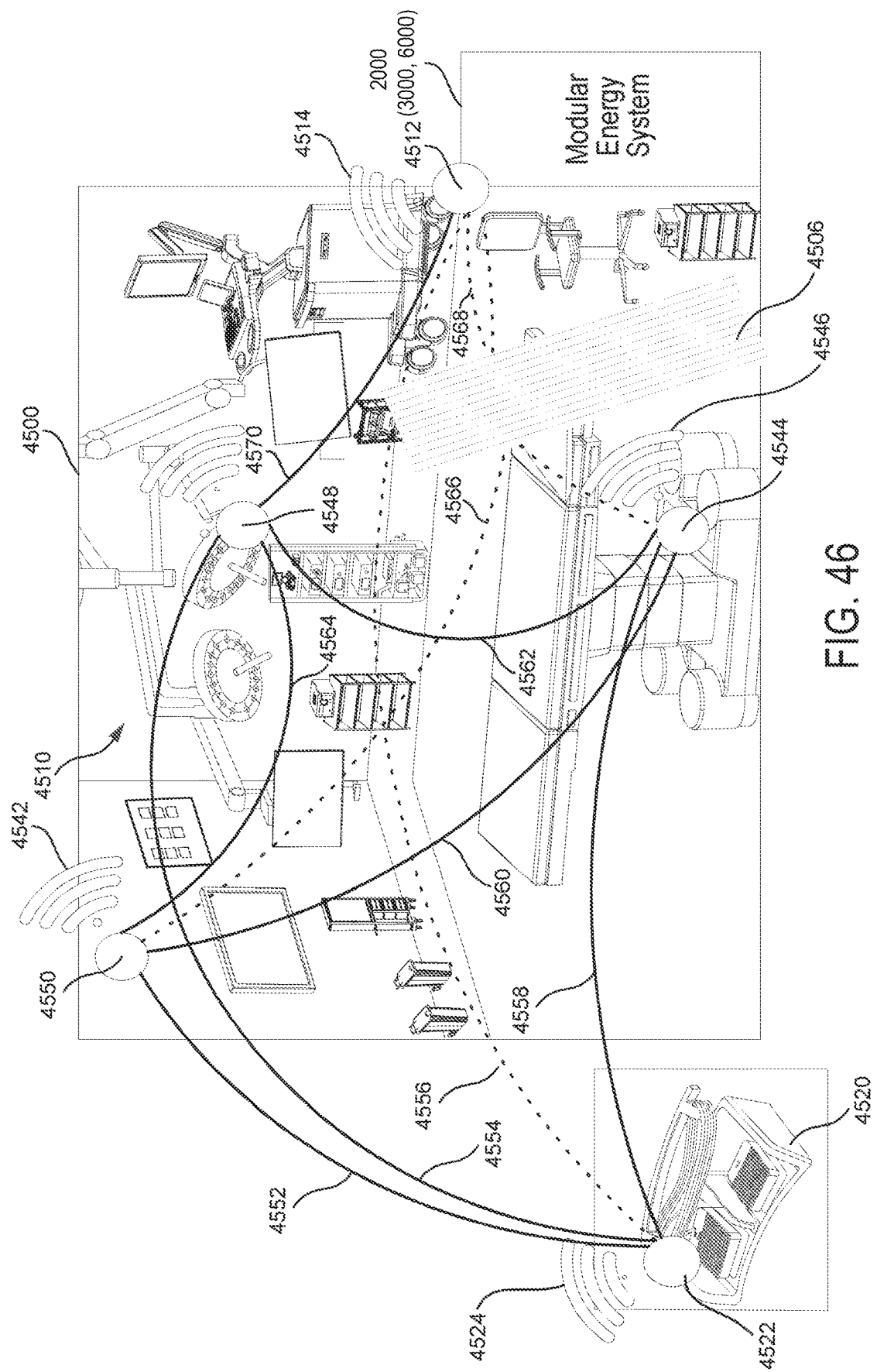
FIG. 46 shows the operating room (OR) shown in FIG. 45 with interference blocking some of the communication paths and communications routed to other nodes in the wireless mesh network, in accordance with at least one aspect of the present disclosure.

FIG. 46 shows the OR 4500 shown in FIG. 45 with interference 4506 blocking some of the communication paths 4556, 4566, 4568 and communications routed to other nodes in the wireless mesh network 4510, in accordance with at least one aspect of the present disclosure. Despite this interference 4506, the communication can occur by going around the interference 4506 along other functional communication paths 4552, 4554, 4558, 4560, 4562, 4564, 4570, for example.

The wireless mesh network 4510 described with reference to FIGS. 41-46 may be expandable to many accessories, such as the footswitch 4520, for example, where each additional accessory comprises radios that acts as nodes to strengthen the network. The wireless mesh network 4510 provides a robust wireless communication system that is tolerant to external interference and long distances. In other aspects, Bluetooth wireless modules that may be employed to implement the wireless mesh network are advantageous due to their relatively low cost and ease of installation. Further, the wireless mesh network 4510 provides security to support public/private key authentication and encryption, permission levels at network, node, and application levels, and can be used in low-power (battery powered) situations.

EXAMPLES

Various aspects of modular energy systems comprising energy delivery mitigation techniques described herein with reference to FIGS. 39-46 are set out in the following numbered examples.

Example 1. An isolated interface circuit for a modular energy system, the isolated interface circuit comprising: a comparator comprising a first input configured to couple to a switch, a second input configured to couple to a reference voltage, and an output; a duplicate comparator comprising a first input configured to couple to the switch, a second input configured to couple to the reference voltage, and an output; an expander circuit comprising at least two inputs, wherein the output of the comparator is coupled to one of the at least two inputs of the expander circuit, and wherein the output of the duplicate comparator is coupled to other of the at least two inputs of the expander circuit, the expander circuit comprising an output; an isolator circuit comprising an input and an output, wherein the input is coupled to the output of the expander circuit; and a controller coupled to the output of the isolator circuit, wherein the controller is configured to: compare the output of the comparator with the output of the duplicate comparator; and determine activation or deactivation of a surgical instrument coupled to the controller based on the comparison.

Example 2. The isolated switch interface circuit of Example 1, comprising: an analog to digital converter (ADC) coupled to the controller through the isolator circuit; and a switch identification circuit coupled to the ADC, wherein the switch identification circuit is configured to identify a type of switch coupled to the comparator and duplicate comparator.

Example 3. The isolated interface circuit of any one or more of Examples 1 through 2, wherein the isolator circuit comprises a digital isolator circuit.

Example 4. The isolated interface circuit of any one or more of Examples 1 through 3, wherein the comparator and duplicate comparator are configured to couple to multiple switches, the comparator comprising multiple comparators configured to couple to each of the multiple switches, and the duplicate comparator comprising multiple comparators configured to couple to each of the multiple switches; and wherein the controller is configured to compare the outputs of each of the multiple comparators with the corresponding outputs of each of the duplicate comparators.

Example 5. The isolated interface circuit of any one or more of Examples 1 through 4, wherein the comparator and duplicate comparator are configured to couple to a footswitch.

Example 6. The isolated interface circuit of any one or more of Examples 1 through 5, wherein the output of the isolator circuit is a digital serial communication bus.

Example 7. An isolated interface circuit for a modular energy system, the isolated interface circuit comprising: a first comparator comprising a first input configured to couple to a first switch, a second input configured to couple to a reference voltage, and an output; a second comparator comprising a first input configured to couple to a second switch, a second input configured to couple to the reference voltage, and an output; a first duplicate comparator comprising a first input configured to couple to the first switch, a second input configured to couple to the reference voltage, and an output; a second duplicate comparator comprising a first input configured to couple to the second switch, a second input configured to couple to the reference voltage, and an output; an expander circuit comprising at least four inputs, wherein each of the outputs of the first and second comparators is coupled to an input of the expander circuit, and wherein each of the outputs of the first and second duplicate comparators is coupled an input of the expander circuit, the expander circuit comprising an output; an isolator circuit comprising an input and an output, wherein the input is coupled to the output of the expander circuit; and a controller coupled to the output of the isolator circuit, wherein the controller is configure to: compare the output of the first comparator with the output of the first duplicate comparator; compare the output of the second comparator with the output of the second duplicate comparator; and determine activation or deactivation of a surgical instrument coupled to the controller based on the comparison.

Example 8. The isolated interface circuit of Example 7, comprising: an analog to digital converter (ADC) coupled to the controller through the isolator circuit; and a switch identification circuit coupled to the ADC, wherein the switch identification circuit is configured to identify a type of switch.

Example 9. The isolated interface circuit of any one or more of Examples 7 through 8, comprising any one of a comparator reference voltage, supply voltage, or switch voltage applied to the ADC, or any combination thereof.

Example 10. The isolated interface circuit of any one or more of Examples 7 through 9, wherein the isolator circuit comprises a digital isolator circuit.

Example 11. The isolated interface circuit of any one or more of Examples 7 through 10, wherein the first and second comparators and the first and second duplicate comparators are configured to couple to a footswitch.

Example 12. The isolated interface circuit of Example 11, wherein the footswitch comprises a first and second switch, wherein the first switch represents a first state of the footswitch and the second switch represents a second state of the footswitch.

Example 13. The isolated interface circuit of any one or more of Examples 11 through 12, wherein the footswitch comprises multiple footswitches, wherein each of the multiple footswitches comprises a footswitch identification circuit coupled to an analog to digital converter (ADC) coupled to the controller through the isolator circuit, wherein each of the footswitch identification circuits is configured to identify a type of foot switch.

Example 14. The isolated interface circuit of any one or more of Examples 7 through 13, wherein the output of the isolator circuit is a single digital serial communication bus.

Example 15. A method of mitigating erroneous outputs from an isolated interface circuit for a modular energy system, the method comprising: receiving, at a first input of a first comparator, a state of a first switch of a first footswitch coupled to the first input of the first comparator and a reference voltage coupled to a second input of the first comparator; receiving, at a first input of a first duplicate comparator, the state of the first switch coupled to the first input of the first duplicate comparator and the reference voltage coupled to a second input of the first duplicate comparator; comparing, by a controller coupled to outputs of the first comparator and the first duplicate comparator, the output of the first comparator with the output of the first duplicate comparator; and determining, by the controller, activation or deactivation of a surgical instrument coupled to the controller based on the comparison.

Example 16. The method of Example 15, comprising: receiving, by an analog to digital converter (ADC) coupled to the controller, a first footswitch identification signal; and identifying, by the controller, a type of the first footswitch based on the first footswitch identification signal.

Example 17. The method of Example 16, comprising: receiving, by the ADC, any one of a comparator reference voltage, supply voltage, or switch voltage; measuring, by the controller, the comparator reference voltage, supply voltage, or switch voltage applied to the ADC; determining, by the controller, that the comparator reference voltage, supply voltage, or switch voltage is within predetermined limits; and enabling, by the controller, activation of the surgical instrument in the instance that the comparator reference voltage, supply voltage, or switch voltage is within the predetermined limits; disabling, by the controller, activation of the surgical instrument in the instance that the comparator reference voltage, supply voltage, or switch voltage is not within the predetermined limits.

Example 18. The method of any one or more of Examples 15 through 17, comprising: receiving, at a first input of a second comparator, a state of a second switch of the first footswitch coupled to the first input of the second comparator and a reference voltage coupled to a second input of the second comparator; receiving, at a first input of a second duplicate comparator, the state of the second switch coupled to the first input of the second duplicate comparator and the reference voltage coupled to a second input of the second duplicate comparator; comparing, by a controller coupled to outputs of the second comparator and the second duplicate comparator, the output of the second comparator with the output of the second duplicate comparator; and determining, by the controller, activation or deactivation of a surgical instrument coupled to the controller based on the comparison.

Architecture for Modular Energy System

Having described a general implementation of modular energy systems 2000, 3000, and 6000, and various surgical instruments usable therewith, for example, surgical instruments 2204, 2206, and 2208, the disclosure now turns to various aspects of an architecture implementation for modular energy systems. In other aspects, these modular energy systems are substantially similar to the modular energy system 2000, the modular energy system 3000, and/or the modular energy system 6000 described hereinabove. For the sake of brevity, various details of other modular energy systems described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

Extending Modular Energy System Backplane to External Devices

As described hereinbelow with reference to FIGS. 47-50, in various aspects, the present disclosure provides modular energy systems 2000, 3000, 6000 comprising a modular energy system backplane extended to external devices. As disclosed above, a modular energy system may be composed of a header/User Interface (UI) module that may be in communication with and/or control the operation of multiple functional modules. Such functional modules may include, without limitation, energy modules, communication modules, technology modules, visualization modules, or other modules that may be used during a surgical procedure. Both the header/UI module and the functional modules (together, the modules) may be coupled together to form the modular energy system. In one aspect, the header/UI module and the functional modules may be stacked together with the header/UI module forming the top, or initial module. It may be recognized that the header/UI module does not have to be the top or initial module of the stack of modules. In the stacked configuration, the lowest module—which may be a functional module—may be considered the terminal module.

Each of the functional modules, which may include the terminal module, may include a module control circuit and a local data bus. The local data busses may be configured to conduct information among the various components within the modules and a module control circuit. The module control circuit may control and coordinate the operations and functions of each of the modules. In one aspect, the local data bus of each of the modules may include a communication switch, a first switch data path in data communication with the communication switch, a second switch data path in data communication with the communication switch, and a third switch data path configured to permit data communication between the communication switch and the module control circuit. Additional details regarding the numbered data paths associated with each communication switch are more fully disclosed below with respect to FIGS. 48 and 49.

Further, the modular energy system may include an internal data bus composed of a serial array of the local data busses of the plurality of functional modules, including the terminal module, in which a third switch data path of a functional module N is in data communication with a second switch data path of a functional module N+1, and a second switch data path of the terminal module is in data communication with a third switch data path of a preceding functional module. The initial module may include a physical layer transceiver (PHY) in data communication with an initial module control circuit. It may be understood that the internal data bus may further include or be in data communication with the physical layer transceiver (PHY) of the initial module. The physical layer transceiver (PHY) may also be in data communication with a second switch data path of a succeeding functional module. The modular energy system may also include a termination unit in data communication with the third data path of the terminal module. Additional disclosures regarding the use and functions of the termination unit may be found in the discussion of FIGS. 49 and 50, below. The header/UI module and the functional modules of the modular energy system may communicate with each other over a backplane comprising the internal data bus. The communication among and between the modules may use any appropriate communication protocol, for example Ethernet, USB, and FireWire.

As further disclosed above, a communication module may assist in controlling the data and command traffic among and between the functional modules and the header/UI module. In some aspects, various surgical hubs and/or surgical systems can include a gateway 3058 that is configured to shuttle select traffic (i.e., data) between two disparate networks (e.g., an internal network and/or a hospital network) that are running different protocols. In some alternative aspects, the communication module may also include a gateway 3058 (see FIG. 15) permitting communication between the modular energy system and other, external, systems and devices. The communication module may incorporate any number of communication interfaces, for example Ethernet (see 3060 FIG. 15) and USB (3062 see FIG. 15). In one example, the Ethernet interface may permit the modular energy system to communicate with components of the local hospital network using the approved hospital networking protocols. In another example, the USB interface may permit communications with laptop computers, tablet computers, smart phones, and other smaller scale devices. Communications with such external devices may proceed according to the communication protocols associated with those devices.

In some instances, it may be useful to communicate with devices and/or networks external to the modular energy system according to the same protocols as used by the internal data bus of the modular energy system. In this way, a common communication protocol may be used to link the external devices with the modules of the modular energy system. It may be recognized, for example, that external devices that rely on communication protocols that differ from those of the modular energy system would require protocol translation between the modular energy system and the external devices. Such protocol translation would necessarily result in inefficiencies in communication. Thus, it may be more efficient for the external devices and/or networks to be incorporated into the modular energy system communication network via an external extension of the modular energy system internal data bus (internal data bus extension). An example of such incorporation is illustrated in FIG. 14 in which an external system control unit 3024 of an external control system 3010 may communicate with the modular energy system over an internal data bus extension.

Alternatively, the modular energy system may use the internal data bus extension to communicate with a surgical robot, a surgical hub, or any other smart device or system. In one example, a surgeon may wish to use a small handheld electrosurgical device (such as one depicted in FIG. 4) for a procedure requiring precise hand control of the instrument. A surgical robotic system may incorporate various optical systems and lights to illuminate the surgical field. The position and orientation of the electrosurgical device may be determined by a module of the modular energy system. The module may rapidly transmit the position and orientation of the electrosurgical instrument via the internal data bus and the internal data bus extension to the surgical robotic system. The position and orientation of the electrosurgical instrument may be used by the surgical robotic system to properly place and orient illumination to optimize the visualization of the surgical field. Thus, it may be recognized that having such external devices in direct communication with the modular energy system data bus may improve, accelerate, and simplify communication and control among the components of the internal data bus and the external device and/or system.

Figure 47:
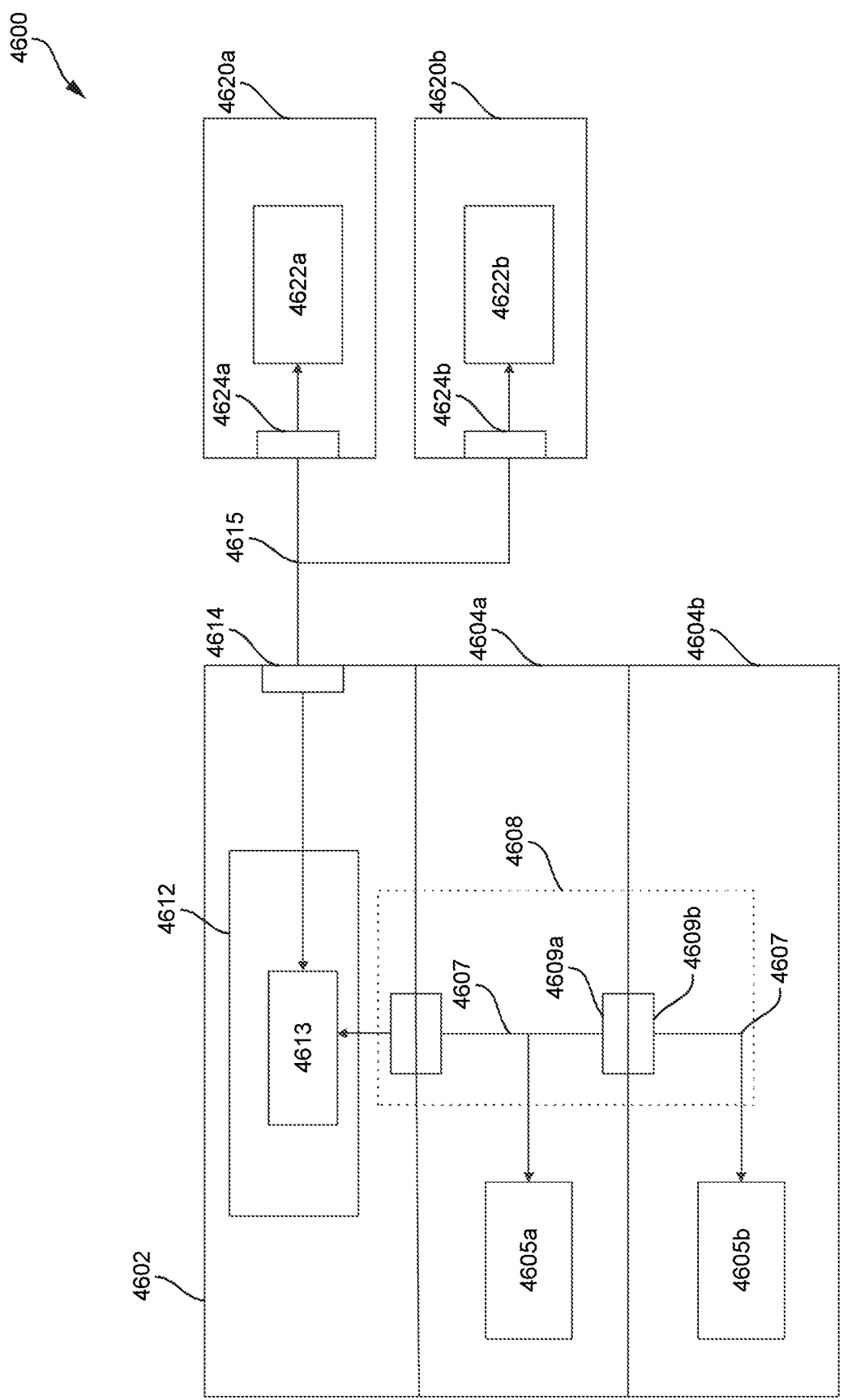
FIG. 47 is a block diagram of a modular energy system having an internal data bus extension to multiple external devices, in accordance with at least one aspect of the present disclosure.

FIG. 47 depicts a block diagram of multiple external modules 4620*a,b* connected via an internal data bus extension 4615 to a modular energy system 4600. The internal data bus extension 4615 may be connected to the external modules 4620*a,b* via communication interfaces 4624*a,b*. The internal data bus extension 4615 may be connected to the modular energy system 4600 via communication interface 4614.

The modular energy system 4600 may include a header module 4602 and multiple functional modules 4604*a,b*. The header module 4602 and the multiple functional modules 4604*a,b* may all communicate via the modular energy system internal data bus 4608. In a non-limiting example, the modular energy system 4600 may use an Ethernet protocol for communication over the internal data bus 4608. In another example, the modular system 4600 may use a USB protocol for communication over the internal data bus 4608. It may be recognized that any suitable communication protocol may be used for data and instruction communication over the internal data bus 4608. The internal data bus 4608 may include bus connectors 4609*a,b* which provide physical and communication connections between successive modules such as functional modules 4604*a,b*. The internal data bus 4608 may also include appropriate conductive traces or wires 4607 along which the communication protocol signals may be transmitted. In some aspects, the conductive traces or wires 4607 may terminate at a module controller 4605*a,b* for each of the functional modules 4604*a, b*. The module controllers 4605*a,b*, may include components to control the operations of the functional modules 4604*a,b*, as disclosed above. As depicted in FIG. 47, the various modules that comprise the module energy system 4600 may be arranged as a stack of modules interconnected by their bus connectors 4609*a,b*. In one configuration, an initial module may include the header module/UI 4602. In alternative configurations, the header module/UI 4602 may be disposed elsewhere within the stack of modules. Similarly, there may be a terminal module (for example functional module 4604*b*), which is the lowest module of the stack. In some additional examples, a termination unit (not shown) may be placed in data communication with the bus connector 4609*b* (the lowest connector) in the terminal module. Such a termination unit may be used to terminate at least one end of the internal data bus 4608. Additional disclosures regarding the use and functions of the termination unit may be found in the discussion of FIGS. 49 and 50, below.

In some aspects, the header module/UI 4602 may include a header control circuit 4612 which may control the various operations of the header module/UI 4602 as disclosed above. In some aspects, the header module/UI 4602 may control the operations of the function modules 4604*a,b* via commands and data transmitted and received over the internal data bus 4608. In some aspects, the control circuit 4612 of the header module/UI 4602 may also include a routing system 4613. In other aspects, the routing system 4613 may be incorporated into another functional module, for example in a communications module. The module of a modular energy system 4600 that incorporates the routing system 4613 may be called a host module. In some exemplary systems, the routing system 4613 may be physically fixed within the host module. In other exemplary systems, the routing system 4613 may be detachably associated with the host module. The module hosting a detachably associated routing system 4613—the header module/UI 4602, the communication module, or another module that is part of the modular energy system 4600—may further include electronic components, such as hardware and/or software, which are configured to detect a presence of a detachably associated routing system 4613. Thus, in some aspect, a detachably associated routing system 4613 may be considered an upgrade to a pre-existing modular energy system 4600. Once a host module detects the present of a routing system 4613 (either fixed or detachable), the host module may then communicate with the external modules 4620*a,b* over the internal data bus extension 4615.

In some aspects, the routing system 4613 may be in data communication with both the internal data bus 4608 and the internal data bus extension 4615. The routing system 4613 may serve to control communications between the internal data bus 4608 and the internal data bus extension 4615. In this manner, the routing system 4613 may control data communication between the internal data bus 4608 and the external module 4620*a,b* in which the external module 4620*a,b* comprises a device or system separate from the modular energy system.

It may be recognized that each of the external modules 4620*a,b* may include an external module control circuit 4622*a,b*, which may coordinate and direct the functions of the respective external module 4620*a,b*. Each of the external module control circuits 4622*a,b*, may be in communication with the modular energy system 4600 over the internal data bus extension 4615. In this manner, each of the external module control circuits 4622*a,b* may functionally become an extension of the modular energy system 4600.

As disclosed above, the ability to extend the internal data bus 4608 of a modular energy system 4600 to external devices 4620*a,b* and/or systems may permit fast and accurate communications between the energy system 4600 and the other systems that may comprise a smart surgical environment (such as a surgical robot). It is recognized, however, that unprotected communication devices may be susceptible to unwanted influences over the communication lines, for example by system hackers. Therefore, as with any networked device, a modular energy system 4600 networked to external devices 4620*a,b* and systems runs the risk of interference with its operations. This is especially serious when the modular energy system 4600 is involved with a surgical procedure. It is therefore important to protect the modular energy system 4600 from interference from communications transmitted over the extended communication backplane 4615 into the internal communication backplane 4608.

A routing system 4613 may be used to coordinate the communication traffic between the internal data bus 4608 and the internal data bus extension 4615. A routing system 4613 may include components that not only cause communication data packets to be switched between data busses (such as the internal data bus 4608 and the internal data bus extension 4615) but also include software and/or firmware to control the types of communication data packets exchanged between the busses according to their origin, destination, and specific protocols associated with the communication data packet. Thus, an intelligent routing system 4613 may comprise a routing system processor and a routing system memory unit. The routing system memory unit may store instructions that, when executed by the routing system processor, cause the processor to execute one or more communication security protocols. In some examples, the communication security protocols may include one or more of a MAC address table filter, a communication data packet filter based on an IP address, a software protocol, or a port number, stateful communication data packet inspection, and an application layer firewall.

Ethernet Switch Configuration for Backplane Reliability

As described hereinbelow with reference to FIGS. 48-50, in various aspects, the present disclosure provides modular energy systems 2000, 3000, 6000 comprising Ethernet switch configuration for backplane reliability. As disclosed above, a modular energy system may be composed of a header/User Interface (UI) module that may be in communication with and/or control the operation of multiple functional modules. Such functional modules may include, without limitation, energy modules, communication modules, technology modules, visualization modules, or other modules that may be used during a surgical procedure. Both the header/UI module and the functional modules (together, the modules) may be coupled together to form the modular energy system. In one aspect, the header/UI module and the functional modules may be stacked together with the header/UI module forming the top, or initial module. It may be recognized that the header/UI module does not have to be the top or initial module of the stack of modules. In the stacked configuration, the lowest module—which may be a functional module—may be considered the terminal module.

Each of the functional modules, which may include the terminal module, may include a module control circuit and a local data bus. The local data busses may be configured to conduct information among the various components within the modules and a module control circuit. The module control circuit may control and coordinate the operations and functions of each of the modules. In one aspect, the local data bus of each of the modules may include a communication switch, a first switch data path in data communication with the communication switch, a second switch data path in data communication with the communication switch, and a third switch data path configured to permit data communication between the communication switch and the module control circuit. Additional details regarding the numbered data paths associated with each communication switch are more fully disclosed below with respect to FIGS. 48 and 49.

Further, the modular energy system may include an internal data bus composed of a serial array of the local data busses of the plurality of functional modules, including the terminal module, in which a third switch data path of a functional module N is in data communication with a second switch data path of a functional module N+1, and a second switch data path of the terminal module is in data communication with a third switch data path of a preceding functional module. The initial module may include a physical layer transceiver (PHY) in data communication with an initial module control circuit. It may be understood that the internal data bus may further include or be in data communication with the physical layer transceiver (PHY) of the initial module. The physical layer transceiver (PHY) may also be in data communication with a second switch data path of a succeeding functional module. The modular energy system may also include a termination unit in data communication with the third data path of the terminal module. Additional disclosures regarding the use and functions of the termination unit may be found in the discussion of FIGS. 49 and 50, below. The header/UI module and the functional modules of the modular energy system may communicate with each other over a backplane comprising the internal data bus. The communication among and between the modules may use any appropriate communication protocol, for example Ethernet, USB, and FireWire.

In one aspect, the internal data bus of the modular energy system may rely upon an Ethernet protocol for communications between the modules, which may include, without limitation, the functional modules and any header I/U module. As disclosed above, the internal data bus of the modular energy system may be composed of serially connected local data busses of the individual modules. It may be readily recognized that an error or fault in any one of the individual local data busses may disrupt or even prevent communications along the entirety of the internal data bus. For example, a fault in one of the components of the local data bus of a module N (for example a failure of the module N communication switch) may result in a blockage of communications between a module N−1 (a module preceding module N in the internal data bus serial array) and a module N+1 (a module succeeding module N in the internal data bus serial array). It is therefore important to provide a fail-over mechanism to prevent a fault in one of the local data busses from affecting communications among the modules around it.

Figure 48:
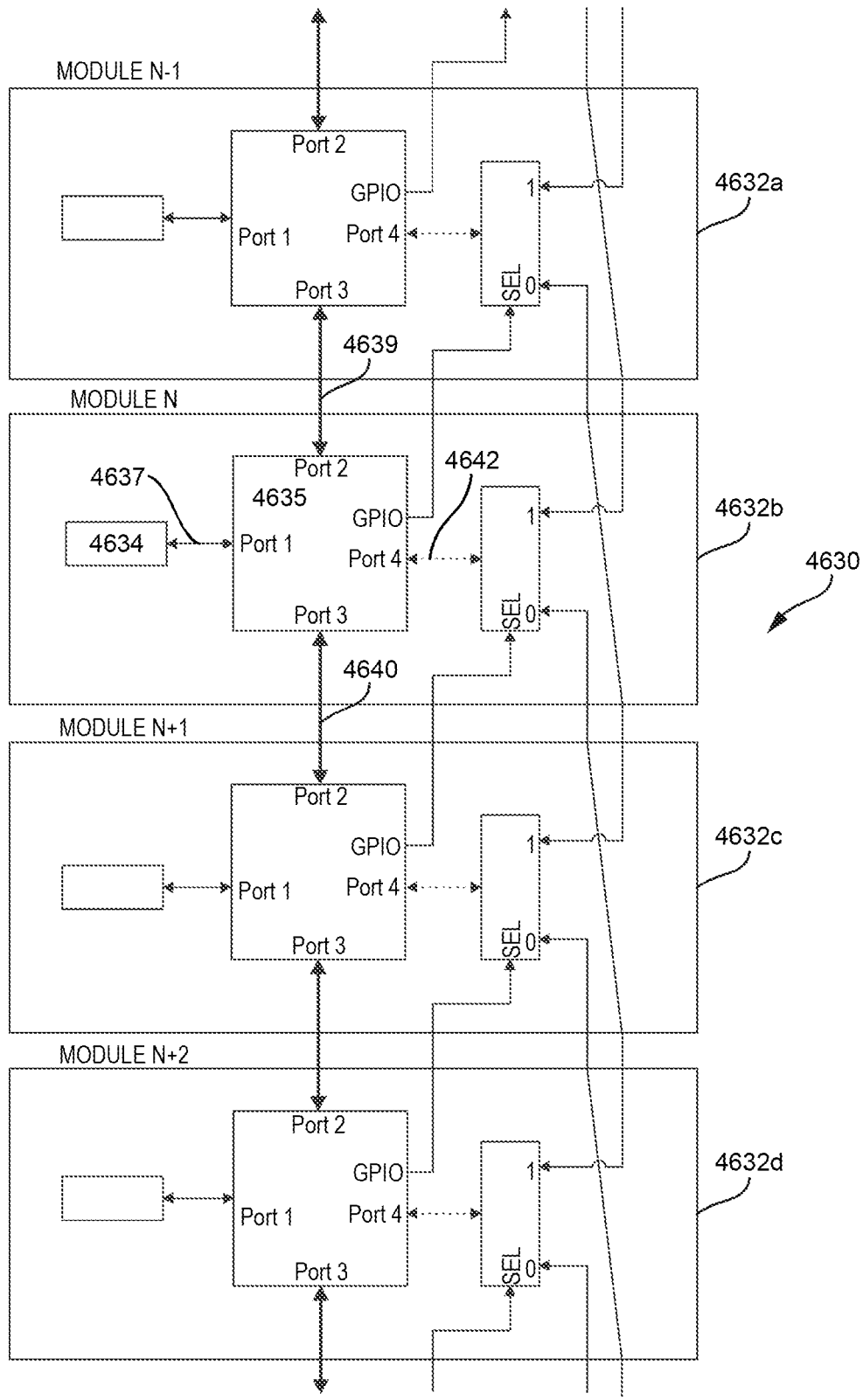
FIG. 48 is a block diagram of an internal data bus of a modular energy system depicting data communications throughout the internal data bus under normal conditions, in accordance with at least one aspect of the present disclosure.
Figure 49:
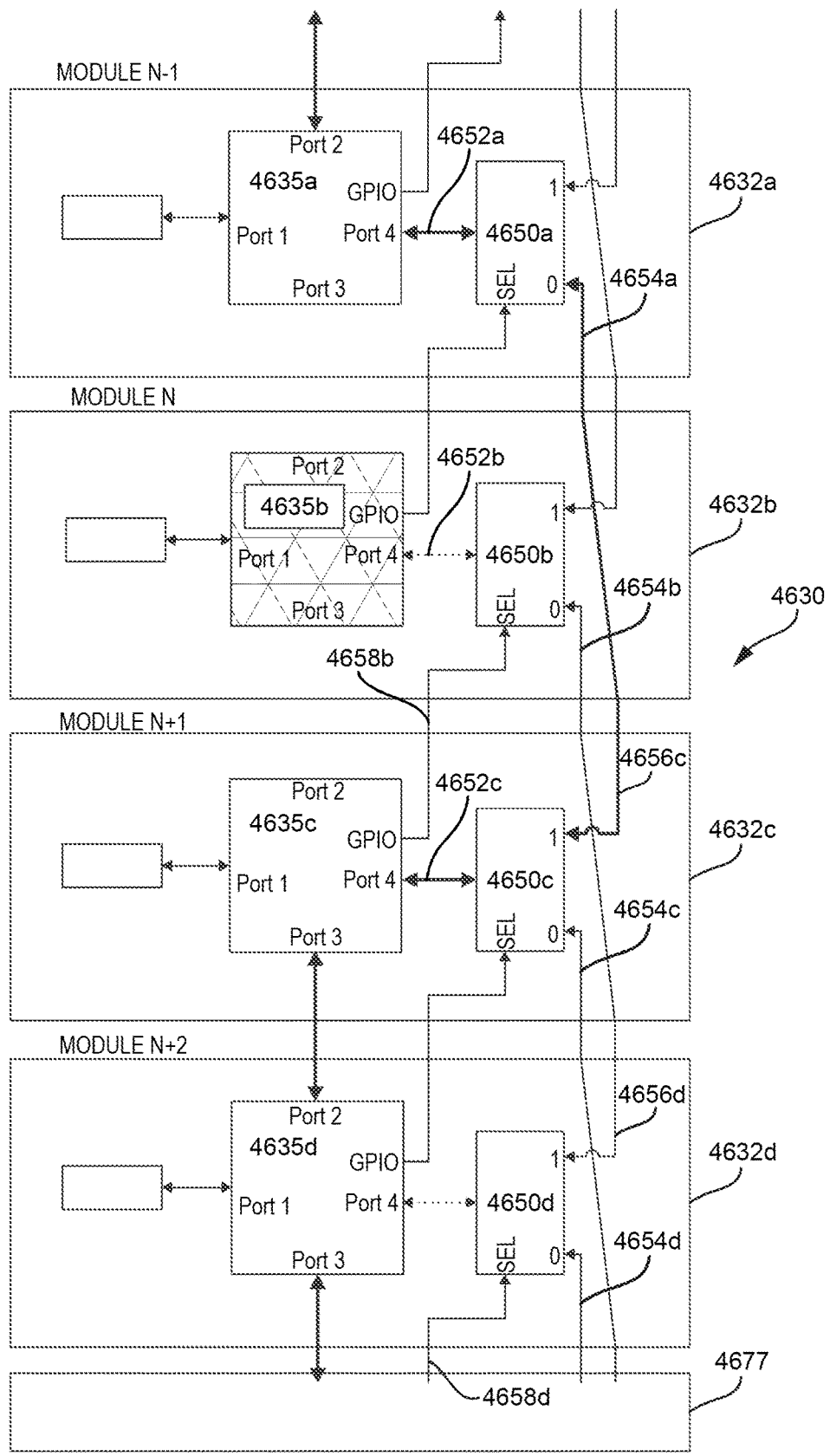
FIG. 49 is a block diagram of an internal data bus of a modular energy system depicting data communications throughout the internal data bus during a switch failure, in accordance with at least one aspect of the present disclosure.

FIGS. 48 and 49 depict communication circuitry, which may be incorporated into the local data busses of the modules of the modular energy source. Specifically, FIG. 48 depicts the communication circuitry when all of the local data busses are functioning normally. FIG. 49 illustrates the communication circuitry when the local data bus for a module N does not properly function.

FIG. 48 illustrates an internal data bus 4630 of a modular energy system composed of a serial array of local data busses 4632*a-d*. Each data bus 4632*a-d* is incorporated in a separate energy system module (which may be a functional module or a header/UI module). For the sake of simplicity, and without loss of generality, energy system Module N may be assigned to the energy system module that incorporates local data bus 4632*b*. Following this convention, energy system Module N−1 may be assigned to the energy system module that incorporates local data bus 4632*a*, energy system Module N+1 may be assigned to the energy system module that incorporates local data bus 4632*c*, and energy system Module N+2 may be assigned to the energy system module that incorporates local data bus 4632*d*. It may be understood that the designations of Module N−1, N, N+1, and N+2 are arbitrary as long as the designations refer to successes energy modules in the internal data bus. Again, for simplicity, a detailed discussion of the components of local data bus 4632*b* is now presented. It may be understood that the components, connectivity, and bus structures of each of the local data busses (4632*a-d*) is similarly described.

Local data bus 4632*b* may include a communication switch 4635 that, in some non-limiting examples, may be composed of an Ethernet switch. The communication switch 4635 may be in data communication with a plurality of data switch paths. A first switch data path 4637 may be configured to permit data communication between the communication switch 4635 and the module control circuit 4634 of the module. As previously disclosed, the module control circuit 4634 may be configured to control the functional and communication operations of the module (here, Module N). A second switch data path 4639 may be in data communication with the communication switch 4635, and a third switch data path 4640 be in data communication with the communication switch 4635. The communication switch 4635 may also be in communication with a fourth switch data path 4642. It may be understood that a communication switch 4635 may function to direct communication or data signals from one of the switch paths 4637, 4639, 4640, 4642 to another of the switch paths 4637, 4639, 4640, 4642. The communication switch 4635 may have a switch path interface in data communication with each switch path 4637, 4639, 4640, 4642. Each switch path interface of the communication switch 4635 may be bi-directional, thereby permitting signals to either be received or transmitted by the communication switch 4635 over the active switch path.

According to some communication geometries, the second switch data path 4639 of Module N may be in data communication with the equivalent third switch data path of Module N−1. Similarly, the third switch data path 4640 of Module N may be in data communication with the equivalent second switch data path of Module N+1. One may therefore consider the communication paths among three successive modules. Under normal operating circumstances, a given communication data packet may be transmitted along the internal data bus 4630, being relayed from one module to a succeeding module along their respective internal data busses 4632a-d by the respective communication switches 4635. The relay may include transmitting a communication data packet down a third switch data path 4640 of Module N to the second switch data path of the succeeding module N+1, or up a second switch data path 4639 of Module N to the third switch data path of the preceding Module N−1. Each communication switch 4635 may read a destination address of the communication data packet and either relay the pack along the internal bus 4630 to a succeeding or preceding local data bus (one of 4632a-d, as examples), or route the communication data packet to the module control circuit 4634 of the same module if the communication data packet address is for the same module. However, it may be recognized that if one of the communication switches 4635 fails, no communication data packets can be transmitted along the internal data bus 4630 beyond the module having the failed communication switch 4635.

FIG. 49 illustrates how additional components of the individual local data busses 4632a-d may be used to route data and communication signals around a local data bus (for example local data bus 4632b of Module N) to avoid issues with a failed communication switch 4635b. In the present example, the data and/or communication signals may be routed between Module N+1 (local data bus 4632c) and Module N−1 (local data bus 4632a) when the communication switch 4635b of Module N is non-functional.

The reference numbers illustrated in FIG. 48 also apply to FIG. 49. In addition to the components disclosed in FIG. 48, FIG. 49 further points out and describes additional components also depicted in FIG. 48. Thus, each of the local data busses 4632a-d further includes a multiplexer, for example multiplexers 4650a-c (as specified for the relevant local data busses 4632a-c). Each multiplexer, for example multiplexers 4650a-c, is in data communication with a first multiplex data path (for example 4652 a-c, as specified for the relevant local data busses 4632a-c). The first multiplex data path 4652a-c may be in data communication with the relevant fourth switch data path. Thus, for example, 4652b of local data bus 4632b may be in data communication with fourth switch data path 4642 of local data bus 4632b in FIG. 48. Additionally, each multiplexer 4650a-c may have a second multiplex data path (such as 4654a of local data bus 4632a) and a third multiplex data path (such as 4656c of local data bus 4632c). In one aspect, the multiplexers 4650a-c may be configured to direct data communications between the first multiplex data path 4652a-c and the second multiplex data path (such as 4654a of local data bus 4632a). In another aspect, the multiplexers 4650a-c may be configured to direct data communications between the first multiplex data path 4652a-c and the third multiplex data path (such as 4656c of local data bus 4632c). The direction of data communications of a multiplexer 4650a-c may be determined based on a logic level of a data path selection line (such as 4658b of local data bus 4632b) of the multiplexer 4650a-c. It may be observed in FIGS. 48 and 49 that the second multiplex data path (such as 4654a of local data bus 4632a, corresponding to module N−1) is in data communication with the third multiplex data path (such as 4656c of local data bus 4632c corresponding to module N+1). Thus, communication data packets can be transferred not between succeeding local data busses (that is, for example, between 4632a and 4632b) but between alternating local data busses (that is, for example, between 4632a and 4632c).

The operation of the fail-over mechanism may be generalized with respect to the components disclosed above for FIGS. 48 and 49. It may be recognized that the fail-over mechanism is activated among the three successive local data busses of three successive modules of the modular energy system, here, modules N−1, N, and N+1. As previously described, typical communications between the modules of a modular energy system as disclosed above, run through an internal data bus comprising a serial array of local data buses for the modules. Thus, without loss of generally, a communication data packet originating in Module N−2 may be delivered to Module N+1 by sequentially traversing the local data buses of Module N−1 and Module N. The communication data packet may be generated by a control circuit of Module N−2 and transmitted to the communication switch of Module N−2 over the first switch data path of the communication switch of Module N−2. The communication switch of Module N−2 may then transmit the communication data packet over the third switch data path of the Module N−2 communication switch to the second switch data path of the Module N−1 communication switch. The Module N−1 communication switch may receive the communication data packet over the second switch data path of the Module N−1 communication switch and relay the communication data packet over the third switch data path of the Module N−1 communication switch for receipt by the second switch data path of the Module N communication switch. The communication data packet may be similarly transmitted to the Module N+1 communication switch for delivery to the control circuit of Module N+1 (over the first switch data path).

In one exemplary aspect, under normal operations, the data transmission direction of multiplexer of each module (for example the multiplexer of Module N) may be controlled by the communication switch of the succeeding module (communication switch of Module N+1). In one aspect, the default operation of the communication switch of Module N+1 may be to configure the multiplexer of Module N to permit data transfer between the first multiplex data path and the third multiplex data path of the multiplexer of Module N. Therefore, the default multiplexer-to-multiplexer communication path would be from Module N to Module N−2. This multiplexer-to-multiplexer communication path generalizes to a unidirectional pathway from a first module to a second module preceding the first module by two.

In the event that the communication switch of Module N fails, the communication switch of Module N may reconfigure the operations of the multiplexer of Module N−1. In this reconfiguration, data communications between the first multiplex data path and the second multiplex data path of the Module N−1 multiplexer would be permitted. Thus, on failure of the Module N communication switch, a bidirectional multiplexer-to-multiplexer communication path may be enabled between Module N+1 and Module N−1. Specifically, data from the module N+1 communication switch may traverse the fourth switch data path to the third multiplex data path of the multiplexer of Module N+1. The communication data may then traverse the connection between the Module N+1 multiplexer to the multiplexer of Module N−1. The resulting transmission would enter the multiplexer of Module N−1 at the second multiplex data path and proceed through the first multiplex data path to the communication switch via the fourth switch data path of Module N−1. This multiplexer-to-multiplexer communication path generalizes to a bidirectional pathway between any two modules that can be designated as alternating modules N−1 and N+1.

Additionally, in the event that the communication switch of Module N fails, both Module N+1 and Module N−1 can detect that Module N has failed. For example, Module N+1 or Module N−1 may not receive acknowledgement packets after transmitting communication data packets to Module N. Detection of the Module N communication switch failure may result in Module N+1 and Module N−1 to resort to a link aggregation process. In this process, the communication switch of Module N+1 may reroute communication from the Module N+1 second switch data path to the Module N+1 fourth switch data path, permitting communication through the Module N+1 multiplexer first multiplex data path. Similarly, the communication switch of Module N−1 may reroute communication from the Module N−1 third switch data path to the Module N−1 fourth switch data path, permitting communication through the Module N−1 multiplexer first multiplex data path. Because the multiplexers are alternately connected (and not sequentially connected), the multiplexers, communications through the internal data bus of the modular energy system may continue even if one of the serially connected communication switches is disabled.

Because the fail-over communication method requires communication transmissions between alternating modules (for example, between Module N−1 and Module N+1), a question may arise regarding transmissions if the communication fault occurs at the penultimate module of the modular energy source. In reference to FIG. 49, and without loss of generality, one may consider that labeled Module N+2 is the terminal module of the modular energy system. In the event of a fault in the communication switch 4635c of Module N+1, the communications must be routed between Module N+2 and Module N. However, the multiplexer 4650d of Module N+2 must be configured to permit communications between communication switch 4635d of Module N+2 and communication switch 4635b of Module N. Thus, data path selection line 4658d for the multiplexer 4650d must be set to an appropriate value to ensure the communication output from the fourth switch data path of communication switch 4635d is routed through the first multiplexer line of multiplexer 4650d through the third multiplex data path 4656d to the second multiplex data path 4654b of multiplexer 4650b of Module N. Additionally, second multiplex data paths of multiplexers 4650c (Module N+1) and 4650d (Module N+2) may also require electrical termination. Similarly, the third switch data path of data switch 4635d of Module N+2 should also be electrically terminated. Thus, termination unit 4677 may be connected to the local bus of the terminal module (in this example, local bus 4632d of Module N+2). Additionally, termination unit 4677 may provide an appropriate electrical termination for the internal data bus or the local data bus of a particular module to which it is affixed, for example 4632d. Additionally, the termination unit 4677 may configure the data path selection line 4658d of the of the terminal module to which it is affixed to permit communications between the first multiplex data path of multiplexer 4650d and the third multiple data path 4656d.

Multiple Addressing Mitigation and Self-Check

As described hereinbelow still with reference to FIGS. 48-50, in various aspects, the present disclosure provides modular energy systems 2000, 3000, 6000 comprising multiple addressing mitigation and self-check circuits and techniques. As disclosed above, a modular energy system may be composed of a header/User Interface (UI) module that may be in communication with and/or control the operation of multiple functional modules. Such functional modules may include, without limitation, energy modules, communication modules, technology modules, visualization modules, or other modules that may be used during a surgical procedure. Both the header/UI module and the functional modules (together, the modules) may be coupled together to form the modular energy system. In one aspect, the header/UI module and the functional modules may be stacked together with the header/UI module forming the top, or initial module. It may be recognized that the header/UI module does not have to be the top or initial module of the stack of modules. In the stacked configuration, the lowest module—which may be a functional module—may be considered the terminal module.

Each of the functional modules, which may include the terminal module, may include a module control circuit and a local data bus. The local data busses may be configured to conduct information among the various components within the modules and a module control circuit. The module control circuit may control and coordinate the operations and functions of each of the modules. In one aspect, the local data bus of each of the modules may include a communication switch, a first switch data path in data communication with the communication switch, a second switch data path in data communication with the communication switch, and a third switch data path configured to permit data communication between the communication switch and the module control circuit. Additional details regarding the numbered data paths associated with each communication switch are more fully disclosed above with respect to FIGS. 48 and 49.

Further, the modular energy system may include an internal data bus composed of a serial array of the local data busses of the plurality of functional modules, including the terminal module, in which a third switch data path of a functional module N is in data communication with a second switch data path of a functional module N+1, and a second switch data path of the terminal module is in data communication with a third switch data path of a preceding functional module. The initial module may include a physical layer transceiver (PHY) in data communication with an initial module control circuit. It may be understood that the internal data bus may further include or be in data communication with the physical layer transceiver (PHY) of the initial module. The physical layer transceiver (PHY) may also be in data communication with a second switch data path of a succeeding functional module. The modular energy system may also include a termination unit in data communication with the third data path of the terminal module. Additional disclosures regarding the use and functions of the termination unit may be found in the discussion of FIGS. 49, and 50, below. The header/UI module and the functional modules of the modular energy system may communicate with each other over a backplane comprising the internal data bus. The communication among and between the modules may use any appropriate communication protocol, for example Ethernet, USB, and FireWire.

As previously disclosed, communication data packets may be transferred among the various modules comprising the modular energy system along the internal data bus. In many communication protocols involving multiple nodes, the communication data packets may include a source address (identifying the originator of the communication data packet) and a destination address (identifying the intended recipient of the communication data packet). Therefore, each node along the communication network must have an address specific to that node in order to identify it in the communication transfer.

In a realization of one type of a data network, the individual nodes may be represented by individual computer boards physically plugged into an interface in a common backplane. In one aspect, the backplane may be part of a chassis to secure and hold the computer boards. In this aspect, addresses may be associated with each interface, and the boards themselves do not require circuitry to define their respective addresses. In another realization, the individual nodes may be individual standalone modules, which may be deployed as a serial array of sequentially connected modules. In some aspects, each module may include circuitry to define the address of the node. Such circuitry may include DIP switches, jumpers, or other adjustable circuits to define the addresses. Alternatively, such address defining circuitry may include a static or programmable circuit component, such as a ROM, PROM, EPROM, or similar, which may include the address of the module. It may be recognized that communication errors may arise if multiple modules have their adjustable addressing circuits set to identical values. It may also be recognized that the use of static or programmable circuit components may increase manufacturing costs and complexity to assure that each manufactured module has a different address built into the static or programmable circuit component. An alternative realization of the data network may be a serial array of standalone modules in which each module can generate a local communication address based on the communication address of the preceding module. If properly configured, the address generation circuitry may permit each module along a serial communication line to generate a separate communication address from among the $2^n$ possible addresses of an n-line address bus.

It may thus be understood that each module comprises circuitry necessary to generate a local communication address from the communication address of a previous module along the serial communication chain. As a result of this topology, a module that is unable to properly generate a local communication address may affect communication not only with that module, but with all succeeding modules along the communication chain. Faults in generating a local address may be due, for example, to faulty or broken connections between a local data bus of a module and the local data bus of the preceding module to which it is connected. Thus, the communication integrity along the serial bus should be monitored for improper local addressing. FIG. 50 depicts a mechanism both for generating local communication address values from an n-line address bus, and also a mechanism for detecting a fault in the generation of the local address.

Figure 50:
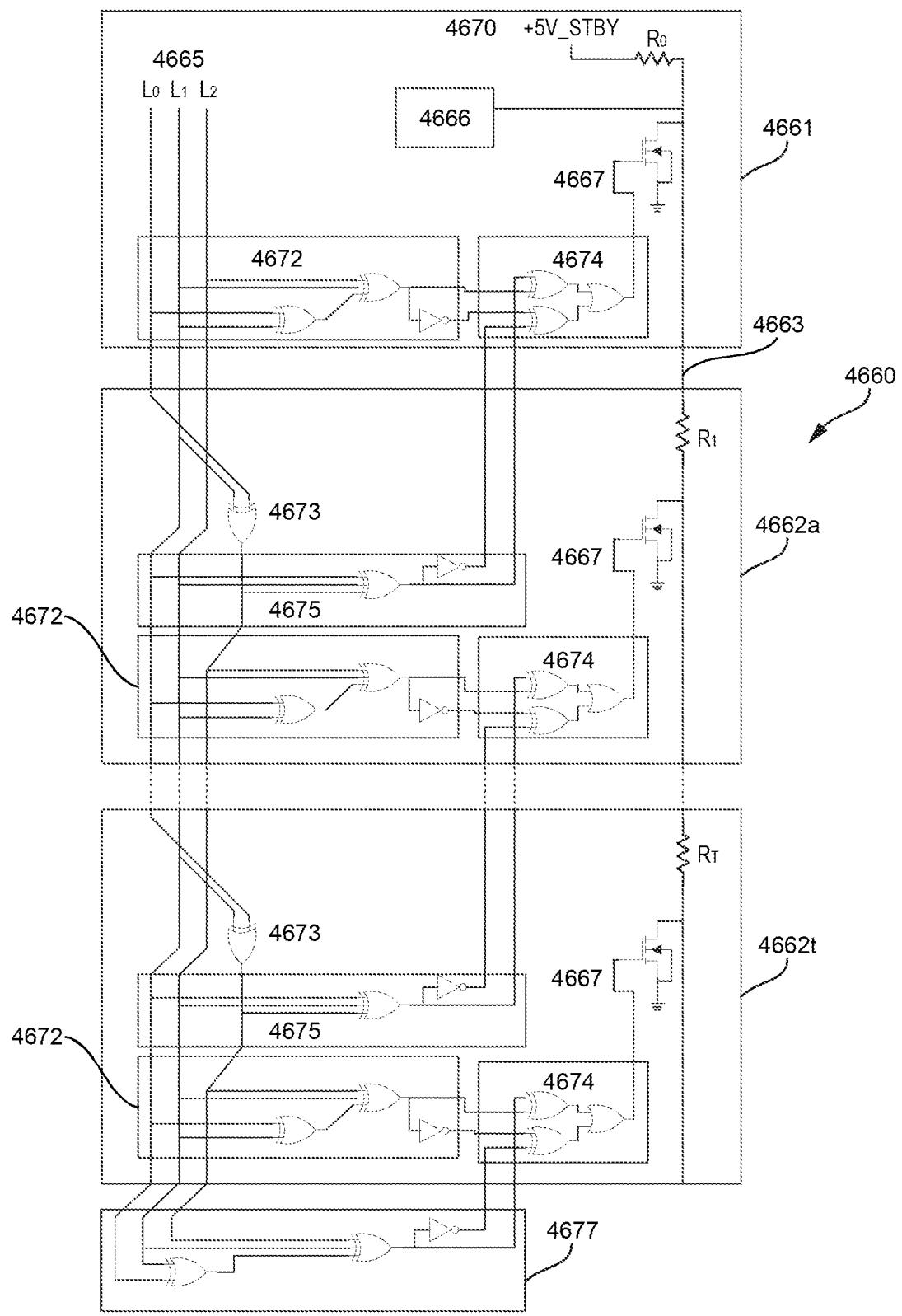
FIG. 50 is a block diagram of an internal data bus of a modular energy system depicting the generation of a communication switch address for each local data bus and a parity check system for the addresses, in accordance with at least one aspect of the present disclosure.

FIG. 50 illustrates an example of an internal data bus 4660 comprising multiple modules. Without being limited in the topology of the communication, the top-most, or initial module of the internal data bus 4660 may comprise a header/UI module. Any suitable number of functional modules may be incorporated along the internal data bus 4660. The final, or terminal, module comprises the last functional module in the series of functional modules along the internal data bus 4660. Each of the modules, including the header/UI module and all of the functional modules, includes a local data bus. As disclosed above, the internal data bus 4660 is composed of a serial connection of all of the local data busses of the modules. Depicted in FIG. 50, are the local data busses of the various modules including the local data bus 4661 of the header/UI module, and the local data busses 4662a-4662t of the functional modules. The local data bus 4662t of the terminal functional module is specifically labeled as such.

In addition to the various components of the local data busses (4661,4662a-t) as disclosed above, FIG. 50 depicts additional components. Thus, all of the local data busses also include a plurality of address lines 4665, a predictive address parity circuit 4672, a parity comparison circuit 4674, a parity fault generation circuit 4667, and an address fault line 4663. Additionally, all of the modules except the initial module may include a local address generator circuit 4673 and a local address parity circuit 4675. The initial module also includes an analog/digital converter 4666 to obtain a digital value of the voltage on the address fault line 4663.

The number of modules that can be addressed in a modular energy system is generally $2^n$ in which n is the number of address lines. In the example depicted in FIG. 50, there are three address lines, conveniently labeled $L_0$, $L_1$, and $L_2$. Of course, the number of address lines is arbitrary. There may be any number of algorithms capable of generating a local address value for a module n from a local address value of a preceding module n−1. FIG. 50 illustrates one non-limiting local address generator circuit 4673 to do so. Local address generator circuit 4673 relies upon interleaving succeeding addressing lines and adding a new address line formed from a logical combination of address lines. As illustrated in local address generator circuit 4673, the values of the address lines for the succeeding module are calculate by $L_0' \leftarrow L_1$ $L_1' \leftarrow L_2$ $L_2' \leftarrow L_0 \oplus L_1$ in which the unprimed lines are the values of the addresses of the preceding Module N, the primed lines are the addresses of the succeeding Module N+1, and $\oplus$ is the logical XOR operation. Although this algorithm is depicted in FIG. 50, alternative algorithms may be used to generate address line values for a Module N+1 from the address line values for preceding Module N. It may also be recognized that the address lines may include any number of address lines for the purpose of generating unique addresses for all of the modules in the modular energy system. As disclosed above, the number of address lines determines the maximum number of modules that may be sequentially connected in the modular energy system. Thus, for example, two address lines would permit up to four distinct device addresses, three address lines would permit up to eight distinct device addresses, four address lines would permit up to sixteen distinct device addresses, and similar.

As disclosed above, it is useful to assure that each module successfully generates its local communication address from the address of the preceding module. One method of making such a determination may be to compare the address of the succeeding Module N+1 with a predicted value for that address. This comparison may be made in the preceding Module N. Such a comparison may be made by comparing the value of each of the address line. However, it is recognized that a line-by-line address comparison becomes difficult as the number of address lines increases. Instead, it may be more useful to generate a parity value to represent the addresses. Again, there are multiple algorithms to generate a parity value for the address lines. As one non-limiting example, a local address parity circuit 4675 may be simply created as applying an XOR operation ($\oplus$) to all of the address lines. Further, to ensure accuracy, the local address parity circuit 4675 may also generate an inverse of the parity value. Thus, the signals generated by the local address parity circuit 4675 may be $$P = L_0 \oplus L_1 \oplus L_2$$

$$P' = \overline{P}$$

in which P is the parity value and P' is the inverse of the parity value.

Each Module N may calculate a predictive value of the parity values of the succeeding Module N+1 in a predictive address parity circuit 4672 according to $$\hat{P} = (L_0 \oplus L_1) \oplus L_1 \oplus L_2$$

$$\hat{P}' = \overline{\hat{P}}$$

in which $L_0$, $L_1$, and $L_2$ are the address line values of Module N. In Module N, the predicted parity values of the succeeding Module N+1 (here $\hat{P}$ and $\hat{P}'$) may be compared, using the parity comparison circuit 4674 in Module N, to the parity values calculated by the local address parity circuit 4672 in succeeding Module N+1 (P and P', respectively). In this manner, only 4 signals need to be compared to determine if the address of the succeeding Module N+1 is correct.

As disclosed above, each Module N compares the parity value of the address supplied by Module N+1 with a predictive parity value of the address of Module N+1. However, at the terminal module, Module T, there is no succeeding module to supply a parity value. In one non-limiting example of a technique to rectify this issue, a termination unit 4677 may be affixed to a terminal end of the internal data bus 4660. The termination unit 4677 may include a local address parity circuit similar in function to predictive address parity circuit 4672. The resulting address parity values from the termination unit 4677 may be compared to the predictive address parity circuit 4672 of terminal Module T. In this way, each of the modules may determine an address fault in a succeeding module.

It may be understood that address faults in the modules that make up the modular energy system should be made known to the modular energy system as a whole and to any user of the modular energy system. One or more hardware and/or software techniques may be used to report an address fault in a module. One example of a technique to report an address fault may be through an address parity fault generation circuit. Each module may include a parity fault generation circuit 4667 in its local data bus. In a non-limiting and simple realization, the parity fault generation circuit 4667 may simply comprise a switch connecting the address fault line 4663 to ground. The address fault line may include a single analog conductor connected to a voltage source 4670, such as a standby DC voltage (which may be +5V in some examples) in the initial module, such as the header/UI module. In each module local bus, a series resistor may be affixed in the address fault line 4663. Such series resistors are schematically depicted as resistors $R_0$, $R_1$, ... $R_T$ in FIG. 50. An initial current limiting resistor $R_0$ may be placed in series downstream of the voltage source 4670. A voltage of the address fault line 4663 may be read by a sensor circuit 4666 disposed downstream of the current limiting resistor $R_0$. In one example, the sensor circuit 4666 may be an analog/digital converter (ADC). In some aspects, the address fault line, the voltage source, and the sensor circuit may all be incorporated into the local data bus of the initial module, such as the header/UI module.

As disclosed above, the parity fault generation circuit 4667 of Module N may be triggered due to a mismatch in the address parity value from Module N+1 and the predicted address parity value of Module N+1. When the parity fault generation circuit 4667 of Module N is triggered, the address fault line 4663 will be shorted to ground by the fault generation circuit 4667 of Module N. When the address fault line 4663 is shorted to ground, the analog voltage of the address fault line 4663 changes. The voltage read by the sensor circuit 4666 may have a value proportional to the ratio of the sum of the values of the resistances of the resistors $R_1$ ... $R_n$ to the sum of all of the resistors, $R_0$ ... $R_n$, in which $R_n$ is the value of the series resistor in the address fault line at Module N (where the fault is generated). The voltage value read by the sensor circuit 4666 may be converted to a digital value, and the digital value may be transmitted to a central control circuit. The central control, in turn, may use the voltage value and the known number of modules to determine which of the n modules has suffered an address fault. A notification circuit may then inform a user of the address fault in the modular energy system based on the voltage value obtained by the sensor circuit 4666. The user may then take appropriate action to repair or replace the Module N+1 in the modular energy system.

Standby Mode Fault User Feedback

As described hereinbelow with reference to FIG. 51, in various aspects, the present disclosure provides modular energy systems 2000, 3000, 6000 comprising standby mode fault user feedback circuits and techniques. As disclosed above, various communication functions may be implemented in hardware and software to permit a user of the modular energy system, or a larger smart surgical system, to recognize that one or more error conditions exist. In this way, the causes of such faults may be remedied by a user prior to initiating the use of one or more of the components of the smart surgical system. It may be recognized that identification of such faults should be made as soon as possible once any of the components or subsystems of the smart surgical system is powered on in order to expedite remediation. Many user notifications may be presented on boot-up of the processors of the various subsystems and components of the smart surgical system. Such notifications may include notifications of communication faults, among others. Typically, unless a user sees a fault notification, the user may assume that the components of the smart surgical system are operating at nominal conditions. However, if there is a fault in processor unit boot-up, the processor may not be able to notify the user of any additional system errors. It may be only during a surgical procedure or the pre-surgical initiation procedures, that a boot-up fault is detected. Such late fault detection may serious impact the surgical procedure, its start time, and procedure length. Consequently, it may be recognized that a method to determine an early processor boot-up fault for any processor component of the smart surgical system may be critical to avoid surgical procedure delay or cancellation.

Figure 51:
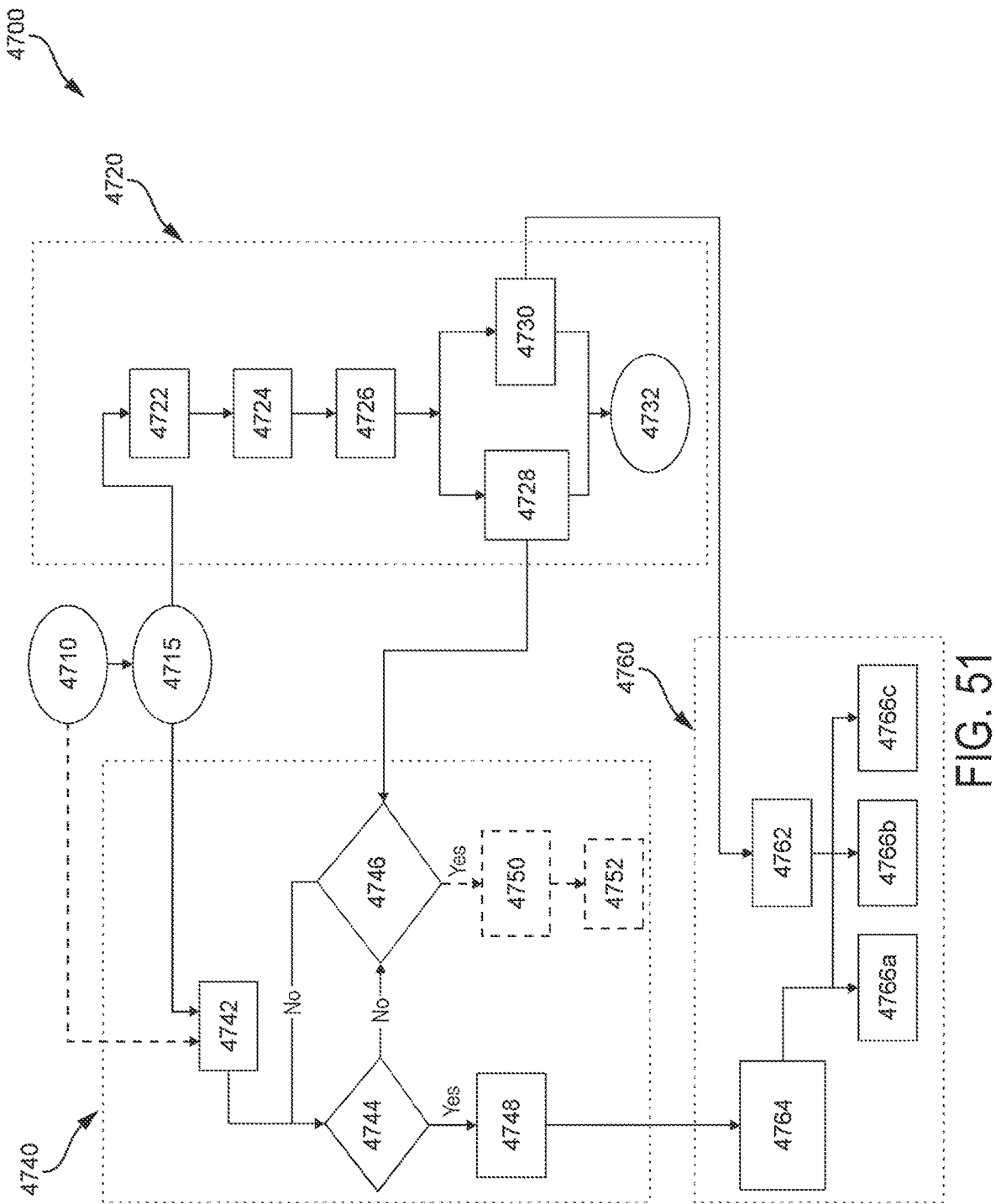
FIG. 51 depicts a flow chart of a process and components that may be used to present a user with an indication of a processor boot-up fault, in accordance with at least one aspect of the present disclosure.

FIG. 51 depicts a flow chart 4700 of a process and components that may be used to present a user with an indication of a processor boot-up fault. It may be recognized that such a process and components may be used for any processor component of the modular energy system (such as the header/UI module alone, for each individual functional module, or for the modular energy system as a single device) or any other system or subsystem of the smart surgical system. The processors under test may include, without limitation, any of the processors associated with each of the individual modules, as well as additional processors, such as a standby processor that may control the overall operation of the modular energy system.

Systems that may participate in a boot-up fault detection system may include, without limitation, a processor under test 4720, a hardware timing circuit 4740, and a notification device. The notification device may be an audible device, a visual device, or any other device capable of alerting a user of a status of the modular energy device. In one non-limiting aspect, the notification device may be a multicolor visualization device 4760. As one non-limiting example, the multicolor visualization device 4730 may be a three-color LED. In one non-limiting example, the processor under test 4720 may include a control circuit of one of the functional modules (or the header/UI module). It may be understood that the control circuit, in addition to having a processor, may also include one or more memory units configured to store instructions for execution by the modular energy system control circuit. In one non-limiting example, the processor under test 4720 may relate to a standby processor disposed within a header/UI module of the modular energy system. In another example, the processor under test 4720 may related to a processor disposed within a control circuit of one of the functional modules of the modular energy system.

The hardware timing circuit 4740 may be composed of any one or more electronic hardware timers and/or counters. In one non-limiting example, the hardware timing system 4740 may be a digital circuit which may include a timing signal generator, a counter, and a digital comparator. The timing signal generator may be composed of a free-running oscillator which generates a timing signal that may server as input to the counter. Alternatively, the timing signal may be obtained from an exogenous source, such as an internet timing signal, a GPS signal source, or a shortwave radio source. The timing signal may be initiated when power is applied to the computerized system. The counter may be a stand-alone counter with a value that increments upon receiving transitions in the timing signal. The digital comparator may compare a digital output of the stand-alone counter with the contents of a memory device designed to store a digital representation of a predetermined value. Alternatively, the hardware timing system 4740 may be composed of an analog circuit including, for example, an RC (resistor-capacitor) circuit, a circuit to generate a voltage threshold associated with the predetermined value, and an analog comparator. A timing voltage may be applied to the RC circuit when power is applied to the computerized device. The analog comparator may compare a voltage output of the RC circuit with the voltage threshold. In some other examples, the hardware timing circuit 4740 may include mixed analog/digital components such as a 555 timer integrated circuit with a resistor and a capacitor, as is well understood by those having ordinary skill in the art.

The multicolor visualization device 4760 may provide a visual indicator to notify a user of the boot-up status of the processor.

The system for notifying a user of a processor boot-up fault may begin with plugging the electrical power mains 4710 of the computerized system into the appropriate power receptacle. In some aspects, the second step of the process may include activating 4715 the power switch of the computerized system. Alternatively, the boot-up fault system may not require activation 4715 of the power switch, but may be initiated simply by plugging the electrical power mains 4710 into the power receptacle. Considering first the processor under test 4720, the processor may initiate 4722 its boot-up process. As disclosed above, the processor under test may be a processor associated with any of the systems or subsystems of the smart surgical system, including, for example, a processor of a modular energy system control circuit disposed within a header/UI module. The boot-up process may comprise initiating the execution of a series of instructions upon receipt of local power by the computerized device to initialize one or more functions of the processor under test 4720. Depending on the complexity of the operating system being loaded into the processor and the number and types of self-test programs being run during boot-up, there may be a boot-up process delay time 4724 between the initiation 4722 of the boot up process and the completion 4726 of the boot-up process. In one aspect, a processor boot-up delay time 4724 may be about 10 μsec. In another aspect, the processor boot-up delay time 4724 may be about 200 μsec. Depending on the nature of the processor, the processor clock, and the extent of the software required to be executed, the boot-up delay time 4724 may be, for example, any value between about 10 μsec and about 200 μsec. At the completion 4726 of processor boot-up, the processor may transmit an over-ride signal 4728 to cause the hardware timing circuit 4740 to cease functioning. Further, at the completion 4722 of processor boot-up, the processor may transmit 4730 configuration data to the multicolor visualization device 4760. Once the processor has completed these tasks, the processor may then enter a standby state 4732. The processor in the standby state 4732 may be ready to receive instructions from a user to begin a required surgical procedure.

With regards to the hardware timing circuit 4740, once the electrical power mains have been plugged in 4710 and the power switch activated 4715, the timing circuit 4740 may initiate a timing procedure 4742. In some additional aspects, the timing circuit 4740 may initiate a timing procedure 4742 once the power mains have been plugged into 4710 the receptacles without requiring activation 4715 of the power switch. In some aspects, the timing procedure 4742 may initialize a digital counter and initiate a timing signal to update the digital counter. Alternatively, the timing procedure 4742 may apply a stable DC timing voltage to an RC circuit, and the output of the RC circuit may be compared to a voltage threshold. If the timing circuit 4740 does not receive the over-ride signal 4728, the timing procedure 4742 may continue until the timer—either analog or digital—attains 4744 a predetermined value. In some aspects, the predetermined value may be related to a typical time required for the processor under test to complete the boot-up process (boot-up delay time 4724). If the counter attains 4744 the predetermined value, the hardware timing circuit 4740 may transmit 4748 a fault signal to the multicolor visualization device 4760.

In one example, the predetermined value may be empirically derived based on measuring the boot-up delay time 4724. In one non-limiting example, the predetermined value may represent an average of a plurality of measured boot-up delay times. In another non-limiting example, the predetermined value may represent the maximum value of a plurality of measured boot-up delay times. In still another non-limiting example, the predetermined value may be an average of a plurality of measured boot-up delay times plus an additional arbitrary value (such as 50% of the average). Alternatively, an arbitrary value may be chosen for the predetermined value as long as it is significantly greater than the expected boot-up delay time 4724. Thus, as a non-limiting example, the predetermined value for a processor having an expected boot-up delay time of between about 10 μsec. and about 200 μsec. may range from around 200 msec. to about 2 sec. In some non-limiting examples, the predetermined value may be about 200 msec, about 400 msec, about 600 msec, about 800 msec, about 1000 msec, (1 sec.), about 1200 msec, about 1400 msec, about 1600 msec, about 1800 msec, about 2000 msec, (2 sec.), or any value or range of values therebetween including endpoints.

As disclosed above, the hardware timing circuit 4740 may continue the timing procedure 4742 until the timer attains 4744 the predetermined value. Alternatively, if the hardware timing circuit 4742 receives 4746 the over-ride signal 4728 from the processor under test 4720 before attaining 4744 the predetermined value, the timing procedure 4742 may cease 4750 and the hardware timing circuit 4740 may stop 4752. In yet another aspect, if the hardware timing circuit 4742 receives 4746 the over-ride signal 4728 from the processor under test 4720 before attaining 4744 the predetermined value, the timing procedure 4742 may continue although the hardware timing circuit 4740 may not transmit 4748 the fault signal to the multicolor visualization device 4760. In aspects in which the hardware timing circuit 4742 receives 4746 the over-ride signal 4728 from the processor under test 4720 before attaining 4744 the predetermined value, the hardware timing circuit 4740 will not transmit 4748 the fault signal to the multicolor visualization device 4760.

Turning now to the multicolor visualization device 4760, the multicolor visualization device may comprise any one or series of LED devices. In one example, the multicolor visualization device may be a three-color LED composed of a red LED 4766*a*, a green LED 4766*b*, and a blue LED 4766*c*. These LED's can be powered either individually or in groups to generate a required notification color. In one example, all three LEDs 4766*a,b,c* may be activated to produce a white notification color. In one example, a dim white notification color may indicate that the modular energy system has been initialized and is in a standby state while a bright which color may indicate that the modular energy system is in a run-time state, thus ready for use. In another example, only the green LED 4766*b* may be active. The green notification color may indicate that the modular energy system or one of its functional modules is presently active and in a run-time state, for example providing power to a smart electrosurgical instrument. In yet another example, only the red LED 4766*a* may be active. The red notification color may indicate any one of a number of fault conditions. In one example, the red notification color may indicate that the processor under test 4720 has failed to complete its boot-up process, and that action is required.

Returning to the processor under test 4720, if the processor successfully completes 4726 the boot-up procedure, the processor may transmit 4730 configuration data to the multicolor visualization device 4760. A general LED driver circuit may receive 4762 the configuration data from the processor. The general LED driver circuit may then activate the LEDs 4766*a,b,c* to display the appropriate color indicative of the status of the modular energy device, such as a dim white color or a bright white color.

Alternatively, if the hardware timing circuit 4740 attains 4744 the predetermined value, the timing circuit 4740 may transmit 4748 the fault signal to the multicolor visualization device 4760. The fault signal may be received 4764 by an LED driver over-ride circuit, which may activate the red LED 4766*a* regardless of the state of the general LED driver circuit. In this manner, a red LED signal may be perceived by a user who will understand that a boot-up fault has occurred to the processor under test 4720.

EXAMPLES

Various aspects of the architecture for modular energy systems described herein with reference to FIGS. 47-51 are set out in the following numbered examples.

Example 1. A modular energy system for use in a surgical environment, the system comprising a plurality of modules, wherein each of the plurality of modules comprises one of an initial module, a terminal module, and a functional module, in which each of the functional modules and the terminal module comprises a module control circuit, and a local data bus comprising a communication switch, a first switch data path configured to permit data communication between the communication switch and the module control circuit, a second switch data path in data communication with the communication switch, and a third switch data path in data communication with the communication switch, and in which the initial module comprises a physical layer transceiver (PHY) in data communication with an initial module control circuit, a termination unit in data communication with the third data path of the terminal module, and an internal data bus comprising a serial array of the local data busses of the plurality of functional modules and the terminal module, in which a third switch data path of a functional module N is in data communication with a second switch data path of a functional module N+1, in which a second switch data path of the terminal module is in data communication with a third switch data path of a preceding functional module, and in which the internal data bus further comprises the physical layer transceiver (PHY) of the initial module in data communication with a second switch data path of a succeeding functional module.

Example 2. The modular energy system of Example 1, further comprising a routing system, wherein the routing system is in data communication with the internal data bus, and is configured to permit data communication between the internal data bus and a device or system separate from the modular energy system.

Example 3. The modular energy system of Example 2, wherein one of the plurality of modules comprises the routing system.

Example 4. The modular energy system of Example 3, wherein the one of the plurality of modules comprising the routing system, further comprises a header module or a communication module.

Example 5. The modular energy system of any one or more of Example 3 through Example 4, wherein the routing system is detachably connected to the one of the plurality of modules.

Example 6. The modular energy system of Example 5, wherein the one of the plurality of modules comprising the detachably connected routing system is configured to detect a presence of the detachably connected routing system.

Example 7. The modular energy system of any one or more of Example 2 through Example 6, wherein the routing system comprises a routing system processor and a routing system memory unit, wherein the routing system memory unit is configured to store instructions that, when executed by the routing system processor, cause the processor to execute one or more communication security protocols.

Example 8. The module energy system of Example 7, wherein the one or more communication security protocols comprise one or more of a MAC address table filter, a packet filter based on an IP address, a software protocol, or a port number, a stateful communication packet inspection, and an application layer firewall.

Example 9. The modular energy system of any one or more of Example 1 through Example 8, wherein the plurality of modules comprises at least three modules.

Example 10. The modular energy system of Example 9, wherein, for a module N, a data communication between a module N+1 and a module N−1 is routed around the communication switch of the module N when the communication switch of module N is non-functioning.

Example 11. The modular energy system of Example 10, wherein the local data bus of each of the plurality of modules further comprises a multiplexer comprising a first multiplex data path, a second multiplex data path, a third multiplex data path, and a data path selection line, and in which a fourth switch data path for a functional module or a terminal module is configured to permit data communication between the communication switch and the first multiplex data path of the multiplexer.

Example 12. The modular energy system of Example 11, wherein the third multiplex data path of the module N+1 is in data communication with the second multiplex data path of the module N−1.

Example 13. The modular energy system of Example 12, wherein the module N+1 is configured to form a communication exchange with the module N−1 via the fourth switch data path of the communication switch of the module N+1, the third multiplex data path of the data multiplexer of the module N+1, the second multiplex data path of the data multiplexer of the module N−1, and the fourth switch data path of the communication switch of the module N−1, when the communication switch of the module N is non-functional.

Example 14. The modular energy system of any one or more of Example 1 through Example 13, wherein the internal data bus further comprises a plurality of address lines, an address fault line in electrical communication with a voltage source, and an analog/digital converter (ADC) configured to convert a value of an analog voltage of the address fault line into a digital value, and in which each module N of the plurality of functional modules further comprises a local address generator circuit, a local address parity circuit, and a predictive address parity circuit for a functional module N+1.

Example 15. The modular energy system of Example 14, wherein the termination unit comprises a local address parity circuit.

Example 16. The modular energy system of any one or more of Example 14 through Example 15, wherein each module N of the plurality of functional modules comprises a parity comparison circuit configured to compare a predictive address parity value for a module N+1 and a local address parity value of a module N+1.

Example 17. The modular energy system of Example 16, wherein, for each module N of the plurality of modules, the module N causes the value of the analog voltage of the address fault line to change when the predictive address parity value for module N+1 does not equal the local address parity value of module N+1.

Example 18. The modular energy system of Example 17, wherein the change in value of the analog voltage is indicative of an address fault in module N+1.

Example 19. A system for notifying a user of a processor boot-up fault in a computerized device, in which the computerized device comprises a processor and a memory unit configured to store a plurality of instructions for execution by the processor, the system comprising a timing circuit and a notification device, in which the processor is configured to initiate a boot-up process based on at least some of the instructions stored in the memory unit when power is applied to the computerized device, in which the timing circuit is configured to initiate a timing procedure when power is applied to the computerized device, and in which the timing circuit is configured to transmit a fault signal to the notification device when the timing circuit attains a predetermined value.

Example 20. The system of Example 19, wherein the timing circuit comprises a first timing circuit comprising a digital counter configured to receive a timing signal, and a memory device configured to store the predetermined value, in which the timing signal is initiated when power is applied to the computerized device.

Example 21. The system of any one or more of Example 19 through Example 20, wherein the time circuit comprises a second timing circuit comprising an RC circuit, a comparator, and a circuit configured to generate a voltage threshold, in which a timing voltage is applied to the RC circuit when power is applied to the computerized device, and in which the voltage threshold comprises the predetermined value.

Example 22. The system of any one or more of Example 19 through Example 21, wherein the processor, on completion of the boot-up process, is configured to transmit an over-ride signal to the timing circuit when the boot-up process completes, and in which the timing circuit is configured to cease the timing procedure upon receipt of the over-ride signal from the processor.

Example 23. The system of any one or more of Example 19 through Example 22, wherein the notification device comprises a multicolor visualization device.

Example 24. The system of Example 23, wherein the processor, on completion of the boot-up process, further is configured to transmit a configuration signal to the multicolor visualization device.

Example 25. The system of any one or more of Example 23 through Example 24, wherein the multicolor visualization device comprises a three-color LED.

Example 26. The system of Example 25, wherein the three-color LED is configured to display a red color on receipt of the fault signal from the timing circuit.

Example 27. The system of any one or more of Example 25 through Example 26, wherein the three-color LED is configured to display a dim white color when the computerized device is in a standby mode, and a bright white color when the computerized device is in a run-time mode.

Modular Energy System with Hardware Mitigated Communication

Having described a general implementation of modular energy systems 2000, 3000, and 6000, and various surgical instruments usable therewith, for example, surgical instruments 2204, 2206, and 2208, the disclosure now turns to various aspects of modular energy systems comprising a hardware mitigated communication circuits and techniques. In other aspects, these modular energy systems are substantially similar to the modular energy system 2000, the modular energy system 3000, and/or the modular energy system 6000 described hereinabove. For the sake of brevity, various details of other modular energy systems described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

Hardware Mitigated Communication in a Modular System

As described hereinbelow with reference to FIG. 52, in various aspects, the present disclosure provides modular energy systems 2000, 3000, 6000 comprising hardware mitigated communication circuits and techniques. As disclosed above, with respect to FIG. 1-3, a surgical hub 106 can be embodied as a modular energy system 2000, as is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement. Other aspects of hardware mitigated communication techniques also are applicable to other modular energy systems 3000, 6000 described herein.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As illustrated in FIG. 15, each module in the modular energy system may include a first pass through hub connector 3074 and a second pass-through hub connector 3038. Each module may include a local data bus configured to direct data communications among the various components of the module. Further, the local data bus of each module may extend between the first pass through hub connector and the second pass-through hub connector. Once the modules that comprise the modular energy system are stacked together, interconnected by their respective first and second pass-through hub connectors, the interconnected local data busses together may form an internal data bus. Data may be received and transmitted through the internal data bus and are distributed among all of the modules via their respective local data busses.

Based on the description of the physical and data connectivity of the modules, as disclosed above, it can be understood that the entire internal data bus is composed of multiple mechanically linked local data busses of the various modules. One having experience in the use of data connector technology can well appreciate that each mechanical link (the pass-through hub connectors) may represent a point of communication failure or corruption. The individual pins of one pass-through hub connector may not securely mate with the corresponding receptacle of a second pass-through hub connector. The surfaces of the pins and/or receptacles may develop tarnish or corrosion over time, thereby forming a high resistive electrical block between pin and receptacle. Pins may bend or break on multiple couplings and de-couplings. In addition to communication faults due to mechanical issues at the connector sites, sources of communication loss or corruption may also be due to message collisions, network congestion, or data errors. In some cases, a transmitter may have a fault causing it not to transmit an intended data packet. Therefore, it is clear that methods and components may be required to assure that communications between modules are maintained, or at least determine if some data communication becomes lost or corrupted.

Figure 52:
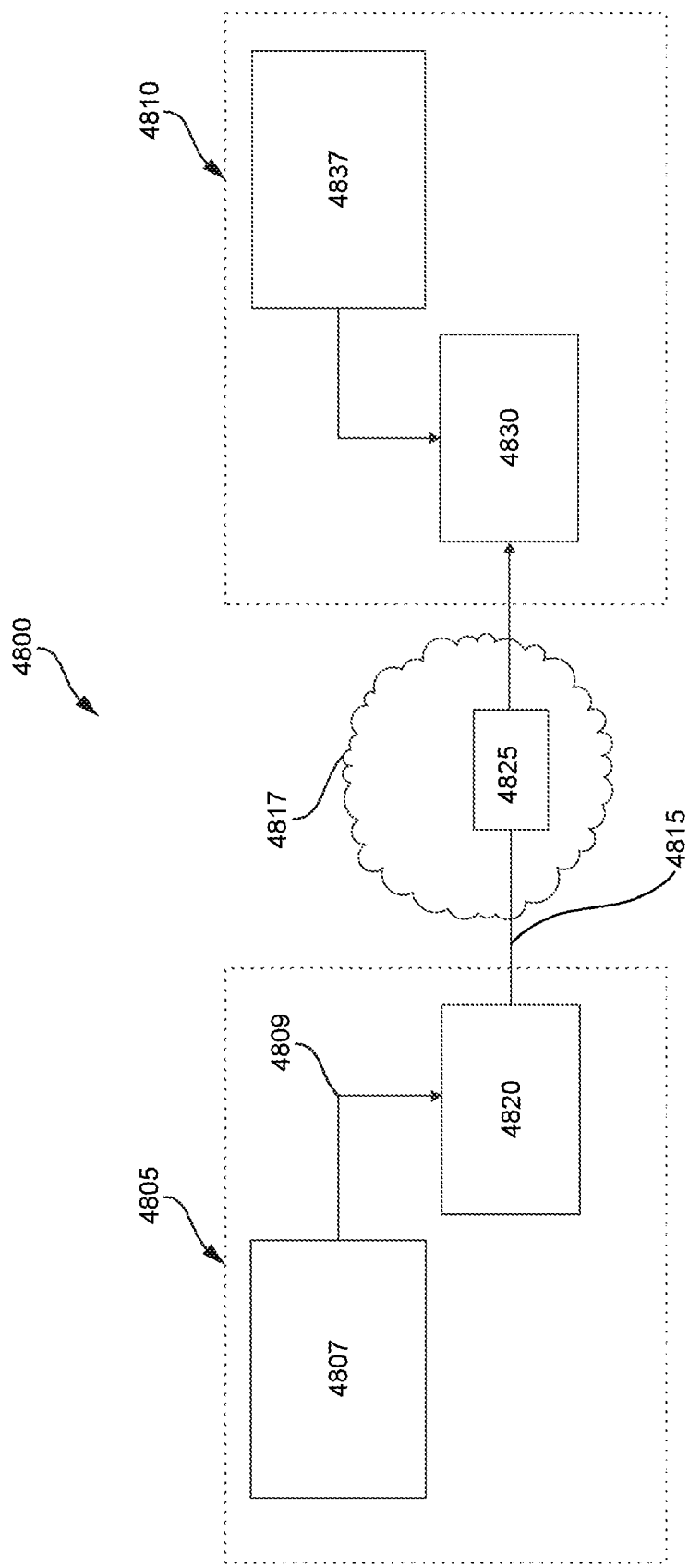
FIG. 52 is a block diagram of a communication link between a transmitting component and a receiving component, in accordance with at least one aspect of the present disclosure.

FIG. 52 depicts a block diagram 4800 of a communication transfer process between a transmitting module 4805 and a receiving module 4810. The communication transfer process depicted in FIG. 52 may apply to any suitable serial communication transfer protocol, especially a protocol that may transmit a data message as one or more data packets. While the process depicted in the block diagram 4800 may apply to any suitable communication protocol, its use may be considered in terms of an Ethernet protocol, as one non-limiting example.

For the transmitting module 4805, the data message may be suitably incorporated into one or more data packets 4825 in the transmitter software application communication layer 4820. The data message may be transmitted over the transmission medium 4815 to be received by the receiving module 4810, for example at the receiver software application communication layer 4830. The transmission medium 4815 may include any wired or wireless medium. The transmission medium 4815 may become unreliable 4817 due to any number of factors. Some sources of data message loss or corruption have already been discussed with respect to the internal data bus of the modular energy system, as disclosed above. If the transmission medium 4815 is a wireless medium, the source of unreliability 4817 may be due to atmospheric conditions, structural interference, frequency clashes, and similar effects known to compromise the integrity of a wireless transmission.

Without loss of generality, one may consider communication between two functional modules of the modular energy device. Each module may include a module control circuit which may be configured to execute computer instructions related to the particular functions of that module. The module control circuit may also execute the require instructions necessary to transmit or receive communications to or from other functional modules. Each functional module may include a local data bus which may include a communication switch in data communication with the control circuit. As disclosed above, when the modular energy system is assembled, the local data busses of the modules may be serially connected to form the internal data bus of the modular energy system. The internal data bus may form the communication medium 4815 over which the communication data packets 4825 may transfer between individual functional modules.

In order to determine if a data message has become lost or delayed, the transmitting module 4805 may include a transmitter transceiver timer 4807. The transmitter transceiver timer 4807 may include any type of hardware timer, including a real-time clock or a free-running counter. The transmitter software application communication layer 4820 may read a transmission time or count value from the transmitter transceiver timer 4807 and append those data 4809 into one or more data structures within the communication data packets 4825 comprising the data message being transmitted over the communication medium 4815.

The communication data packets 4825 transmitted by the transmitting module 4805 over the transmission medium 4815 may be received by the receiving module 4810. In particular, the receiver software application communication layer 4830 may receive the data message and unpack the data structure therein. The receiver software application communication layer 4830 may also extract the transmission time from the data structure. The receiver software application communication layer 4830 may also obtain a receipt time marking the time the data message was received. The receipt time may be obtained from a receiver transceiver timer 4837. The receiver transceiver timer 4837 may also include any type of hardware timer, including a real-time clock or a free-running counter. The receiver software application communication layer 4830 may use the receipt time to time stamp the receipt of the data message.

The receiver transceiver timer 4837 and the transmitter transceiver timer 4807 may be similar types of devices or different types of devices. In one aspect, the receiver transceiver timer 4837 and the transmitter transceiver timer 4807 may be the same device. In aspects in which the receiver transceiver timer 4837 and the transmitter transceiver timer 4807 are different devices, the two timers (4807 and 4837) may be synchronized. In one aspect, a transmitter module 4805 may send a synchronization message for example using the Precision Time Protocol (PTP or IEEE-1588 standard) to the receiver module 4810. The receiving module 4810 may then adjust the receiver transceiver timer 4837 to have a time as indicated by the header value. In alternative aspects, both the receiver transceiver timer 4837 and the transmitter transceiver timer 4807 may be synchronized to an independent time reference, such as a GPS or WWVB time source.

It may be understood that the process depicted in the block diagram 4800 may repeat with each transmission from the transmitting module 4805. That is, before a data message is transmitted over the medium 4815, a transmission time may be obtained from the transmitter transceiver timer 4807 and appended 4809 to the data message. On receipt of the data message, the receiving module 4810 may obtain a receipt time from the receiver transceiver timer 4837 and unpack the transmission time from the data message. The receiving module 4810 may make a number of comparisons of the times associated with sequentially received data messages. In one example, the receiving module 4810 may compare the transmission times of sequentially received data messages. In another example, the receiving module 4810 may compare a transmission time of a data message to its receipt time. In yet another example, the receiving module 4810 may compare receipt times of sequentially received data messages. Depending on the time comparisons made, the receiving module 4810 may respond in any appropriate manner.

It may be understood that, in general, the transmission times of sequentially transmitted data messages should have increasing values. If the data messages sequentially received by the receiving module 4810 have increasing transmission times, the receiving module 4810 may determine that the sequentially received data messages were sequentially transmit from the transmitting module 4805. However, if the transmission times of sequentially received data messages have the same transmission time or decreasing values of the transmission time, then the receiving module 4810 may determine that a transmission error has occurred. For example, if a first received message has the same transmission time as a second and later received message, then the receiving module 4810 may determine that the same message had been sent twice by the transmitting module 4805. If the first received message has a transmission time that is less than a transmission time of a second and later received message, there may be an indication of a message clash over the transmission medium 4815. For either of these two error conditions, the receiving module 4810 may shut down to a safe standby state. In addition, the receiving module 4810 may transmit an error message over the transmission medium 4815.

It may generally be understood that multiple data transmissions may occur while the modular energy system is in use. Even when the modular energy system is in a quiescent state, various modules may communicate with each other, for example to obtain status information. Thus, each receiving module 4810 may expect to receive multiple data messages from a given transmitting module 4805. As noted above, upon receipt of a data message, the receiving module 4810 may obtain a receipt time as a time stamp for the data message. The receiving module 4810 may obtain a receipt time from the receiver transceiver timer 4837 for each sequentially received data message. In some aspects, sequential data transmissions from a transmitting module 4805 may be spaced apart by a transmission interval (defined as a difference in the transmission times between sequential data messages). The receiving module 4810 may therefore expect a transmission interval time between receipt times associated with successive data messages. If the transmission interval between successively received data messages is greater than a predetermined value, the receiving module 4810 may determine that a transmission fault has occurred, such as a dropped packet or data message. The predetermined value may be based on an expected transmission interval. For example, a transmission interval may be about 10 ms. and thus the predetermined value may be set to this value. Alternatively, the predetermined value may represent an average transmission interval calculated from the transmission intervals measured between a number of data message receipt times. Alternatively, the predetermined value may represent a maximum value of transmission intervals among a number of data message receipt times. As another alternative, the predetermined value may represent an average transmission value increased by some fixed amount (for example 50%). In the event that the receiving module 4810 determines that a difference in receipt times between two successively received data messages is greater than the predetermined value, the receiving module 4810 may recognize the existence of an error condition. In the case of this error condition, the receiving module 4810 may shut down to a safe standby state. In addition, the receiving module 4810 may transmit an error message over the transmission medium 4815.

As disclosed above, the receiver transceiver timer 4837 and the transmitter transceiver timer 4807 may be synchronized. If the transmission of a communication data packet 4825 between the transmitting module 4805 and the receiving module 4810 is unimpeded, the difference between the transmission time and the receipt time should be fairly small. However, if the transmission medium 4815 is composed of an internal data bus of a modular energy system having multiple serially connected local data busses, the communication data packet 4825 will be relayed between the communication switches of successive energy system modules. It may be understood that a delay in the retransmission of the communication data packet 4825 between successive communication switches may occur due to data clashes, communication switch retransmission latency, error in communication data packet 4825 receipt, or other reasons. In such a case, the final receipt time of the communication data packet 4825 may be greater than a predetermined value. If the difference between a transmission time and a receipt time for a given communication data packet is greater than a predetermined value, the receiving module 4810 may determine that a transmission fault has occurred, such as a dropped or delayed packet, or that the data message is outdated and superseded by a more recent data message. The predetermined value may be based on an expected transit time between the transmitting module 4805 and the receiving module 4810. For example, a transit time may be on the order of 10's of µs and thus the predetermined value may be set to this value. Alternatively, the predetermined value may represent an average transit time calculated from the transit times measured between a number of data message transmission/receipt times. Alternatively, the predetermined value may represent a maximum value of transit times among a number of data message transmit/receipt times. As another alternative, the predetermined value may represent an average transit time increased by some fixed amount (for example 50%). In the event that the receiving module 4810 determines that a difference between the transmission time and the receipt time of a communication data packet 4825 is greater than the predetermined value, the receiving module 4810 may recognize the existence of an error condition. In the case of this error condition, the receiving module 4810 may shut down to a safe standby state. In addition, the receiving module 4810 may transmit an error message over the transmission medium 4815.

As disclosed above, the receiving module 4810, on detecting a transmission error associated with one or more data messages, may shut down to a safe standby state and transmit an error message over the transmission medium 4815. In some aspects, the transmitting module 4805, on receiving the error message, may address the error. In one aspect, on receiving the error message, the transmitting module 4805 may retransmit the previously sent data message.

As disclosed above, the modular energy system may be incorporated into a larger smart surgical system. Such a larger surgical system may include subsystems including, without limitation, one or more of a central surgical hub, a visualization system, a robotic surgical system, a smoke evacuation system, an irrigation system, an imaging system, and one or more patient status sensors. All of these subsystems may be interconnected by a surgical system bus. The surgical system bus may constitute any type of communication network allowing the various subsystems to exchange data with each other. The modular energy system internal bus, as previously disclosed above, may also be in data communication with the surgical subsystems and particularly the surgical system bus. Thus, a system data bus may include both the modular energy system internal bus and the surgical system bus.

It may be understood that data communication among the subsystems of the smart surgical system (including the modular energy system and its modules), may also be prone to similar message transmission errors as disclosed above in the context of communications among the various modules that compose the modular energy system. It may be recognized that the general process depicted in FIG. 52 and disclosed above for the modular energy system, may equally be applied to the larger smart surgical system.

In view of the disclosure above, it may be understood that any or all of the components of the smart surgical system—the surgical subsystems and the modules of the modular energy system—may incorporate a transceiver timer. All of the transceiver timers may be used as either a receiver transceiver timer or a transmitter transceiver timer depending on whether the module or subsystem acts as either a transmitting component or a receiving component. All of the transceiver timers may be synchronized according to any of the methods disclosed above. It may be understood that the transmitting component may not be the same component as the receiving component. Message data may be transmitted over the entirety of the system data bus (incorporating both the surgical system bus and the internal data bus of the modular energy system).

In keeping with the disclosure above and FIG. 52, a transmitting component may obtain a transmission time from its associated (transmitter) transceiver timer, and append the transmission time to the data message. The data message may be transmitted over the system data bus. The receiving component may receive the data message, extract the transmission time, and obtain a receipt time from its associate (receiver) transceiver timer. The transmitting component may obtain a new transmission time and append it to each subsequent data message being sent. The receiving component may receive each data message, extract the new transmission time from each data message, and obtain a receipt time for each data message.

In one aspect, the receiving component may compare the transmission times of sequentially received data messages. In one aspect, the receiving component may compare the receipt times of sequentially received data messages. If the receiving component determines that the transmission times of sequentially received data messages do not increase, but either have the same value or decreasing values, the receiving component may enter a safe shut-down mode and transmit an error message over the system data bus. If the receiving component determines that the difference between the receipt times of two sequentially received data messages is greater than a predetermined value, the receiving component may enter a safe shut-down mode and transmit an error message over the system data bus. In one aspect, the transmitting component, upon receipt of the error message may retransmit one or more of the previously transmitted data messages.

While the operation of the messaging error system has been summarized above with respect to the smart surgical system, it may be understood that various detailed aspects disclosed above with respect to the operation of such a system in the modular energy system may still obtain with respect to the larger system.

EXAMPLES

Various aspects of the modular energy systems comprising hardware mitigated communication circuits and techniques described herein with reference to FIG. 52 are set out in the following numbered examples:

Example 1. A modular energy system for use in a surgical environment, the system including a plurality of functional modules, wherein at least two of the plurality of functional modules is composed of a module control circuit, a local data bus having a communication switch in data communication with the control circuit, and a transceiver timer, and an internal data bus including a serial array of the local data busses of the plurality of functional modules in mutual data communication, in which a first functional module of the plurality of functional modules is configured to transmit a data message over the internal data bus to a second functional module of the plurality of functional modules, in which the first functional module is configured to obtain a transmission time from a transceiver timer of the first functional module, append the transmission time to the data message, and transmit the data message over the internal data bus to the second functional module, and in which the second functional module is configured to receive the data message over the internal data bus from the first functional module, obtain a receipt time from a transceiver timer of the second functional module, and obtain the transmission time from the data message.

Example 2. The modular energy system of Example 1, wherein the second functional module is configured to compare a value of the receipt time to a value of the transmission time.

Example 3. The modular energy system of Example 2, wherein the second functional module, upon determining that a difference between the value of the receipt time and the value of the transmission time is greater than a predetermined value, is configured to enter into a safe shut-down mode, and transmit an error message over the internal data bus.

Example 4. The modular energy system of Example 1, in which the first functional module is further configured to obtain a second transmission time from the transceiver timer of the first functional module, append the second transmission time to a second data message, and transmit the second data message over the internal data bus to the second functional module, and in which the second functional module is configured to receive the second data message over the internal data bus from the first functional module, obtain a second receipt time from the transceiver timer of the second functional module, and obtain the second transmission time from the second data message.

Example 5. The modular energy system of Example 4, in which the second functional module is configured to compare a value of the second transmission time to a value of the transmission time.

Example 6. The module energy system of Example 5, in which the second functional module, upon determining that the second transmission time is equal to or less than the transmission time, is configured to enter into a safe shut-down mode and transmit an error message over the internal data bus.

Example 7. The modular energy system of any one or more of Examples 4 through 6, in which the second functional module is configured to compare a value of the second receipt time to a value of the receipt time.

Example 8. The modular energy system of Example 7, in which the second functional module, upon determining that a difference between a value of the second receipt time and a value of the receipt time is greater than a predetermined transmission interval, is configured to enter into a safe shut-down mode, and transmit an error message over the internal data bus.

Example 9. The modular energy system of any one or more of Examples 1 through 8, in which the first functional module is configured to transmit over the internal data bus a timer synchronization message based on a time of the first functional module transceiver timer, and in which the second functional module, upon receiving the timer synchronization message, is configured to synchronize the time of the second functional module transceiver timer to a value contained in the timer synchronization message.

Example 10. The modular energy system of any one or more of Examples 1 through 9, in which the first functional module, on receiving an error message over the internal data bus from the second functional module, is configured to resend a previous data message.

Example 11. A smart surgical system composed of a plurality of surgical subsystems in mutual data communication over a surgical system bus, in which at least one of the plurality of surgical subsystems comprises a subsystem transceiver timer, and a modular energy system including a plurality of functional modules, in which at least one of the plurality of functional modules has a module control circuit, a local data bus comprising a communication switch in data communication with the control circuit, and a transceiver timer, and an internal data bus comprising a serial array of the local data busses of the plurality of functional modules in mutual data communication, in which a system data bus comprises the internal data bus of the modular energy system in data communication with the surgical system bus, in which a transmitting component comprises one of the plurality of surgical subsystems or one of the plurality of functional modules, in which a receiving component comprises one of the plurality of surgical subsystems or one of the plurality of functional modules and is not the transmitting component, in which the transmitting component is configured to transmit a data message over the system data bus to the receiving component, in which the transmitting component is configured to obtain a transmission time from a transceiver timer of the transmitting component, append the transmission time to the data message, and transmit the data message over the system bus to the receiving component; and in which the receiving component is configured to receive the data message over the system data bus from the transmitting component, obtain a receipt time from a transceiver timer of the receiving component, and obtain the transmission time from the data message.

Example 12. The smart surgical system of Example 11, in which the plurality of surgical subsystems includes one or more of a central surgical hub, a visualization system, a robotic surgical system, a smoke evacuation system, an irrigation system, an imaging system, and one or more patient status sensors.

Example 13. The smart surgical system of any one or more of Examples 11 through 12, wherein the receiving component is configured to compare a value of the receipt time to a value of the transmission time.

Example 14. The smart surgical system of claim 13, wherein the receiving component, upon determining that a difference between the value of the receipt time and the value of the transmission time is greater than a predetermined value, is configured to enter into a safe shut-down mode, and transmit an error message over the system data bus.

Example 15. The smart surgical system of any one or more of Examples 11 through 14, in which the transmitting component is further configured to obtain a second transmission time from the transceiver timer of the transmitting component, append the second transmission time to a second data message, and transmit the second data message over the system data bus to the receiving component, and in which the receiving component is configured to receive the second data message over the system data bus from the transmitting component, obtain a second receipt time from the transceiver timer of the receiving component, and obtain the second transmission time from the second data message.

Example 16. The smart surgical system of Example 15, in which the receiving component is configured to compare a value of the second transmission time to a value of the transmission time.

Example 17. The smart surgical system of Example 16, in which the receiving component, upon determining that the second transmission time is equal to or less than the transmission time, is configured to enter into a safe shut-down mode and transmit an error message over the system data bus.

Example 18. The smart surgical system of any one or more of Examples 15 through 17, in which the receiving component is configured to compare a value of the second receipt time to a value of the receipt time.

Example 19. The smart surgical system of Example 18, in which the receiving component, upon determining that a difference between a value of the second receipt time and a value of the receipt time is greater than a predetermined transmission interval, is configured to enter into a safe shut-down mode and transmit an error message over the system data bus.

Example 20. The smart surgical system of any one or more of Examples 11 through 19, in which the transmitting component is configured to transmit over the system data bus a timer synchronization message based on a time of the transmitting component transceiver timer, and in which the receiving component, upon receiving the timer synchronization message, is configured to synchronize the time of the receiving component transceiver timer to a value contained in the timer synchronization message.

Example 21. The smart surgical system of any one or more of Examples 11 through 20, in which the transmitting component, on receiving an error message over the system data bus from the receiving component, is configured to resend a previous data message.

Inductive Charging

Having described a general implementation of modular energy systems 2000, 3000, 6000, and various surgical instruments usable therewith, for example, surgical instruments 2204, 2206, and 2208, the disclosure now turns to various aspects of modular energy systems 2000, 3000, 6000 comprising inductive charging circuits and techniques. In other aspects, these modular energy systems are substantially similar to the modular energy system 2000, the modular energy system 3000, and/or the modular energy system 6000 described hereinabove. For the sake of brevity, various details of other modular energy systems described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

Inductive Charging

As described hereinbelow with reference to FIGS. 53-55, in various aspects, the present disclosure provides modular energy systems 2000, 3000, 6000 comprising an inductive charger built into the header module to wireless charge devices placed above the header module. In another aspect, a wireless charging station module can be connected to the modular energy system 2000, 3000, 6000 to wirelessly charge devices connected to the wireless charging station module.

In various general aspects, cable management in the OR can be a significant challenge because of the multitude of connections from each piece of equipment back to the wall. In some aspects, additional cables may be made from these instruments to the surgical devices which go to the patient. For example, due to the vast number of these surgical devices there can be a large web of cables emanating from the patient and going outward (or upward) to the wall or tower connections.

In some aspects, using surgical devices that get power from a battery can help eliminate some of the cables in the operating room; however, then the battery needs charged. In one aspect, to accommodate charging the battery without a cable an inductive charging system can be added to the header module of the Modular Energy platform. In one aspect, adding an inductive charging system involves adding a charging coil to the top surface of the header but beneath the enclosure so it is not accessible to modification or liquids. In various aspects, the enclosure is metal, however this could interfere with the magnetic fields and cause internal heating of the enclosure, thus it is recommended to change out at least a portion of the enclosure above the charging system to a non-metallic material, for example plastic. The coil may be located by a foam like material called EPAC and connected back to the main printed circuit board assembly (PCBA) via internal cables. In various aspects, a mating coil would have to be provided on the device to be charged by the inductive charging system.

An inductive charging system can be used for a variety of items. One such example is to provide power to a wireless module. This module may need to be mobile so wires would ruin its experience. In various general aspects, the addition of an inductive charging system allows an alternative expansion route on the Mantle system. For example, previously the expansion was only allowed below the header, but with the addition of an inductive charging wireless module expansion can go above the header as well. Communication to the inductive charging wireless module can be done via bluetooth/ethernet/etc. instead of the backplane. Additionally, in one aspect, accessories such as a wireless foot switch could also be charged on the top of the unit in-between usage. In various aspects, an additional item that could be charged is speakers or cellphones especially for those surgeons who play music in the operating room (OR). Typically those devices are dangled close to an outlet in often not ideal locations such as on the floor or on a window sill. In one general aspect, anything that can run off a battery could run of the charging station.

Figure 53:
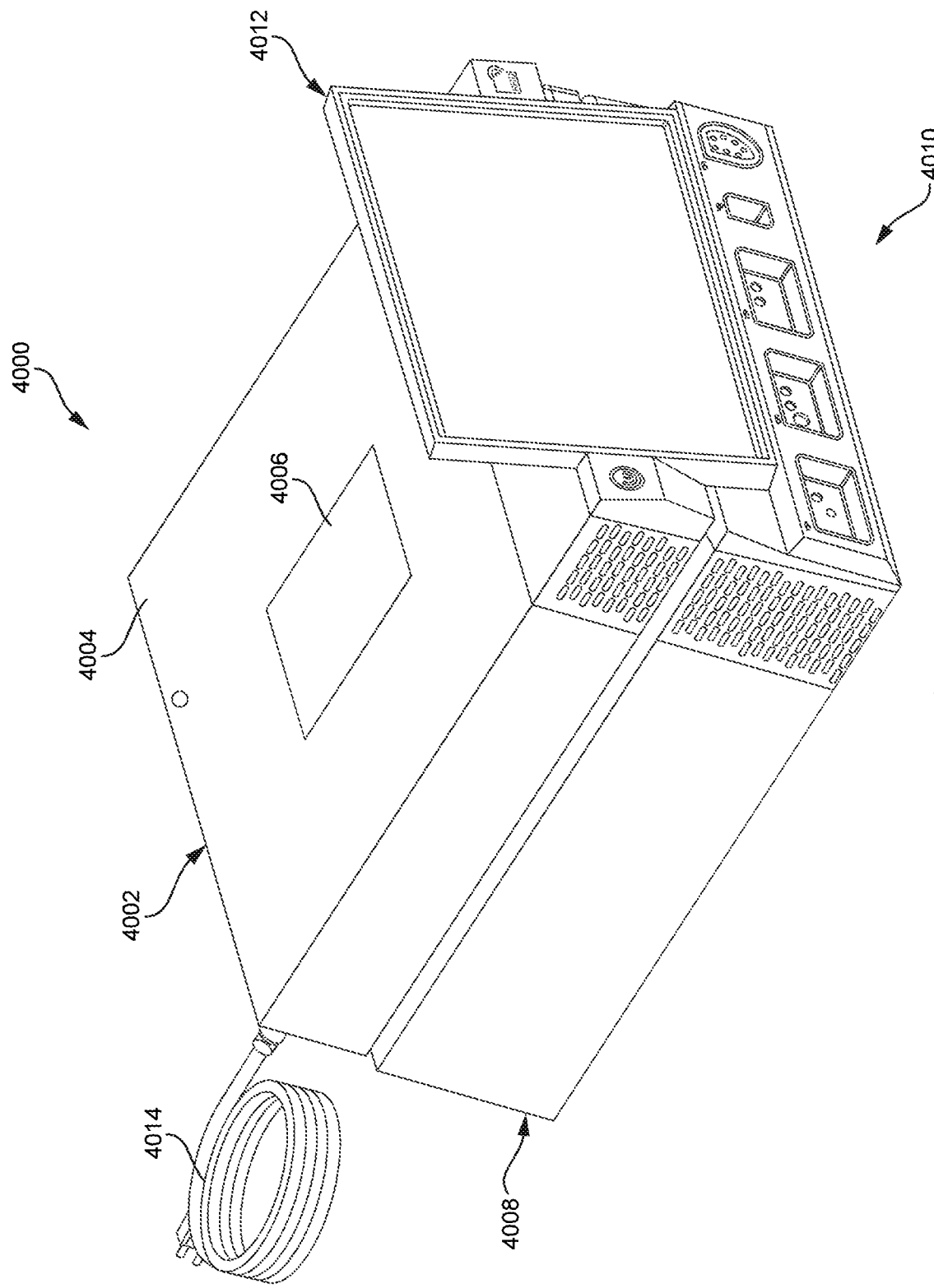
FIG. 53 illustrates a potential location of a charging coil on a header module of the modular energy system, in accordance with at least one aspect of the present disclosure.
Figure 54:
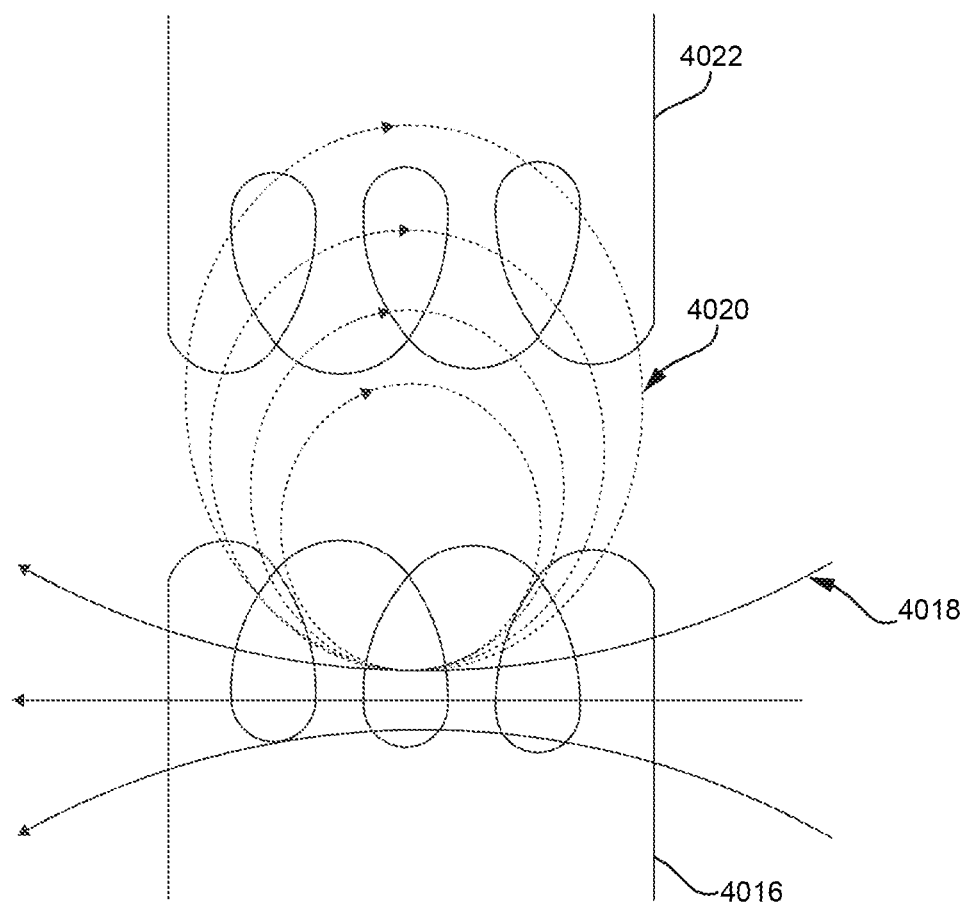
FIG. 54 is a diagram of how inductive charging system can transfer power wirelessly between two devices, in accordance with at least one aspect of the present disclosure.
Figure 55:
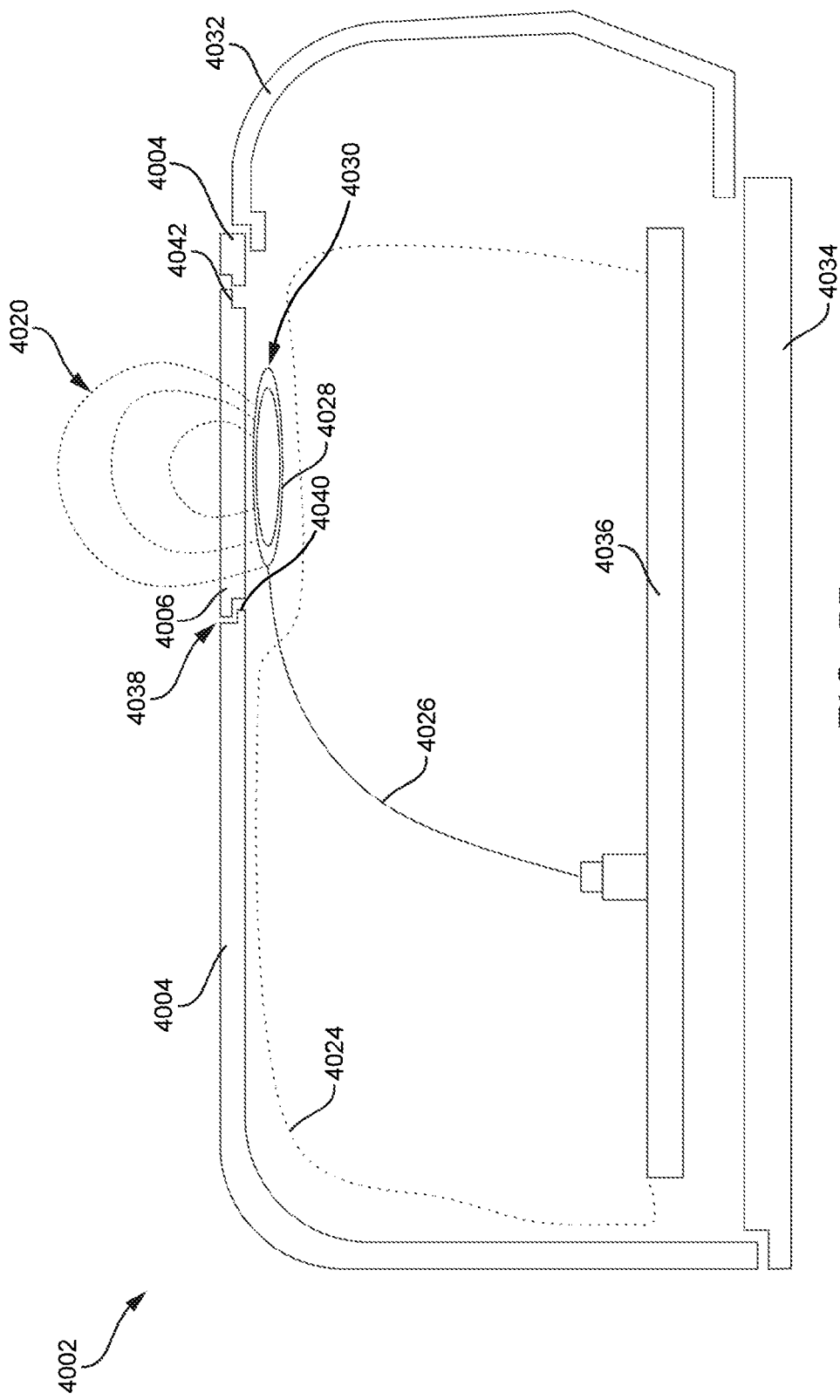
FIG. 55 illustrates how the coil would rest inside of the header module, in accordance with at least one aspect of the present disclosure.

In one aspect, FIGS. 53-55 illustrate the addition of an inductive charging system into a header module 4002 of a modular energy system 4000. Referring to FIG. 53, the header module 4002 may have a piece of the top enclosure 4004 replaced with a non-metallic section 4006. For example, the non-metallic section 4006 could be made of plastic. Under the non-metallic section 4006 the inductive coil may reside. The inductive coil could generate an oscillating magnetic field above the non-metallic section 4006 and a device with a receiver coil would be placed over top of the non-metallic section 4006 to charge the battery of the device. The header module 4002 may have a power cable 4014 that would go to an electrical outlet to provide power to the modular energy system 4000. A generator module 4008 may be placed under the header module 4002. The generator module 4008 may have a variety of ports 4010 for providing power to different devices. The header module 4004 may comprise a screen 4012. In certain aspects, the display screen 4012 can be removable from the header module 4002. In other aspects, the display screen 4012 can be built into the header module 4002.

FIG. 54 is a diagram of how an inductive coil 4016 can generate an oscillating magnetic field 4020 that may be received by a receiver coil 4022. Electrical current may be run through the inductive coil 4016 in the direction 4018 to generate the oscillating magnetic field 4020. The receiver coil 4022 may be placed within the oscillating magnetic field to generate electrical current in the receiver coil 4022. The electrical current generated in the receiver coil 4022 can be used to charge a battery in a device. Thus, a device may have a battery charged without any wires directly connecting the device to the charging system.

Referring to FIG. 55, some of the internal components of the header module 4002 are shown. The top enclosure 4004 may be attached to the bottom enclosure 40034 and the front bezel 4032. In one aspect, the top enclosure may be made of metal, the bottom enclosure may be made of metal, and the front bezel may be made of plastic. In various aspects, there may be a hole 4038 in the top enclosure. The edge of the hole 4038 can define a protrusion 4040 in the top enclosure 4004 that may mate with a protrusion 4042 of the nonmetallic section 4006. For example, the protrusion of the protrusion 4042 of the nonmetallic section 4006 may rest on top of the protrusion 4040 coming out off of the top enclosure 4004. The top of the nonmetallic section 4006 may rest even with the top of the enclosure 4004, when it is placed to cover the hole 4038. Directly beneath the hole 4038 the inductive coil 4028 may rest on top of the EPAC 4024. In one aspect, the EPAC can locate the placement of the inductive coil 4028 such that it is held in place and does not move from below the nonmetallic section 4006. The inductive coil 4028 can have a cable 4026 that electrically connects the inductive coil 4006 with the printed circuit board 4036. The printed circuit board may control the current that goes to the inductive coil 4028 such that the inductive coil 4028 can generate an oscillating magnetic field 4020. A device with a receiver coil can be placed on top of the header module 4002 such that a receiver coil in the device is placed above the nonmetallic section 4006. The receiver coil may then be within the oscillating magnetic field 4020, which may generate a current in the receiver coil that could be used to charge a battery in the device. The above described aspect is one example of a wireless charging system. Other aspects are envisioned that could be implemented by using different standard wireless charging techniques.

Wireless Charging of Handles and Accessories

As described hereinbelow with reference to FIG. 56, in various aspects, the present disclosure provides modular energy systems 2000, 3000, 6000 comprising wireless charging of handles and accessories. In another aspect, a wireless charging station module can be connected to the modular energy system 2000, 3000, 6000 to wirelessly charge devices connected to the wireless charging station module. Many current instruments/accessories used in the medical field today are charged prior to cleaning and sterilization. This process may pose a risk that the instrument/accessory may not be fully charged once it reaches the sterile field for surgery. The current process for rechargeable handles/batteries typically requires charging to be done by the cleaning and sterilization department prior to sterilization being completed. This workflow does not allow the OR staff to confirm that a battery is fully charged prior to starting the procedure. If the battery is not sufficiently, then charged the battery has to go back through the cleaning and sterilization process before it can be used again. The surgery can continue only if another battery is available. Another potential problem with this design is that batteries can lose charge while sitting on a shelf. The steps for the current reusable technology may be handle used in surgery, handle cleaned, handle charged, handle placed in pouch, handle sterilized, and then the handle is placed on a shelf without the battery status being displayed.

In various aspects, a wireless charging station could be used to allow instruments/accessories to be charged after cleaning and sterilization. This system would allow nurses/surgeons to see the status of a battery charge prior to selecting it for surgery. A reusable handle/battery could be wirelessly charged through an inductive coil. An inductive charging pad could be used that would be capable of wirelessly charging a battery through known sterilization wrapping, such as a peel pouch, autoclave wrapping, etc. The charging station could have multiple inductive charging pads. The charging station could display the status of all handles/batteries connected to the system. The charging station can support multiple configurations (wireless FSW, Instrument Handles, or Accessories). The wireless charging system could be placed on the modular energy system cart, somewhere else in OR, or possibly in the central processing department (where sterilization takes place). The wireless charging system could wirelessly communicates status to the modular energy system. The proposed reusable handle/battery steps with a wireless charging system would be handle used in surgery, handle cleaned, handle placed in pouch, handle sterilized, handle sterilized, and then handle placed on charger in sterile pouch with the battery status displayed.

Wireless charging allows customers to charge an instrument/accessory after sterilization has taken place and reduce the chances of a partially charged instrument being used in surgery. Some of the key advantages of a wireless charging system are to see the status of the handle before opening up sterile pouch. For example, a light could indicate available battery life in a "Sterile" state. Batteries can continue to charge while "on the shelf". Normally batteries that are charged prior to sterilization could drain while sitting on a shelf. The device handle would not need to be charged prior to cleaning/sterilization. A battery could be wirelessly charged during an operation through aseptic transfer (in sterile wrapping) to be used on a patient. The cleaning/sterilization department would not need to manage charging of reusable instruments. The charging station could wirelessly communicates status of connected devices to the modular energy system. Modular energy system could then recommend which handle to connect and use based on battery percent, usage history, reliability estimates, and etc.

Figure 56:
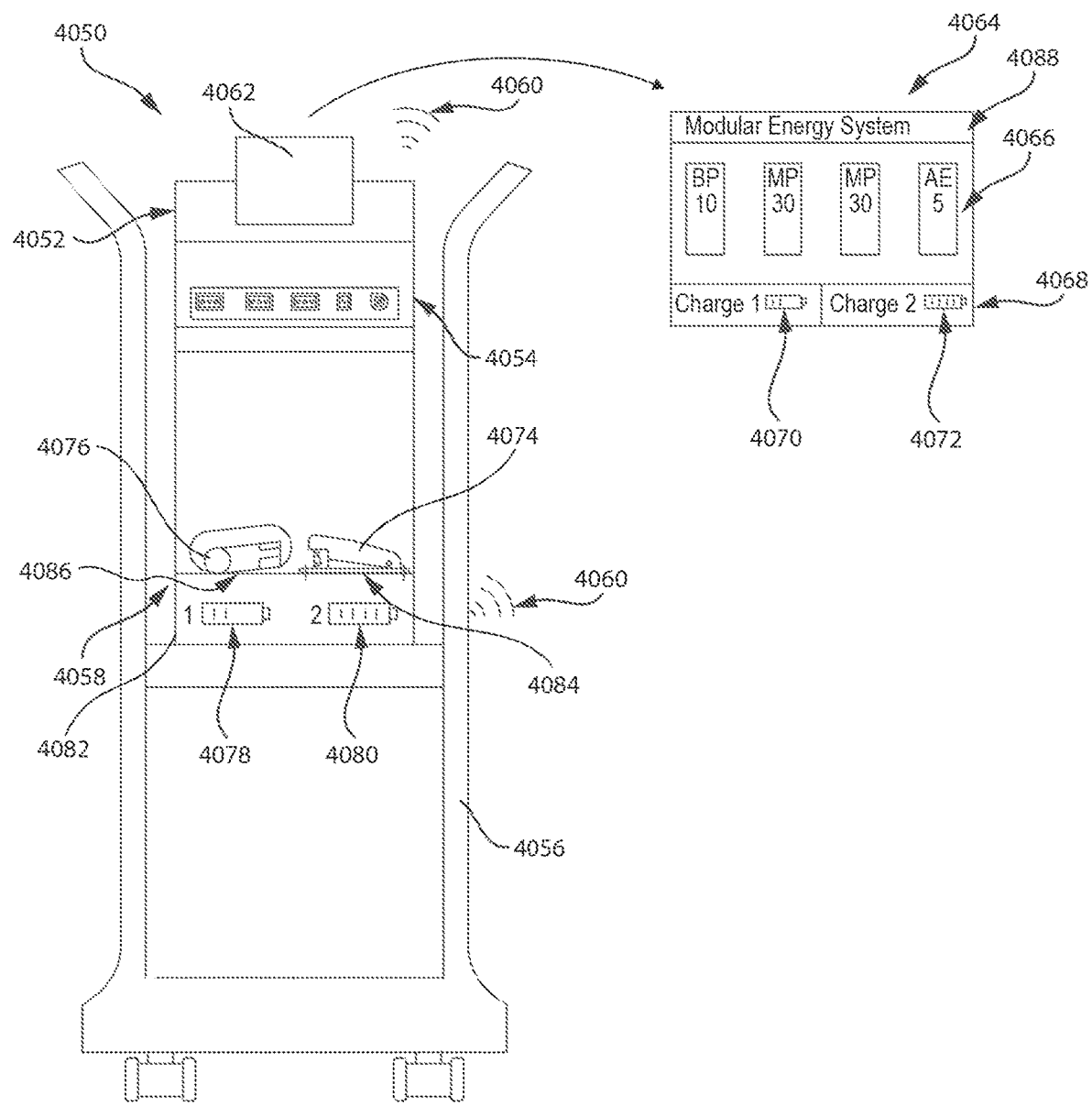
FIG. 56 illustrates a wireless charging station module as part of a modular energy system, in accordance with at least one aspect of the present disclosure.

In one aspect, FIG. 56 illustrates a wireless charging station module 4058 as part of a modular energy system 4050. The modular energy system 4050 may comprise a header module 4052, a generator module 4054, and a wireless charging station module 4058. In certain aspects, the modular energy system 4050 may be placed on a modular energy system cart 4056. In various other aspects, the wireless charging station module 4058 could be placed anywhere in the OR room. The wireless charging station module 4058 may have a dedicated power cord or it may be connected to the modular energy system 4050 for power. The wireless charging station module 4058 may have charge indicators 4078, 4080 on the side 4058 of the wireless charging station module 4058. A multitude of devices may be charged by the wireless charging station module 4058. The wireless charging station module 4058 has two charging locations 4086, 4084 on the top of the wireless charging station module 4058. For example, a device handle 4076 is placed on charging location 4086 and a wireless foot switch 4074 is placed on charging location 4084. In alternative aspects, there can be more or less charging locations on top of the wireless charging station module 4058. The charge indicators 4078, 4080 can indicate the percentage of charge for a device on the charge location. The charge indicator 4078 indicates the percentage that the device on charge location 4086 is charged and the charge indicator 4080 indicates the percentage that the device on charge location 4084 is charged. For example, the charge indicator 4078 indicates that the handle 4076 has a 50 percent charge, and the charge indicator 4080 indicates that the wireless foot switch 4074 is fully charged.

Still referring to FIG. 56, the wireless charging station module 4058 can be in wireless communication 4060 with the header module 4052. For example, the wireless charging station module 4058 can connect with the header module 4052 via wifi or Bluetooth technology. The header module 4062 comprises a display screen 4062 that shows the display 4064. The display 4064 contains information for the different modules of the modular energy system 4050. For example, the display 4064 illustrates modular energy system information 4088 for the modular energy system 4040, generator module information 4066 for the generator module 4054, and wireless charging station module information 4068 for the wireless charging station module 4058. In some aspects, the wireless charging station module information 4068 contains the percentage that a device connected to the wireless charging station module 4058 is charged. For example, the charge percent indicator 4070 displays the same information as the charge indicator 4078 and the charge indicator 4072 displays the same information as the charge indicator 4080.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A method of mitigating a function of a user interface (UI) display of a modular energy system, the method comprising:
receiving, by a video data converter circuit, formatted video data at an input channel of the video data converter circuit, wherein the input channel is coupled to a processor and the formatted video data represents an expected image to be displayed on a display, the video data converter having two output channels, wherein a first output channel is coupled to the display and a second output channel is coupled back to the processor, wherein the processor is configured to couple to a surgical instrument;
providing, by the video data converter circuit, differential video signaling data to the display from the first output channel of the video data converter circuit;
providing, by the video data converter circuit, a copy of the differential video signaling data to the processor from the second output channel; and
determining, by the processor, whether the differential video signaling data on the second output channel is changing over time.

2. The method of claim 1, comprising reconstructing, by the processor, an image based on the differential video signaling data on the second output channel.

3. The method of claim 2, comprising:
comparing, by the processor, the reconstructed image to the expected image; and
enabling, by the processor, activation of the surgical instrument based on a match between the reconstructed image and the expected image.

4. The method of claim 2, comprising:
comparing, by the processor, the reconstructed image to the expected image; and
disabling, by the processor, activation of the surgical instrument based on a mismatch between the reconstructed image and the expected image.

5. The method of claim 1, comprising disabling, by the processor, activation of the surgical instrument based on the differential video signaling data on the second output channel not changing over time when expected.

6. A surgical system comprising:
a display;
a surgical instrument;
a module coupled to the surgical instrument; and
a header module coupled to the module and the display, the header module comprising:
a processor to generate formatted video data to be displayed on the display, wherein the formatted video data is indicative of a state of the surgical instrument, and wherein the formatted video data represents an expected image;
a video data converter circuit comprising:
an input channel coupled to the processor;
a first output channel coupled to the display; and
a second output channel coupled to the processor;
wherein the video data converter circuit is to:
receive the formatted video data at the input channel;
transmit differential video signaling data to the display from the first output channel;
transmit a copy of the differential video signaling data to the processor from the second output channel; and
wherein the processor is further to determine whether the differential video signaling data on the second output channel is changing over time.

7. The surgical system of claim 6, wherein the processor is further to reconstruct an image based on the differential video signaling data on the second output channel.

8. The surgical system of claim 7, wherein the processor is further to:
compare the reconstructed image to the expected image; and
enable activation of the surgical instrument based on a match between the reconstructed image and the expected image.

9. The surgical system of claim 7, wherein the processor is further to:
compare the reconstructed image to the expected image; and
disable activation of the surgical instrument based on a mismatch between the reconstructed image and the expected image.

10. The surgical system of claim 6, wherein the processor is further to disable activation of the surgical instrument based on the differential video signaling data on the second output channel not changing over time when expected.

11. The surgical system of claim 6, wherein the module is an energy generator module.

12. A method of mitigating a function of a user interface (UI) display of a modular energy system, the method comprising:
- receiving, by a video data converter circuit, formatted video data at an input channel of the video data converter circuit, wherein the input channel is coupled to a processor and the formatted video data represents an expected image to be displayed on a display, the video data converter having two output channels, wherein a first output channel is coupled to the display and a second output channel is coupled back to the processor, wherein the processor is configured to couple to a surgical instrument;
- providing, by the video data converter circuit, differential video signaling data to the display from the first output channel of the video data converter circuit;
- providing, by the video data converter circuit, a copy of the differential video signaling data to the processor from the second output channel;
- reconstructing, by the processor, an image based on the differential video signaling data on the second output channel;
- comparing, by the processor, the reconstructed image to the expected image; and
- controlling, by the processor, an activation of the surgical instrument based on the comparison.

13. The method of claim 12, further comprising enabling, by the processor, activation of the surgical instrument based on a match between the reconstructed image and the expected image.

14. The method of claim 12, further comprising disabling, by the processor, activation of the surgical instrument based on a mismatch between the reconstructed image and the expected image.

* * * * *